US011898981B2

(12) United States Patent
Abdolahad et al.

(10) Patent No.: US 11,898,981 B2
(45) Date of Patent: Feb. 13, 2024

(54) REAL-TIME AND LABEL FREE ANALYZER FOR IN-VITRO AND IN-VIVO DETECTING THE SUSPICIOUS REGIONS TO CANCER

(71) Applicants: Mohammad Abdolahad, Tehran (IR); Zohreh Sadat Miripour, Tehran (IR); Parisa Aghaee, Tehran (IR); Hadi Ghafari, Tehran (IR); Naser Namdar Habashi, Tabriz (IR); Fereshteh Abbasvandi, Tehran (IR)

(72) Inventors: Mohammad Abdolahad, Tehran (IR); Zohreh Sadat Miripour, Tehran (IR); Parisa Aghaee, Tehran (IR); Hadi Ghafari, Tehran (IR); Naser Namdar Habashi, Tabriz (IR); Fereshteh Abbasvandi, Tehran (IR)

(73) Assignee: NANO HESGARSAZAN SALAMAT ARYA INCUBATION CENTER FOR MEDICAL EQUIPMENT AND DEVICES, Tehran (IR)

( * ) Notice: Subject to any disclaimer, the term of this patent is extended or adjusted under 35 U.S.C. 154(b) by 289 days.

(21) Appl. No.: 17/228,859

(22) Filed: Apr. 13, 2021

(65) Prior Publication Data

US 2021/0231600 A1 Jul. 29, 2021

Related U.S. Application Data

(63) Continuation-in-part of application No. 16/010,510, filed on Jun. 17, 2018, now Pat. No. 11,181,499.

(Continued)

(51) Int. Cl.

*G01N 27/327* (2006.01)
*G01N 27/48* (2006.01)

(Continued)

(52) U.S. Cl.

CPC ..... *G01N 27/3278* (2013.01); *A61B 5/14735* (2013.01); *A61B 5/6849* (2013.01);

(Continued)

(58) Field of Classification Search

CPC ............... G01N 27/3278; G01N 27/48; G01N 33/4833; G01N 27/3277; A61B 5/14735;

(Continued)

(56) References Cited

U.S. PATENT DOCUMENTS

2002/0188221 A1 * 12/2002 Sohrab ............ A61B 5/150358 600/573
2009/0076496 A1 * 3/2009 Azure ................ A61B 18/1492 606/34

(Continued)

*Primary Examiner* — Andrey Shostak
(74) *Attorney, Agent, or Firm* — Bajwa IP Law Firm; Haris Zaheer Bajwa

(57) ABSTRACT

A method for non-invasive detecting and tracing cancer. The method includes fabricating a probe including two reference electrodes, a working electrode located inside a first reference electrode of the two reference electrodes, and a counter electrode located inside a second reference electrode of the two reference electrodes, putting the probe on a part of skin adjacent to a target location inside a patient's body, inserting the two reference electrodes inside the target location through the part of skin, inserting the working electrode and the counter electrode into the target location by releasing the working electrode and the counter electrode through the two reference electrodes, recording a cyclic voltammetry (CV) response of hypoxia-related hydrogen peroxide ($H_2O_2$) release in the target location by applying a set of electrical potentials to the probe, measuring an oxidation current peak of the recorded CV response, and detecting a cancerous tumor at the target location by comparing the measured oxidation current peak with a set of reference values.

19 Claims, 72 Drawing Sheets

1910 1904 1902 1906 1912 1908 1914 1900 1920 1916 1922 1918

Related U.S. Application Data

(60) Provisional application No. 62/563,673, filed on Sep. 27, 2017, provisional application No. 62/522,115, filed on Jun. 20, 2017.

(51) Int. Cl.
*A61B 5/1473* (2006.01)
*A61B 5/00* (2006.01)
*G01N 33/483* (2006.01)

(52) U.S. Cl.
CPC ......... *G01N 27/48* (2013.01); *G01N 33/4833* (2013.01); *A61B 2562/0285* (2013.01); *A61B 2562/046* (2013.01); *G01N 27/3277* (2013.01)

(58) Field of Classification Search
CPC .......... A61B 5/6849; A61B 2562/0285; A61B 2562/046
See application file for complete search history.

(56) References Cited

U.S. PATENT DOCUMENTS

2015/0005788 A1* 1/2015 Sniffin ...................... B65B 5/10
606/139
2015/0114141 A1* 4/2015 Maeno ................... G01N 1/405
977/962

* cited by examiner

REAL-TIME AND LABEL FREE ANALYZER FOR IN-VITRO AND IN-VIVO DETECTING THE SUSPICIOUS REGIONS TO CANCER

CROSS-REFERENCE TO RELATED APPLICATION

This application is a continuation-in-part of U.S. patent application Ser. No. 16/010,510, filed Jun. 17, 2018, and entitled "REAL-TIME AND LABEL FREE ANALYZER FOR IN-VITRO AND IN-VIVO DETECTING THE SUSPICIOUS REGIONS TO CANCER", which takes priority from U.S. Provisional Patent Application Ser. No. 62/522,115 filed on Jun. 20, 2017, and entitled "DIAGNOSIS OF CANCER TUMORS IN BIOPSY BREAST TISSUES" and U.S. Provisional Patent Application Ser. No. 62/563,673 filed on Sep. 27, 2017, and entitled "CANCER DIAGNOSTIC PROBE", both of which are incorporated herein by reference in their entirety.

SPONSORSHIP STATEMENT

This application has been sponsored by Iran Patent Office, which does not have any rights in this application.

TECHNICAL FIELD

The present disclosure generally relates to cancer diagnosis, and particularly, to a system, sensor, and method for diagnosing cancerous regions before and during surgery via a real-time and label free approach.

BACKGROUND

Glycolysis is the intracellular biochemical conversion of one molecule of glucose into two molecules of pyruvate, which can be used to attain cellular energy. With the assistance of sufficient oxygen, pyruvate could be converted by pyruvate dehydrogenase (PDH) into acetylCoA which is crucial in a metabolizing process to produce ATP in an oxidative way. A physiological concentration of pyruvate in human normal epithelial tissue has been reported to 0.7 mmol/g. Also the lactate-to-pyruvate ratio (L/P ratio) as a reflection of cell's redox state, illustrates the balance between NAD+ and NADH+H+, depending on the interconversion of lactate and pyruvate via lactate dehydrogenase (LDH). The L/P ratio in normal epithelial tissues is less than 20:1. Markers and assays have been developed to trace the LADH, P, or L/P in the patients' specimen as diagnostic or prognostic factors which reveal the interests on lactate based cancer research. Moreover some methods have been developed to trace pyruvate by electrochemical methods with the assistance of chemically labelled working electrodes. However, there is still no substitutive label free methods and/or devices to replace expensive, complicated, and late-responsive clinical methods and devices such as pathology assays.

Hence, there is a need for cost-effective, label free and real-time methods and devices, especially sensors and method to use thereof to detect cancer in suspicious regions especially during cancer surgery like mastectomy to remove involved regions with precise margins to reduce resection of normal sites.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

Various exemplary methods and devices are disclosed, and examples may include a method and probe for detect and monitor a cancerous tumor. According to one or more exemplary embodiments, the present disclosure is directed to a method for non-invasive detecting and tracing cancer. The exemplary method may include fabricating a probe including two reference electrodes, a working electrode located inside a first reference electrode of the two reference electrodes, and a counter electrode located inside a second reference electrode of the two reference electrodes, putting the probe on a part of skin adjacent to a target location inside a patient's body, inserting the two reference electrodes inside the target location through the part of skin, inserting the working electrode and the counter electrode into the target location by releasing the working electrode and the counter electrode through the two reference electrodes, recording a cyclic voltammetry (CV) response of hypoxia-related hydrogen peroxide ($H_2O_2$) release in the target location by applying a set of electrical potentials to the probe, measuring an oxidation current peak of the recorded CV response, and detecting a cancerous tumor at the target location by comparing the measured oxidation current peak with a set of reference values. In an exemplary implementation, the exemplary method may further include identifying the target location by acquiring a sonography image from the patient's body. In an exemplary embodiment, the working electrode may include a first needle including a first tip coated with a first layer of carbon nanotubes (CNTs), and the counter electrode may include a second needle including a second tip coated with a second layer of CNTs.

In an exemplary implementation, putting the probe on the part of skin adjacent to the target location inside the patient's body, inserting the two reference electrodes inside the target location trough the part of skin, and inserting the working electrode and the counter electrode into the target location may be done during sonography imaging.

In an exemplary implementation, applying the set of electrical potentials to the probe may include applying a sweeping range of electrical potentials between −1 V and 1 V to the working electrode. In an exemplary implementation, applying the set of electrical potentials to the probe may include applying the set of electrical potentials to the working electrode using a potentiostat device.

In an exemplary implementation, measuring the oxidation current peak of the recorded CV response may include measuring Hydrogen Peroxide ($H_2O_2$) oxidation within the target location.

In an exemplary implementation, detecting the cancerous tumor at the target location may include generating the set of reference values, comparing the measured oxidation current peak with the generated set of reference values, and detecting the cancerous tumor at exemplary target location if the measured oxidation current peak is in a range of the generated set of reference values associated with a plurality of cancerous samples. In an exemplary implementation, generating the set of reference values may include recording a set of CV responses from a plurality of samples using the exemplary probe, and measuring a respective set of oxidation current peaks of the recorded set of CV responses. In an exemplary embodiment, the plurality of samples may include a plurality of healthy samples and a plurality of cancerous samples.

In an exemplary implementation, fabricating the probe may include forming the working electrode and the counter electrode, placing the working electrode and the counter electrode inside respective hollow needles of the two reference electrodes, and attaching the two reference electrodes, the working electrode and the counter electrode to three respective pins of an electrical connector. In an exemplary implementation, forming the working electrode and the counter electrode may include coating two layers of silver (Ag) paste on tip of each of the first needle and the second needle, electrically isolating rest part of each of the first needle and the second needle, and depositing CNTs on the two layers of Ag paste by electrostatically depositing CNTs powder on the two layers of Ag paste.

In an exemplary implementation, coating two layers of silver (Ag) paste on tip of each of the first needle and the second needle may include coating a first layer of Ag paste on the first tip of the first needle, and coating a second layer of Ag paste on the second tip of the second needle. In an exemplary implementation, depositing CNTs on the two layers of Ag paste by electrostatically depositing CNTs powder on the two layers of Ag paste may include depositing the first layer of CNTs on the first layer of Ag paste, and depositing the second layer of CNTs on the second layer of Ag paste.

In an exemplary implementation, depositing CNTs on the two layers of Ag paste may include depositing vertically aligned multi-walled carbon nanotubes (VAMWCNTs) on the two layers of Ag paste. In an exemplary implementation, depositing CNTs on the two layers of Ag paste may include connecting CNTs powder to a positive pole of an electrostatic potential generator, connecting the first needle with Ag paste coated on the first tip and the second needle with Ag paste coated on the second tip to a negative pole of the electrostatic potential generator, and electrostatically grasping CNTs powder on the two layers of Ag paste by moving the first needle with Ag paste coated on the first tip and the second needle with Ag paste coated on the second tip alongside the positive pole of the electrostatic potential generator.

In an exemplary implementation, inserting the two reference electrodes inside the target location through the part of skin may include inserting the two reference electrodes inside the target location within a depth up to 10 cm from an outside skin.

According to one or more exemplary embodiments, the present disclosure is directed to a probe for non-invasive detecting and tracing cancer. The exemplary probe may include a sensing part and a holing member. In an exemplary embodiment, the sensing part may include two reference electrodes including a first hollow needle and a second hollow needle, a working electrode located inside the first hollow needle, and a counter electrode located inside the second hollow needle. In an exemplary embodiment, the working electrode may include a first needle including a first tip coated with a first layer of carbon nanotubes (CNTs). The counter electrode may include a second needle including a second tip coated with a second layer of CNTs.

In an exemplary embodiment, the sensing part may be attached to a first end of the holding member. The holding member may include a button at a second end of the holding member. The button may be configured to push the working electrode and the counter electrode outside the two reference electrodes, and pull the working electrode and the counter electrode inside the two reference electrodes.

In an exemplary embodiment, each of the first layer of CNTs and the second layer of CNTs may include a layer of vertically aligned multi-walled carbon nanotubes (VAMWCNTs). In an exemplary embodiment, the VAMWCNTs may include VAMWCNTs with a length of between 0.5 μm and 10 μm and a diameter of between 20 nm and 100 nm. In an exemplary embodiment, each of the first hollow needle and the second hollow needle may have a diameter twice a diameter of each of the working electrode and the counter electrode. In an exemplary embodiment, each of the two reference electrodes, the working electrode, and the counter electrode may include a biocompatible steel needle with a diameter between 100 μm and 1 cm and a length between 0.1 cm and 10 cm. In an exemplary embodiment, the two reference electrodes may be fixed apart from each other with a distance between 1 mm and 5 mm. In an exemplary embodiment, each of the first tip and the second tip may have a length from one end of each of the respective first needle and second needle between 0.5 mm and 5 mm.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
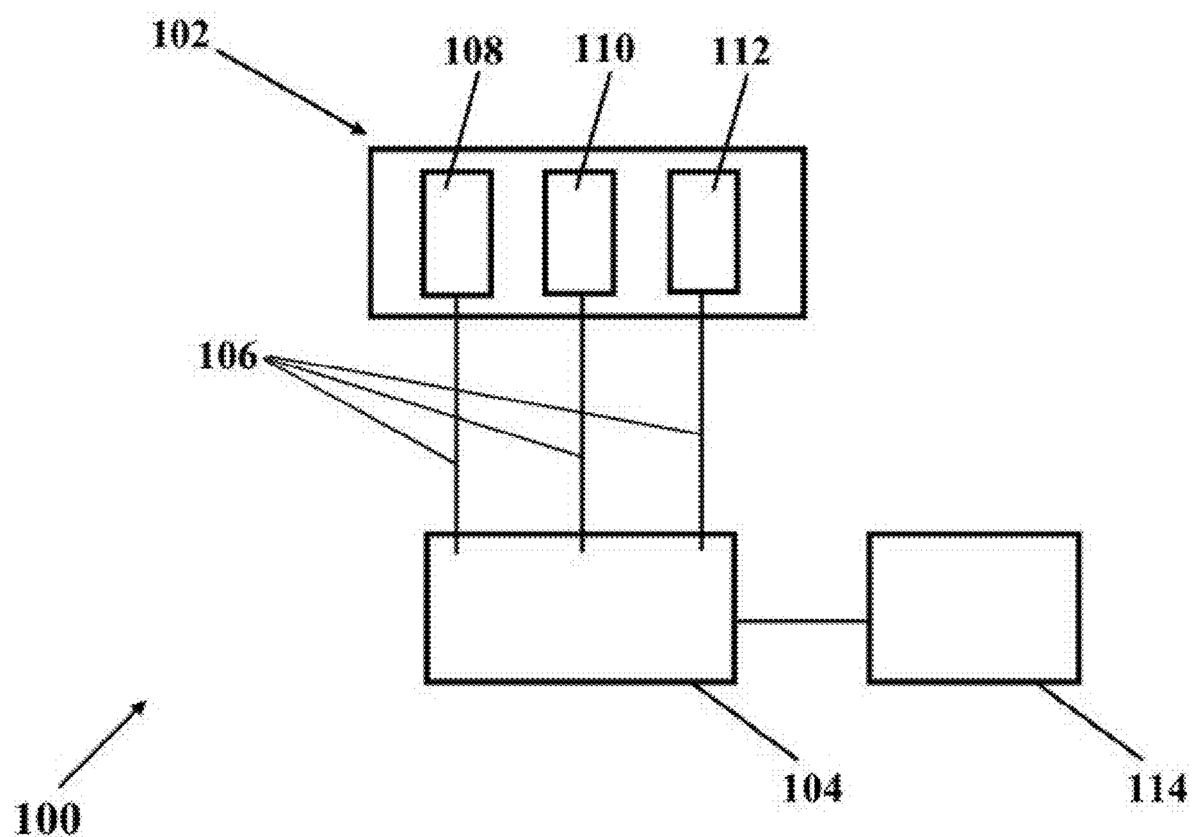
FIG. 1A illustrates a schematic view of an exemplary electrochemical system for cancer diagnosis, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

A number of current methods utilize lactate and/or pyruvate as cancer markers. However, herein the oxidation of Hydrogen Peroxide ($H_2O_2$) molecules measured by carbon nanotubes (CNTs) based electrodes is utilized to detect cancer and especially distinguish cancerous regions from healthy regions in a suspicious tissue. The main consequence of pyruvate formation from lactate is release of $H_2O_2$ molecules as the main byproduct of hypoxia glycolysis. An abnormal redox state appears in cancer cells based on modulation of hypoxia with increased pyruvate concentration and lactate-to-pyruvate ratio (L/P ratio) which results in increasing the concentration of $H_2O_2$ in interstitial fluid (stroma). So, determination of $H_2O_2$ molecules would be an indication for the presence of cancer cells in a tissue. As $H_2O_2$ is an active and non-stable molecule it would turn to $O_2$, $H^+$ and release electrons which are great target charges for electrochemical sensation.

Herein, an electrochemical approach based on multi-walled carbon nanotubes (MWCNTs) electrodes is disclosed for fast tracking of hypoxia glycolysis in the interstitial fluid of biopsied tissues suspicious to cancer, such as breast tissues. Electrochemical reduction of $H_2O_2$ molecules, produced in lactate to pyruvate transformation, on the electrodes of disclosed system may present a significant quantitate response signal in correlation with the presence of cancer cells in a suspicious sample. Here, a cancer diagnostic probe (CDP) based on vertically aligned multi-walled carbon nanotubes (VAMWCNTs) arrays as sensing electrode with direct and selective electron transfer abilities in interaction with $H_2O_2$ may be utilized.

Disclosed herein may include a label free method for diagnosis of the presence of cancer in suspicious regions based on determination of the hypoxia glycolysis in a quantitative manner. The method may be based on measuring the oxidative currents released during glycolysis from the tissue. A matched diagram between an electrochemical response measured from a suspicious sample and cancerous state curves may be utilized for a final diagnostic result. Over expression of glycolysis assisted mRNAs in cancerous samples may be observed as an indicator of a presence of cancer in a sample. Exemplary method may be applied as an alternative for frozen pathology during the surgery with faster and more precise efficiency. Furthermore, a label free system including an electrochemical sensor with integrated three CNT based electrodes is disclosed for tracking hypoxia glycolysis via detecting electrochemical reduction of $H_2O_2$ molecules, which may be produced in Lactate to pyruvate transformation in cancer cells. Exemplary simple and label free electrochemical assay may also be used for measuring the drug resistance of the tumors as a pre therapeutic prediction (as a new prognostic factor) to increase the survival rate in future.

In some implementations, exemplary electrochemical sensor may include an integrated sensor on the needles, named herein as a cancer diagnostic probe (CDP). Exemplary CDP may be fabricated and utilized in real-time on the suspicious regions to cancer before and during surgery in patients (In vivo). The domain of suspicious regions with a resolution of about 3 mm may be detected using exemplary method and CDP. The significant specification of CDP rather than recently reported real-time diagnostic methods, such as mass-spec, may allow the CDP to track the cancer involved regions before surgery by squeezing exemplary CDP to suspicious regions through the skin with the tracking resolution of 3 mm. In conventional diagnostic protocols, to precisely remove the cancer regions during surgery, a frozen sample from each suspicious region may need to be sent for pathologists. The pathology results may be available after about 15 minutes with the false negative response ratio of about 10%. Whereas, a cancer region may be distinguished in-situ utilizing exemplary CDP in less than about 10 seconds or even instantaneously before or during surgery and without any need for resecting and freezing a sample from a patient. The diagnostic information obtained by exemplary CDP may be used to detect cancer in marginally suspicious regions with rare distributions of cancer cells filtrated between normal stroma in less than about 20 seconds during the surgery or biopsy of live animal or human models without any requirement of tissue resection and preparation for frozen pathology. Exemplary CDP may be also utilized to detect an accurate location of cancer involved regions before surgery in superficial tumors.

Moreover, exemplary sensor may include a CNT based electrochemical chip for in vitro cancer diagnosis in suspicious samples. Exemplary CNT based electrochemical chip may include an array of electrodes of VAMWCNTs used in electrochemical assays. Both liquid and solid suspicious samples may be analyzed using exemplary CNT based electrochemical chip to detect a cancer presence within the suspicious samples.

FIG. 1A shows a schematic view of an electrochemical system 100 for cancer diagnosis, consistent with one or more exemplary embodiments of the present disclosure. Exemplary electrochemical system 100 may include an exemplary sensor 102, an electrochemical stimulator-analyzer 104, and an array of electrically conductive connectors 106. Exemplary sensor 102 may be configured to put in contact with a suspicious sample for cancer. Exemplary sensor 102 may include an integrated three-electrodes array, which may include the working electrode 108, the counter electrode 110, and the reference electrode 112. Each of the working electrode 108, the counter electrode 110 and the reference electrode 112 may include an array of vertically aligned multi-walled carbon nanotubes (VAMWCNTs). The electrochemical stimulator-analyzer 104 may be configured to measure electrochemical responses from the working electrode 108 and sensor 102 may be connected to the electrochemical stimulator-analyzer 104 via the array of electrically conductive connectors 106.

In an exemplary implementation, exemplary electrochemical system 100 may be configured to detect a cancerous state via measuring $H_2O_2$ during hypoxia glycolysis in the suspicious sample for cancer. Exemplary electrochemical system 100 may be utilized by an exemplary method for cancer diagnosis described herein below.

In an exemplary embodiment, electrochemical stimulator-analyzer 104 may include a device that may be capable of measuring cyclic voltammetry (CV) based diagrams. In an exemplary embodiment, electrochemical stimulator-analyzer 104 may include a potentiostat.

In an exemplary implementation, electrochemical system 100 may further include a processor 114 that may be utilized for recording and analyzing electrochemical measurements that may be measured by electrochemical stimulator-analyzer 104. Processor 114 may also be used for controlling electrochemical stimulations that may be carried out by electrochemical stimulator-analyzer 104. In an exemplary embodiment, processor 114 may include an EVIUM readout system.

Figure 1B:
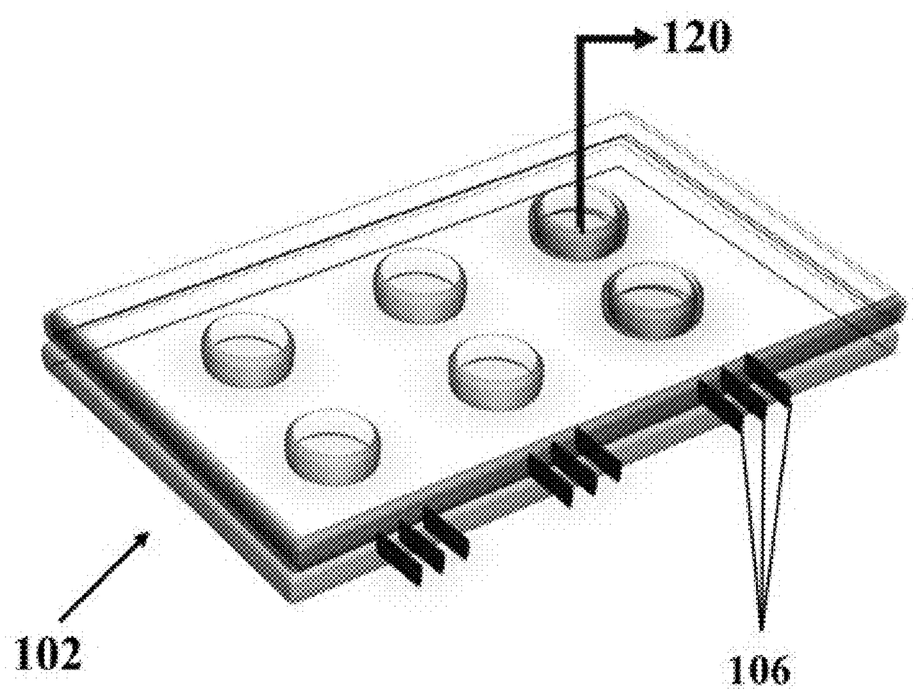
FIG. 1B illustrates a schematic view of an exemplary CNT based electrochemical chip, consistent with one or more exemplary embodiments of the present disclosure.
Figure 1C:
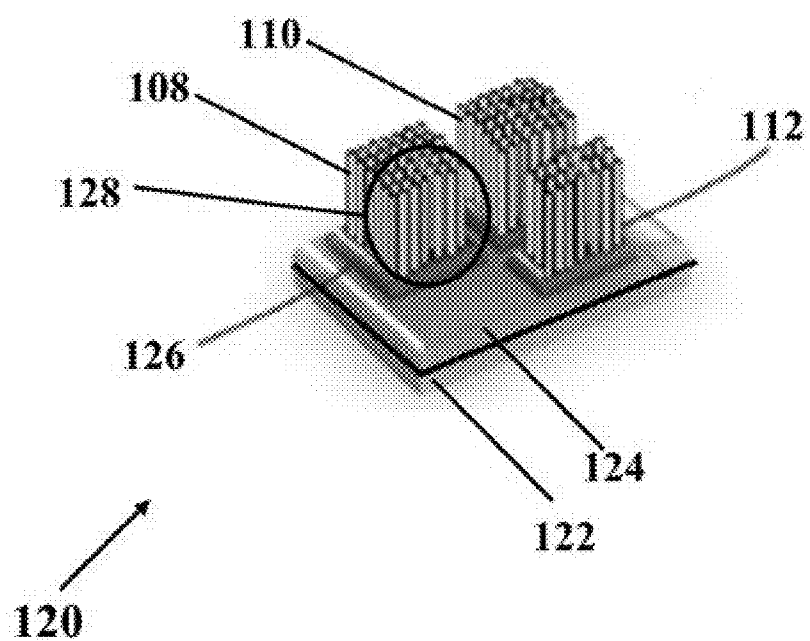
FIG. 1C illustrates a schematic view of an exemplary sensing well, consistent with one or more exemplary embodiments of the present disclosure.

In an exemplary implementation, sensor 102 may include a CNT based electrochemical chip that may be configured to conduct in vitro cancer diagnosis assays. FIG. 1B shows a schematic view of exemplary CNT based electrochemical chip 102, consistent with one or more exemplary embodiments of the present disclosure. Exemplary CNT based electrochemical chip 102 may include at least one sensing well 120 and one array of electrically conductive connectors 106. FIG. 1C shows a schematic view of exemplary sensing well 120, consistent with one or more exemplary embodiments of the present disclosure. Each sensing well 120 may include a substrate 122, a passivation layer 124 that may be grown on substrate 122, a catalyst layer 126 that may be coated or deposited and subsequently patterned on the passivation layer 124, and three arrays of VAMWCNTs that may be grown on the catalyst layer 126. Three arrays of VAMWCNTs may include the working electrode 108, the counter electrode 110, and the reference electrode 112.

In an exemplary embodiment, substrate 122 may include a silicon chip or wafer. Passivation layer 124 may include a layer of $SiO_2$ with a thickness of less than about 500 nm that may be grown by wet oxidation furnace on the surface of on substrate 122. Catalyst layer 126 may include a layer of Nickel (Ni) with a thickness of less than about 10 nm that may be coated on passivation layer 124 by an E-beam evaporation system at a temperature of about 120° C. with depositing rate of about 0.1 Angstroms/s. Three arrays of VAMWCNTs (the working electrode 108, the counter electrode 110, and the reference electrode 112) may be grown on catalyst layer 126 using a direct current plasma enhanced chemical vapor deposition (DC-PECVD) system. The growth process of VAMWCNTs may include three steps of firstly, annealing at a temperature of about 680° C. in an $H_2$ environment with a flow rate of about 35 standard cubic centimeters per minute (sccm) for about 30 minutes; secondly, graining, including plasma hydrogenation of surface for about 5 minutes with the intensity of about 5.5 $W \cdot cm^{-2}$ that may result in the catalyst layer 126 graining and formation of Ni nano-sized islands, and finally, growth of VAMWCNTs by introducing a plasma of $C_2H_2$ and $H_2$ mixture with flow rates of about 5 sccm and about 35 sccm to the chamber for about 15 minutes. Each of the VAMWCNTs may have a length between about 0.5 μm and about 5 μm and a diameter between about 20 nm and about 100 nm. The working electrode 108 may be grown on an area of about 1 cmxl cm, the counter electrode 110 may be grown on an area of about 1 cm×1 cm, and the reference electrode 112 may be grown on an area of about 0.5 cm×0.5 cm.

Figure 1D:
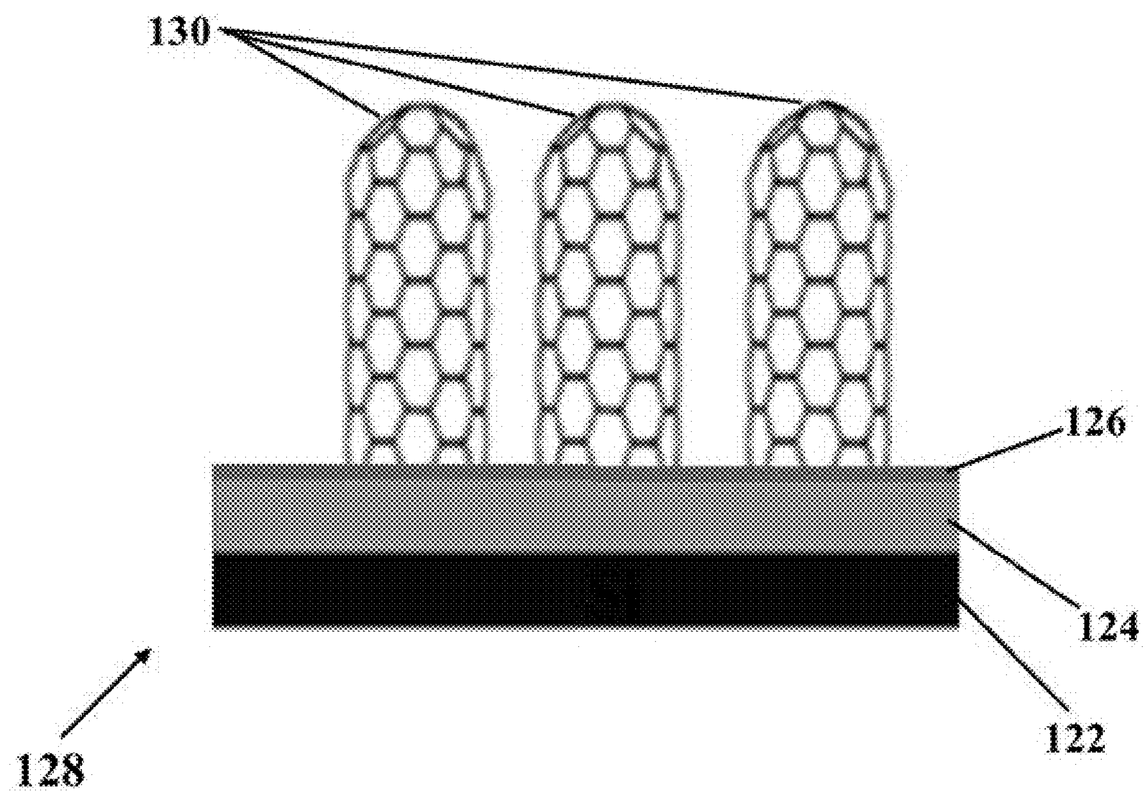
FIG. 1D illustrates a schematic view of an exemplary magnified portion of exemplary working electrode within exemplary sensing well of FIG. 1C, consistent with one or more exemplary embodiments of the present disclosure.

FIG. 1D shows a schematic view of an exemplary magnified portion 128 of exemplary working electrode 108 within exemplary sensing well 120 of FIG. 1C, consistent with one or more exemplary embodiments of the present disclosure. Exemplary VAMWCNTs 130 of an array of VAMWCNTs of working electrode 108 may be grown vertically on catalyst layer 126. Catalyst layer 126 may be coated or deposited and subsequently patterned on the passivation layer 124, where passivation layer 124 may be grown on substrate 122.

Figure 1E:
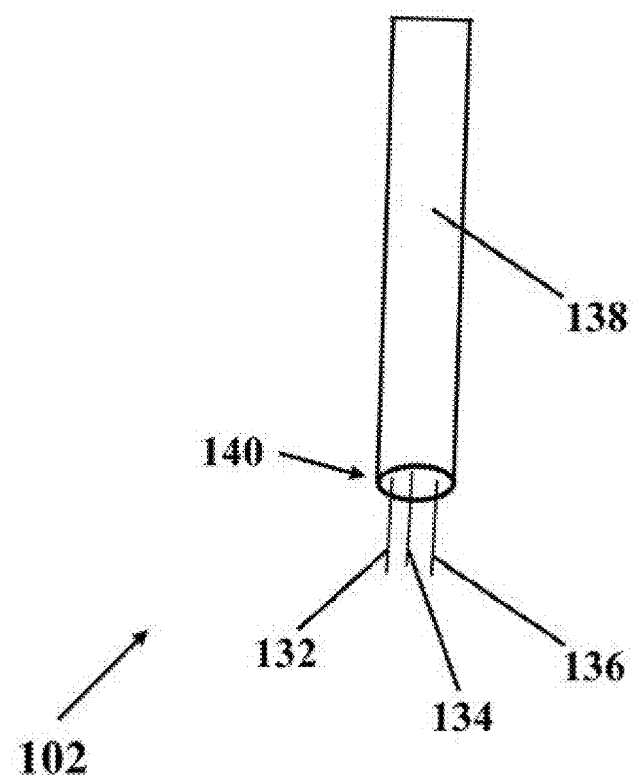
FIG. 1E illustrates a schematic view of an exemplary cancer diagnosis probe (CDP), consistent with one or more exemplary embodiments of the present disclosure.

In an exemplary implementation, sensor 102 may include a cancer diagnosis probe (CDP) that may be configured to conduct in vivo cancer diagnosis assays. FIG. 1E shows a schematic view of exemplary cancer diagnosis probe (CDP) 102, consistent with one or more exemplary embodiments of the present disclosure. Exemplary cancer diagnosis probe (CDP) may include three needle electrodes 132, 134, and 136 as exemplary implementations of the working electrode 108, the counter electrode 110, and the reference electrode 112, respectively. Moreover, CDP 102 may include a holding member 138 that may be configured to hold three needle electrodes 132, 134, and 136. Three needle electrodes 132, 134, and 136 may be fixed on one end 140 of the holding member 138.

Figure 1F:
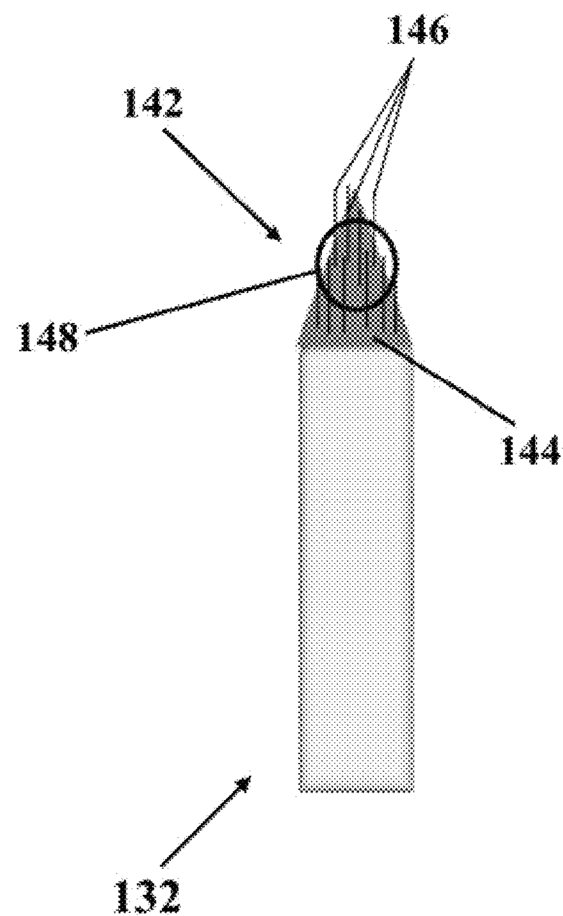
FIG. 1F illustrates a schematic view of an exemplary needle electrode of exemplary CDP corresponding to the working electrode, consistent with one or more exemplary embodiments of the present disclosure.

FIG. 1F shows a schematic view of an exemplary needle electrode 132 corresponding to the working electrode 108, consistent with one or more exemplary embodiments of the present disclosure. Referring to FIG. 1F, each needle electrode of three needles electrodes 132, 134, and 138 may include a tip 142. Each needle electrode of the three needles electrodes 132, 134, and 136 may include a catalyst layer 144 that may be deposited on tips 142 of three needles electrodes 132, 134, and 136 and an array of VAMWCNTs 146 that may be grown on catalyst layer 144 on tip 142 of each needle electrode of three needles electrodes 132, 134, and 138.

In an exemplary embodiment, each needle electrode of three needles electrodes 132, 134, and 138 may include a steel needle with a diameter between about 100 μm and about 200 μm, and a length between about 0.1 cm and about 1 cm. Three needle electrodes 132, 134, and 138 may be fixed on the end 140 of the holding member 138 apart from each other with a distance (interspace) between each other in a range of about 1 mm to about 5 mm.

In an exemplary embodiment, catalyst layer 144 may include a layer of Nickel (Ni) with a thickness of less than about 10 nm that may be coated on tip 142 of each needle electrode by an E-beam evaporation system at a temperature of about 120° C. with a depositing rate of about 0.1 Angstroms/s. Three arrays of VAMWCNTs (the working electrode 108, the counter electrode 110, and the reference electrode 112) may be grown on catalyst layer 144 using a direct current plasma enhanced chemical vapor deposition (DC-PECVD) system as described herein above.

Figure 1G:
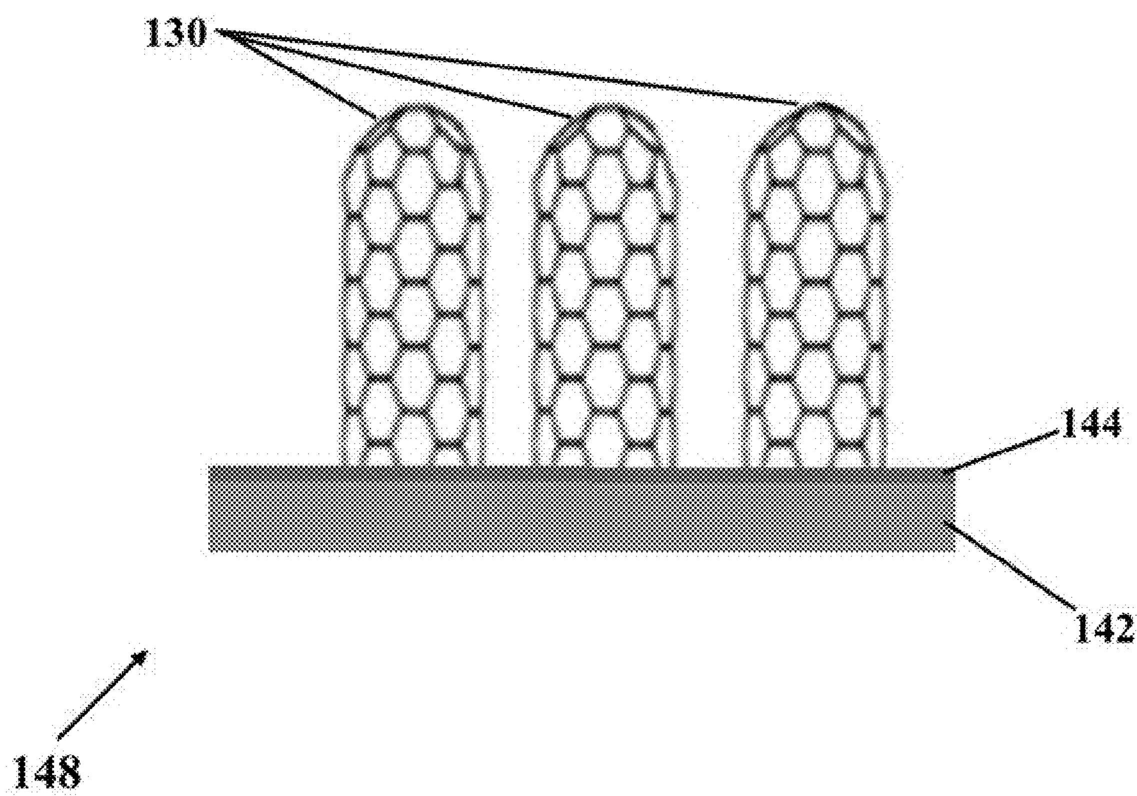
FIG. 1G illustrates a schematic view of an exemplary magnified portion of a tip of exemplary needle electrode of FIG. 1C, consistent with one or more exemplary embodiments of the present disclosure.

FIG. 1G shows a schematic view of an exemplary magnified portion 148 of tip 142 of exemplary needle electrode 132 shown in FIG. 1F, consistent with one or more exemplary embodiments of the present disclosure. Exemplary VAMWCNTs 130 of an array of VAMWCNTs 146 may be grown vertically on catalyst layer 144. Catalyst layer 144 may be coated or deposited on a surface of tip 142.

Figure 2A:
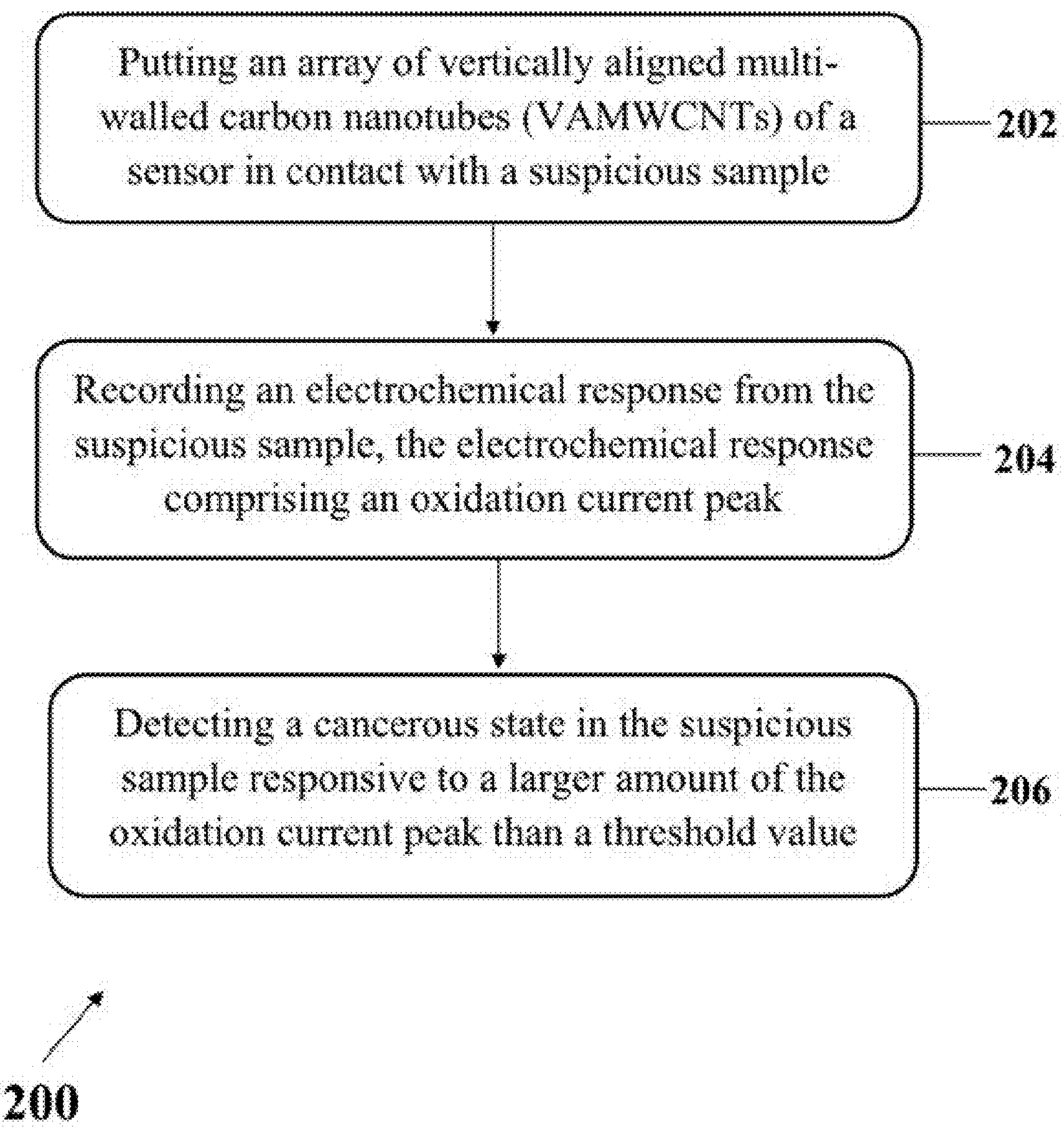
FIG. 2A illustrates an exemplary implementation of a method for cancer diagnosis, consistent with one or more exemplary embodiments of the present disclosure.

In another aspect of the present disclosure, a method for cancer diagnosis is disclosed. FIG. 2A shows an exemplary implementation of method 200 for cancer diagnosis, consistent with one or more exemplary embodiments of the present disclosure. Method 200 may include putting an array of vertically aligned multi-walled carbon nanotubes (VAMWCNTs) of a sensor in contact with a suspicious sample (step 202), recording an electrochemical response from the suspicious sample, where the electrochemical response may include an oxidation current peak (step 204), and detecting a cancerous state in the suspicious sample responsive to a larger amount of the oxidation current peak than a threshold value (step 206). The sensor may be similar to exemplary sensor 102 described hereinabove.

Step 202 may include putting the array of vertically aligned multi-walled carbon nanotubes (VAMWCNTs) of the sensor in contact with the suspicious sample. In an exemplary implementation, putting the array of VAMWCNTs of the sensor in contact with the suspicious sample may include one of dropping the suspicious sample onto the sensor, placing the suspicious sample onto the sensor, squeezing the sensor into the suspicious sample, inserting the sensor into the suspicious sample, and combinations thereof.

In an exemplary embodiment, the suspicious sample may include one of a liquid suspicious sample, a solid suspicious sample, and combinations thereof. In an exemplary embodiment, the suspicious sample may include one of a plurality of cell lines, a biopsied sample from a human or animal body, a removed sample from a human or animal body by surgery, a portion of a living tissue in a human or animal body, and a portion of a living tissue in a human or animal body during surgery.

In an exemplary implementation, the sensor may be similar to sensor 102 and may include a substrate, a catalyst layer, and three arrays of vertically aligned multi-walled carbon nanotubes (VAMWCNTs) grown on the catalyst layer. Three arrays of VAMWCNTs may include a working electrode that may include a first array of VAMWCNTs, a reference electrode that may include a second array of VAMWCNTs, and a counter electrode that may include a third array of VAMWCNTs. In an exemplary implementation, the sensor may further include a passivation layer between the substrate and the catalyst layer.

In an exemplary implementation, the sensor may include one of a CNT based electrochemical chip similar to exemplary CNT based electrochemical chip 102 shown in FIG. 1B, and a cancer diagnosis probe (CDP) similar to exemplary CDP 102 shown in FIG. 1E. The substrate of the cancer CDP may include three needles, where each needle of the three needles may be coated by an array of VAMWCNTs of the three arrays of VAMWCNTs. In an exemplary implementation, the sensor may include exemplary sensor 102 as shown schematically in FIGS. 1A, 1B, and 1E.

Figure 2B:
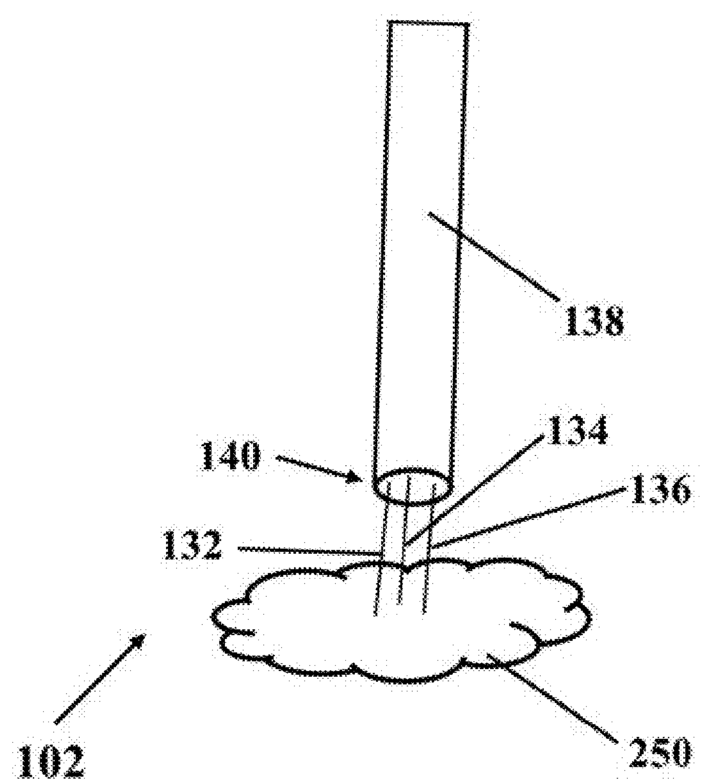
FIG. 2B illustrates a schematic implementation of putting the array of vertically aligned multi-walled carbon nanotubes (VAMWCNTs) grown on tip of each needle electrode of three needles electrodes of exemplary CDP in contact with exemplary suspicious sample, consistent with one or more exemplary embodiments of the present disclosure.

FIG. 2B shows a schematic implementation of step 202 that may include putting the array of vertically aligned multi-walled carbon nanotubes (VAMWCNTs) grown on tip of each needle electrode of three needles electrodes 132, 134, and 138 of exemplary cancer diagnosis probe (CDP) 102 in contact with exemplary suspicious sample 250, consistent with one or more exemplary embodiments of the present disclosure. Step 102 may include inserting or squeezing exemplary cancer diagnosis probe (CDP) 102 in exemplary suspicious sample 250.

In an exemplary implementation, putting the array of VAMWCNTs of exemplary sensor 102 in contact with the suspicious sample may take place temporarily or over a time duration of less than 1 seconds for a real-time cancer diagnosis case. In an exemplary embodiment, putting the array of VAMWCNTs of exemplary sensor 102 in contact with the suspicious sample may take place temporarily or over a time duration of less than 1 seconds for in vivo or in vitro cancer diagnosis using exemplary sensor which may be an exemplary CDP or exemplary CNT based electrochemical chip. In an exemplary embodiment, putting the array of VAMWCNTs of exemplary sensor 102 in contact with the suspicious sample may be for a time duration of about 12 hours or more for in vitro cancer diagnosis cases with high levels of accuracy utilizing exemplary CNT based electrochemical chip 102. In an exemplary embodiment, putting the array of VAMWCNTs of exemplary sensor 102 in contact with the suspicious sample may be carried out in a time duration of about 0.1 seconds to about 24 hours.

Step 204 may include recording the electrochemical response from the suspicious sample, where the electrochemical response may include an oxidation current peak. In an exemplary embodiment, the electrochemical response may include a cyclic voltammetry (CV) diagram of hypoxic glycolysis chemical reaction in biological cells within the suspicious sample. In an exemplary embodiment, the electrochemical response may include a cyclic voltammetry (CV) diagram of $H_2O_2$ related oxidation/reduction chemical reaction in biological cells within the suspicious sample. The concentration of $H_2O_2$ may be in correlation with the hypoxia glycolysis occurred in tumor cells. In an exemplary embodiment, the electrochemical response may include a cyclic voltammetry (CV) diagram of $H_2O_2$ oxidation that may be electrically sensed by VAMWCNTs in biological cells within the suspicious sample. In an exemplary embodiment, the electrochemical response may include an oxidation current peak of exemplary CV diagram of hypoxic glycolysis chemical reaction in biological cells within a suspicious sample.

In an exemplary implementation, recording the electrochemical response from the suspicious sample (step 204) may include connecting the sensor to an electrochemical stimulator-analyzer, applying an electrical voltage on the sensor using the electrochemical stimulator-analyzer, and measuring the electrochemical response from the suspicious sample using the electrochemical stimulator-analyzer. In an exemplary embodiment, the electrochemical stimulator-analyzer may include a potentiostat.

Step 206 may include detecting the cancerous state in the suspicious sample responsive to a larger amount of the oxidation current peak than a threshold value. In an exemplary embodiment, the threshold value may include an oxidation current peak of about 700 μA or more when a time duration of putting the array of vertically aligned multi-walled carbon nanotubes (VAMWCNTs) of the sensor in contact with the suspicious sample (step 202) may be more than about 12 hours. In an exemplary embodiment, the threshold value may include an oxidation current peak of about 80 μA or more when a time duration of putting the array of vertically aligned multi-walled carbon nanotubes (VAMWCNTs) of the sensor in contact with the suspicious sample (step 202) may be about 5 seconds or less.

Figure 2C:
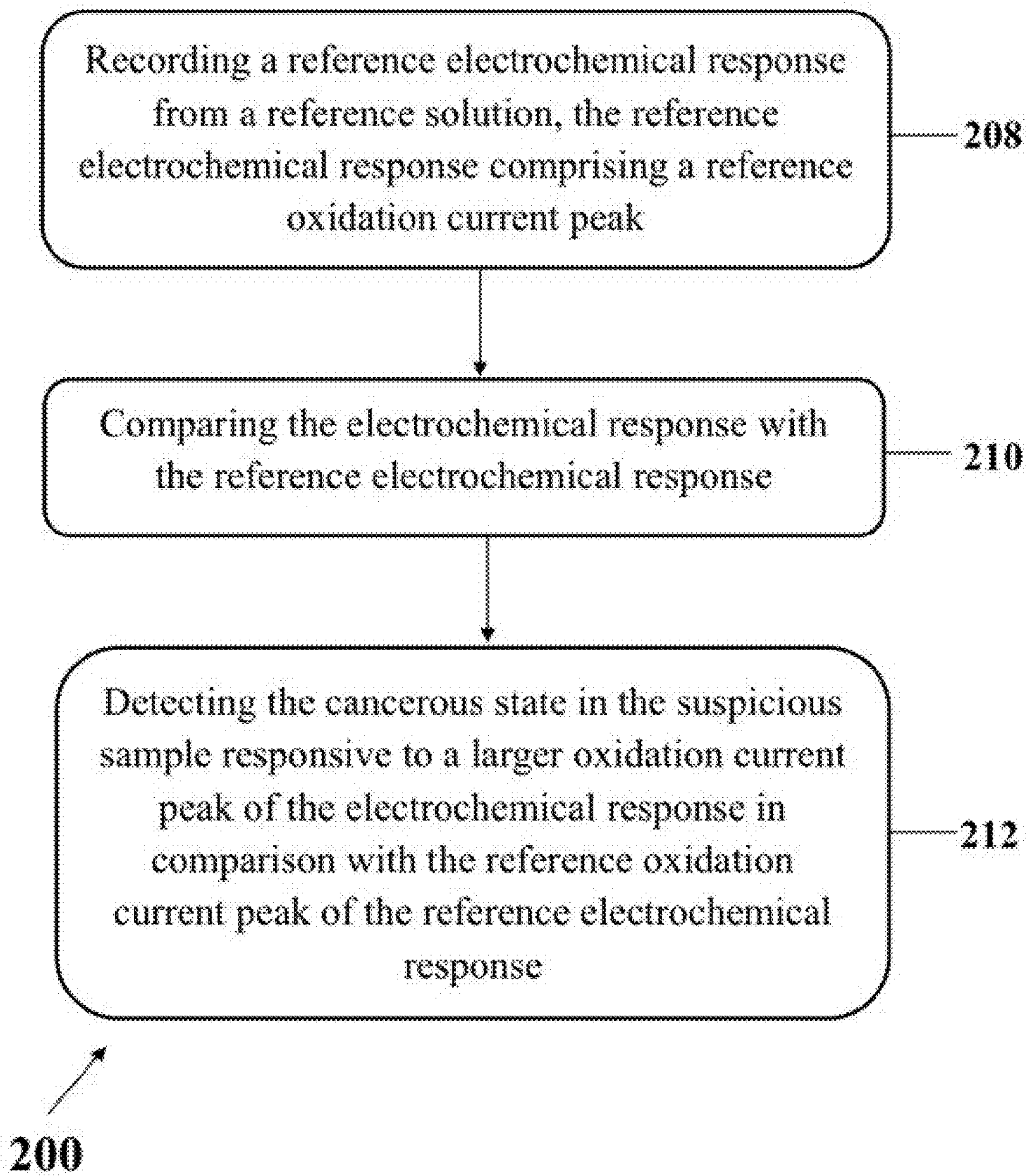
FIG. 2C illustrates an implementation of detecting the cancerous state in the suspicious sample, consistent with one or more exemplary embodiments of the present disclosure.

FIG. 2C shows an implementation of detecting the cancerous state in the suspicious sample (step 206), consistent with one or more exemplary embodiments of the present disclosure. Detecting the cancerous state in the suspicious sample (step 206) may include recording a reference electrochemical response from a reference solution, where the reference electrochemical response may include a reference oxidation current peak (step 208), comparing the electrochemical response with the reference electrochemical response (step 210), and detecting the cancerous state in the suspicious sample responsive to a larger oxidation current peak of the electrochemical response in comparison with the reference oxidation current peak (step 212). In an exemplary embodiment, the reference solution may include a lactate solution with a lactate concentration of about 0.05 mM or more.

Figure 3A:
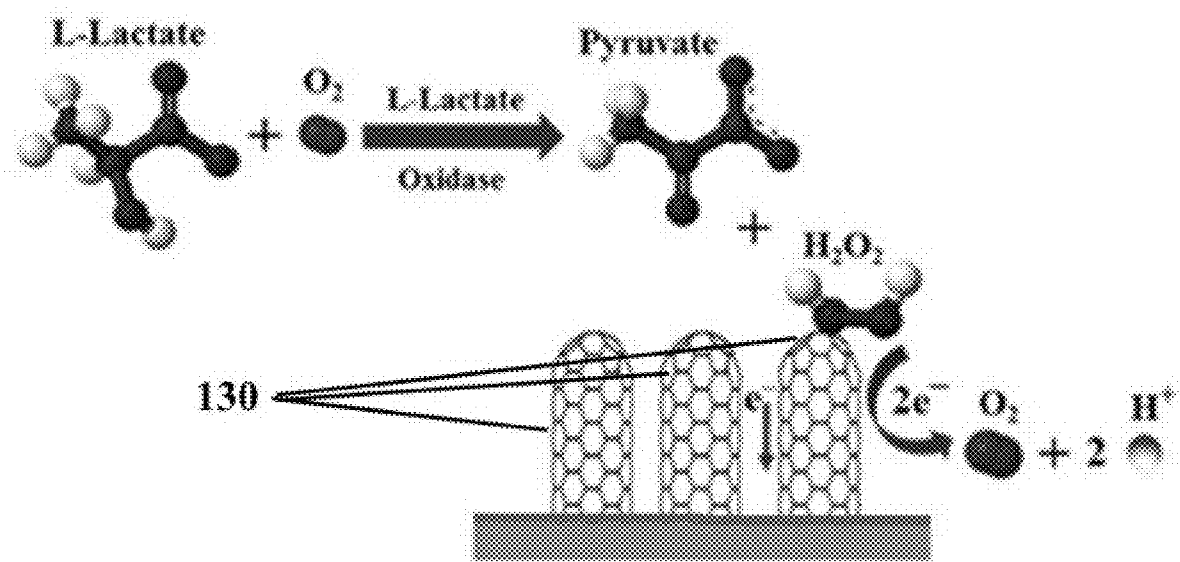
FIG. 3A illustrates a schematic view of exemplary electrochemical reactions involved on sensor including exemplary VAMWCNTs as shown in FIGS. 1D and 1G, consistent with one or more exemplary embodiments of the present disclosure.

In an exemplary implementation, electrochemical system 100 may be utilized for cancer diagnosis via exemplary method 200. FIG. 3A shows a schematic view of exemplary electrochemical reactions involved on sensor 102 including exemplary VAMWCNTs 130 as shown in FIGS. 1D and 1G, consistent with one or more exemplary embodiments of the present disclosure. Presence of $H_2O_2$ active molecule released during hypoxia glycolysis in a suspicious sample may be the main trigger of the electrochemical reactions. Hence, the chemical reaction occurring on the working electrode 108 including VAMWCNTs 130 may include:

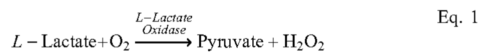

$$L-\text{Lactate}+O_2 \xrightarrow[\text{Oxidase}]{L\text{-Lactate}} \text{Pyruvate} + H_2O_2 \quad \text{Eq. 1}$$

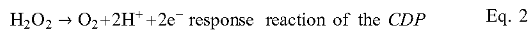

$$H_2O_2 \rightarrow O_2+2H^+ +2e^- \text{ response reaction of the } CDP \quad \text{Eq. 2}$$

When the hypoxia glycolysis (Eq. 2) is activated (the concentration of 02 is less than 5%) in cancer cells, increased reactive oxygen species (ROS) generated by mitochondria, would significantly enhance the cathodic peak of an electrochemical response measured from the suspicious sample which could be sharply detected by VAMWCNTs 130 electrodes. It may be known that the lactate released by hypoxic tumor cells during their glycolysis may not be discharged as a waste product, but may be taken up by oxygenated tumor cells as energy fuel in which Lactate is converted to pyruvate and $H_2O_2$ by LDH-B and then enters the mitochondria for OXPHOS to generate ATP. Similar to this process, the lactate released from hypoxic tumor cells may be used herein in electrochemical assay to trace the concentration of lactate due to the intensity of the $H_2O_2$ produced during LADH (Eq. 1) and released electrons due to the intensity of $H_2O_2$ oxidation reaction (Eq. 2).

Figure 3B:
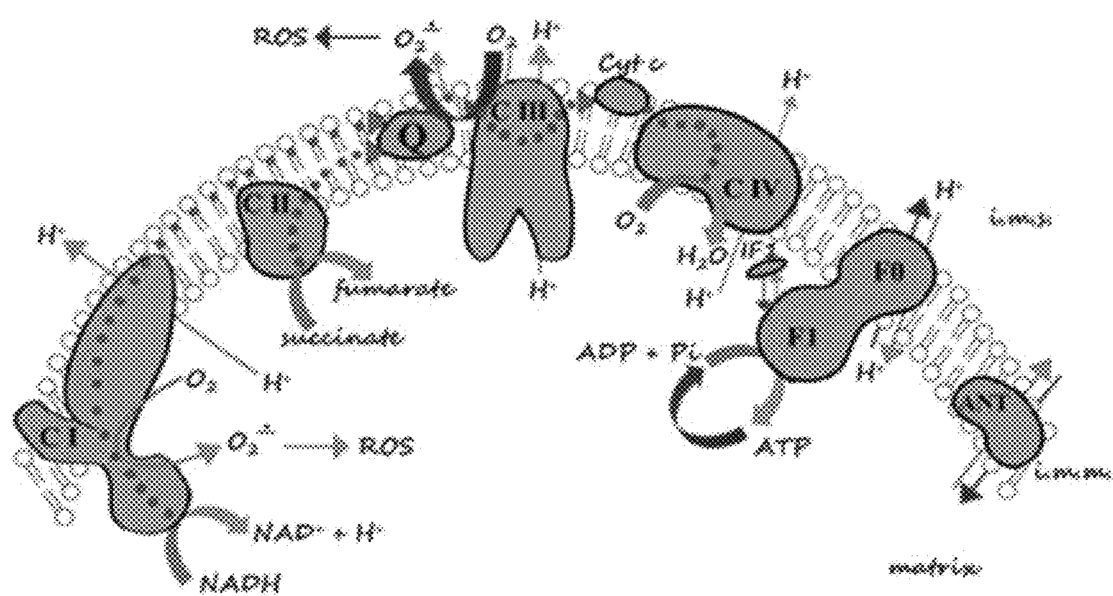
FIG. 3B illustrates a schematic overview of mitochondrial electron and proton fluxes in hypoxia, consistent with one or more exemplary embodiments of the present disclosure.

FIG. 3B shows a schematic overview of mitochondrial electron and proton fluxes in hypoxia, consistent with one or more exemplary embodiments of the present disclosure. During normaxia, electrons released from reduced cofactors (NADH and FADH2), flow through the redox centers of the respiratory chain (r.c.) to molecular oxygen (dotted lines), to which a proton flux from the mitochondrial matrix to the intermembrane space is coupled (grey arrows). Protons then flow back to the matrix through the F0 sector of the ATP synthase complex, driving ATP synthesis. ATP is carried to the cell cytosol by the adenine nucleotide translocator (grey arrows). Under moderate to severe hypoxia, electrons escape the r.c. redox centers and reduce molecular oxygen to the superoxide anion radical before reaching the cytochrome c (black arrows). Under these conditions, to maintain an appropriate $\Delta\psi$m, ATP produced by cytosolic glycolysis enters the mitochondria where it is hydrolyzed by the F1F0 ATPase with extrusion of protons from the mitochondrial matrix (black arrows). So, the mechanism of $H_2O_2$ detection by the VAMWCNTs 130 electrodes in hypoxia glycolysis may be based on released ion species during reduction of $NADH^+$, generation of ROS and production of superoxide anion radical by reducing molecular oxygen before reaching to cytochrome c. The amount of released charged species and increased current transferred by VAMWCNTs 130 electrodes may be correlated with the concentration of the lactate and subsequently $H_2O_2$ which resulted in ROS generated during hypoxia glycolysis.

Exemplary methods and devices herein are further directed to real-time non-invasive detecting and tracing cancer in a patient's body. An exemplary method and an exemplary probe is disclosed herein for real-time and precise, detection of and tracing of cancerous tumors. An exemplary method may be utilized as a substitutive technique for biopsy and its complementary histopathological and immunohistochemical procedures to obtain distinguishing information about a suspicious area in a patient's body or to monitor changes and effects on a tumor during cancer therapy treatments, such as chemotherapy, radiotherapy, etc. Utilizing an exemplary method and exemplary probe may lead to overcoming significant limitations associated with biopsy procedures, such as core needle biopsy (CNB). Unlike the biopsy procedures, an exemplary method and an exemplary probe may be used for painless, accurate, and real-time in-vivo detection of a tumor or monitoring of a tumor's situation or condition. In an exemplary embodiment, "monitoring of a tumor's situations or condition" may refer to at least one of evaluating therapeutic effects on a cancerous tumor after cancer treatments, such as chemotherapy/radiotherapy therapies, keep tracking of margins and size of a cancerous tumor over a time period, and tracing changes in properties and conditions of cancerous tumors. The exemplary method and probe may allow for a non-invasive procedure to be conducted, that is, it may be utilized in combination with sonography guide while imaging form a patient's body without any need to conduct an invasive procedure, such as having to conduct a surgery and/or resect a sample from living tissues.

Figure 18A:
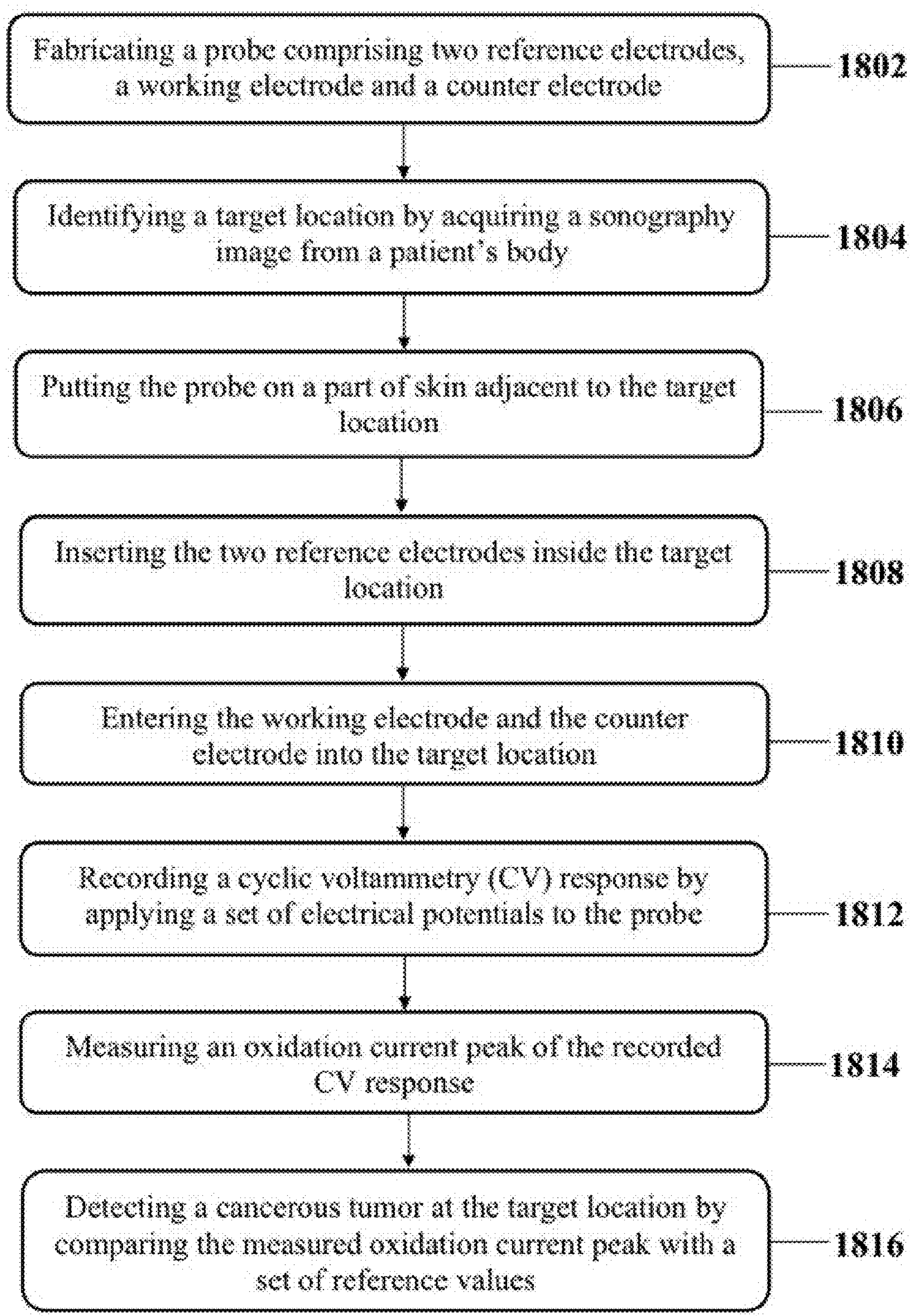
FIG. 18A shows an exemplary method for non-invasive detecting and tracing cancer, consistent with one or more exemplary embodiments of the present disclosure.

FIG. 18A shows exemplary method 1800 for non-invasive detecting and tracing cancer, consistent with one or more exemplary embodiments of the present disclosure. Method 1800 may include fabricating a probe including two reference electrodes, a working electrode located inside a first reference electrode of the two reference electrodes, and a counter electrode located inside a second reference electrode of the two reference electrodes (step 1802), putting the probe on a part of skin adjacent to a target location inside a patient's body (step 1806), inserting the two reference electrodes inside the target location through the part of skin (step 1808), inserting the working electrode and the counter electrode into the target location by releasing the working electrode and the counter electrode through the two reference electrodes (step 1810), recording a cyclic voltammetry (CV) response of hypoxia-related hydrogen peroxide ($H_2O_2$) release in the target location by applying a set of electrical potentials to the probe (step 1812), measuring an oxidation current peak of the recorded CV response (step 1814), and detecting a cancerous tumor at the target location by comparing the measured oxidation current peak with a set of reference values (step 1816). In an exemplary implementation, exemplary method 1800 may further include identifying the target location by acquiring a sonography image from the patient's body (step 1804).

Figure 19A:
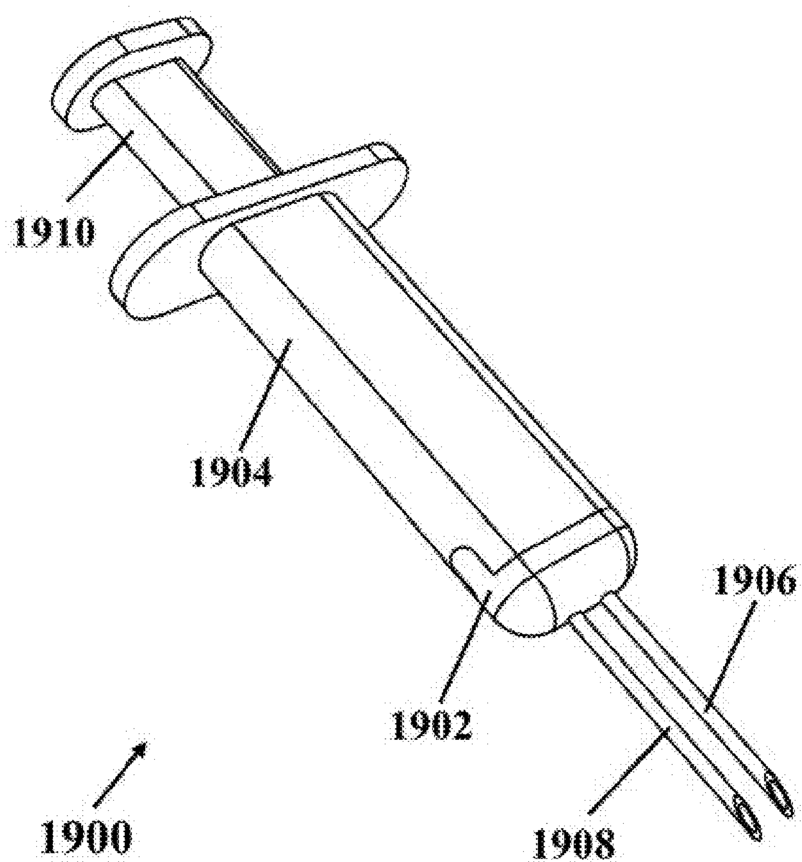
FIG. 19A shows a schematic view of an exemplary probe, consistent with one or more exemplary embodiments of the present disclosure.

In detail, step 1802 may include fabricating a probe. FIG. 19A shows a schematic view of exemplary probe 1900, consistent with one or more exemplary embodiments of the present disclosure. An exemplary probe similar to exemplary probe 1900 may be fabricated utilizing a process similar to step 1802 and may be utilized in exemplary method 1800. Exemplary probe 1900 may include exemplary sensing part 1902 and exemplary holding member 1904. In an exemplary embodiment, exemplary sensing part 1902 may be attached to a first end of exemplary holding member 1904. In an exemplary embodiment, exemplary sensing part 1902 may include two reference electrodes 1906 and 1908. Two reference electrodes 1906 and 1908 may include exemplary first reference electrode 1906 and exemplary second reference electrode 1908. Exemplary first reference electrode 1906 may include a first hollow needle (not illustrated) and exemplary second reference electrode 1908 may include a second hollow needle (not illustrated). In an exemplary embodiment, the first hollow needle and the second hollow needle may both be biocompatible electrically conductive respectively. In an exemplary embodiment, exemplary first reference electrode 1906 and exemplary second reference electrode 1908 may be made of steel. In an exemplary embodiment, each of the first reference electrode 1906 and the second reference electrode 1908 may include a steel syringe.

Figure 19B:
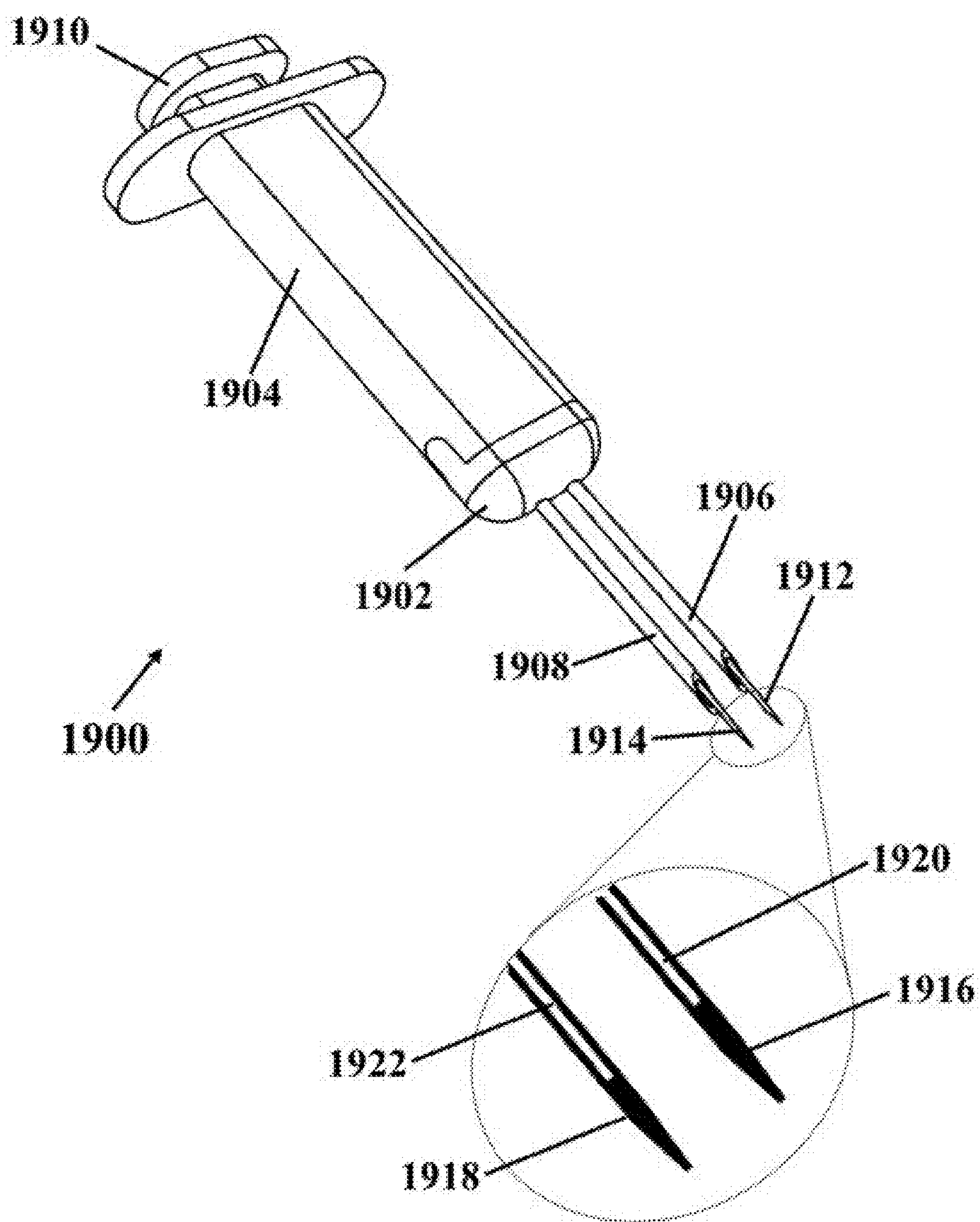
FIG. 19B shows another schematic view of an exemplary probe, consistent with one or more exemplary embodiments of the present disclosure.

FIG. 19B shows another schematic view of exemplary probe 1900, consistent with one or more exemplary embodiments of the present disclosure. Referring to FIG. 19B, exemplary probe 1900 may further include exemplary working electrode 1912 and exemplary counter electrode 1914 which may be located inside two reference electrodes 1906 and 1908, respectively. In an exemplary embodiment, exemplary working electrode 1912 may be located inside exemplary reference electrode 1906 and exemplary counter electrode 1914 may be located inside exemplary reference electrode 1908. In an exemplary embodiment, exemplary working electrode 1912 and exemplary counter electrode 1914 may include biocompatible electrically conductive needles, which may be located inside the first hollow needle and the second hollow needle, respectively. In an exemplary embodiment, exemplary working electrode 1912 and exemplary counter electrode 1914 may be made of steel.

Referring to FIGS. 19A and 19B, exemplary holding member 1904 may include exemplary button 1910 at a second end of holding member 1904. Exemplary button 1910 may be configured to release (push) exemplary working electrode 1912 and exemplary counter electrode 1914 outside through two reference electrodes 1906 and 1908 respectively by pushing exemplary button 1910. Furthermore, exemplary button 1910 may be configured to pull (retract) exemplary working electrode 1912 and exemplary counter electrode 1914 inside exemplary two reference electrodes 1906 and 1908 respectively by pushing exemplary button 1910.

In an exemplary implementation, exemplary probe 1900 may allow for simpler and more clinically applicable electrochemical measurements, such as recording CV responses from a tissue, such as the target location. It should be noted that at least three electrodes, including at least one working electrode, at least one counter electrode, and at least one reference electrode are required for electrochemical measurements using an electrochemical probe. However, inserting three electrodes in a portion of a tissue is very difficult and even is impossible for exemplary small target locations, such as small breat tumors. Specifically, utilizing exemplary probe 1900 with the exemplary structure illustrated in FIGS. 19A and 19B requires insertion of only two reference electrodes 1906 and 1908 in the target location, which may allow for more deep insertions in ultra-small locations within a patient' body. Therefore, utilizing exemplary probe 1900 may provide a non-invasive access to deep small tumors for electrochemical measurements, such as recording CV responses from small breast tumors located everywhere in a breast tissue without any need for conducting a surgery.

In an exemplary embodiment, exemplary working electrode 1912 may include a first needle that may include a first tip 1916 coated with a first layer of carbon nanotubes (CNTs). Moreover, exemplary counter electrode 1914 may include a second needle that may include a second tip 1918 coated with a second layer of CNTs. In an exemplary embodiment, each of the first layer of CNTs and the second layer of CNTs may include a layer of vertically aligned multi-walled carbon nanotubes (VAMWCNTs). In an exemplary embodiment, the VAMWCNTs may include VAMWCNTs with a length between about 0.5 μm and about 10 μm. Furthermore, the VAMWCNTs may include VAMWCNTs with a diameter between about 20 nm and about 100 nm.

In an exemplary embodiment, each of exemplary two reference electrodes 1906 and 1908, exemplary working electrode 1912, and exemplary counter electrode 1914 may include a biocompatible steel needle with a diameter between about 100 μm and about 1 cm, and a length between about 0.1 cm and about 10 cm. In an exemplary embodiment, each of exemplary two reference electrodes 1906 and 1908 may have a diameter twice a diameter of each of exemplary working electrode 1912 and exemplary counter electrode 1914. For example, each of exemplary working electrode 1912 and exemplary counter electrode 1914 may have a diameter about 250 μm while each of exemplary two reference electrodes 1906 and 1908 may have a diameter about 500 μm. In an exemplary embodiment, exemplary two reference electrodes 1906 and 1908 may be fixed apart from each other with a distance between about 1 mm and about 5 mm. In an exemplary embodiment, exemplary two reference electrodes 1906 and 1908 may include two steel syringes.

In an exemplary embodiment, exemplary probe 1900 may be an electrochemical probe including integrated electrodes. The integrated electrodes may be similar to exemplary two reference electrodes 1906 and 1908, exemplary working electrode 1912 and exemplary counter electrode 1914. Exemplary probe 1900 may be utilized for electrochemical measurements, for example, cyclic voltammetry measurements. In an exemplary embodiment, exemplary sensing part 1902 may be replaceable; thereby, exemplary two reference electrodes 1906 and 1908, exemplary working electrode 1912 and exemplary counter electrode 1914 may be replaced by new ones if needed.

Figure 18B:
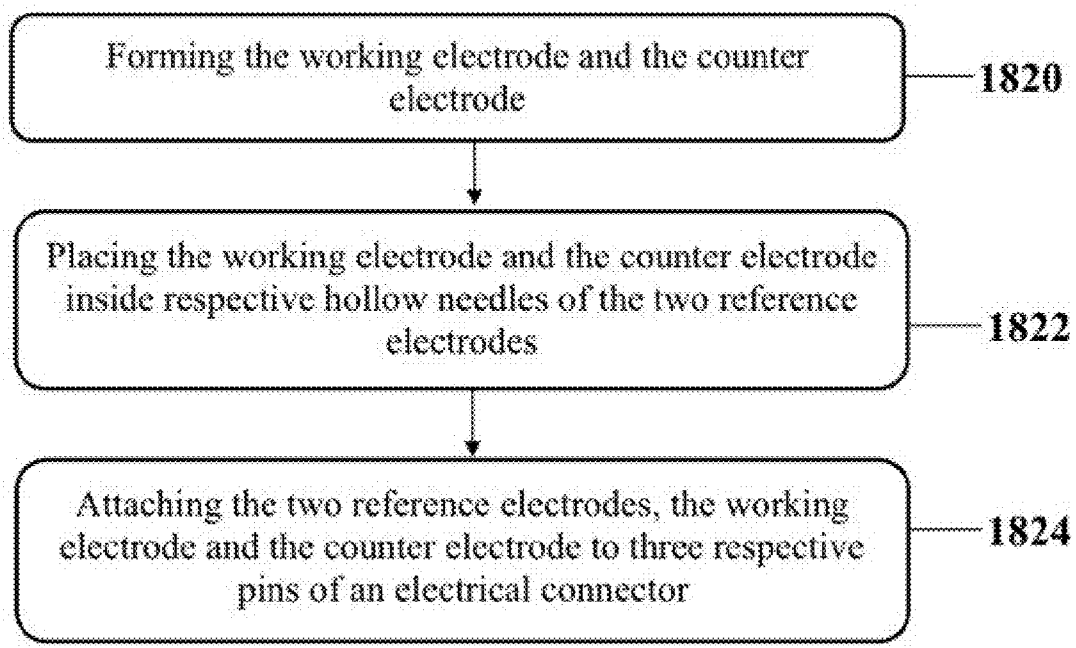
FIG. 18B shows an exemplary implementation of fabricating an exemplary probe, consistent with one or more exemplary embodiments of the present disclosure.

Referring back to FIG. 18A, step 1802 may include fabricating a probe similar to exemplary probe 1900. FIG. 18B shows an exemplary implementation of fabricating exemplary probe 1900 (step 1802), consistent with one or more exemplary embodiments of the present disclosure. In an exemplary implementation, fabricating exemplary probe 1900 (step 1802) may include forming exemplary working electrode 1912 and exemplary counter electrode 1914 (step 1820), placing exemplary working electrode 1912 and exemplary counter electrode 1914 inside respective hollow needles of exemplary two reference electrodes 1906 and 1908 (step 1822), and attaching exemplary two reference electrodes 1906 and 1908, exemplary working electrode 1912 and exemplary counter electrode 1914 to three respective pins of an electrical connector (step 1824).

Figure 18C:
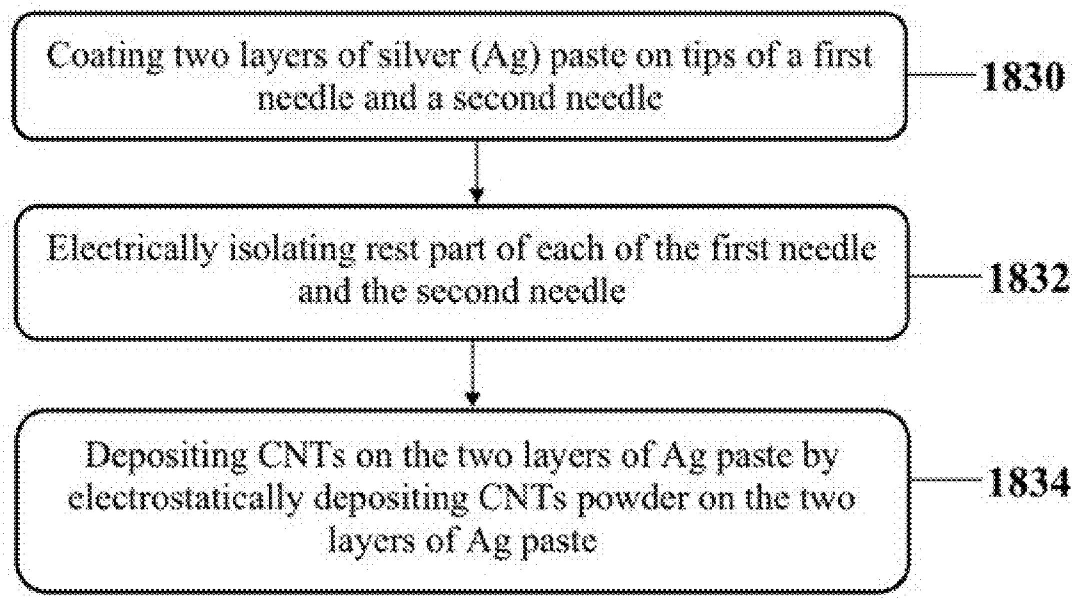
FIG. 18C shows an exemplary implementation of forming an exemplary working electrode and an exemplary counter electrode, consistent with one or more exemplary embodiments of the present disclosure.

FIG. 18C shows an exemplary implementation of forming exemplary working electrode 1912 and exemplary counter electrode 1914 (step 1820), consistent with one or more exemplary embodiments of the present disclosure. Forming exemplary working electrode 1912 and exemplary counter electrode 1914 (step 1820) may include coating two layers of silver (Ag) paste on tips 1916 and 1918 of the first needle and the second needle, respectively (step 1830), electrically isolating rest parts 1920 and 1922 of the first needle and the second needle, respectively (step 1832), and depositing CNTs on the two layers of Ag paste by electrostatically depositing CNTs powder on the two layers of Ag paste (step 1834).

In an exemplary implementation, coating two layers of Ag paste on tips 1916 and 1918 of the first needle and the second needle (step 1830) may include coating a first layer of Ag paste on the first tip 1916 of the first needle and coating a second layer of Ag paste on the second tip 1918 of the second needle. In an exemplary embodiment, the first tip 1916 may have a length of about 0.5 mm to about 5 mm of the first needle. Similarly, the second tip 1918 may have a length of about 0.5 mm to about 5 mm of the second needle. In an exemplary implementation, coating two layers of Ag paste on tips 1916 and 1918 of the first needle and the second needle (step 1830) may include sterilizing the first needle and the second needle, rinsing the sterilized first needle and the sterilized second needle in deionized water (DI), drying the rinsed and sterilized first and second needle by air, and covering the first tip 1916 and the second tip 1918 with Ag paste.

In an exemplary implementation, electrically isolating rest parts 1920 and 1922 of the first needle and the second needle (step 1832) may include covering the first needle and the second needle except the first tip 1916 and the second tip 1918 by an electrically isolator material. In an exemplary embodiment, the electrically isolator material may include at least one of a biocompatible electrically isolator polymer, a biocompatible electrically isolator paste, and combinations thereof.

In an exemplary implementation, depositing CNTs on the two layers of Ag paste by electrostatically depositing CNTs powder on the two layers of Ag paste (step 1834) may include depositing the first layer of CNTs on the first layer of Ag paste, and depositing the second layer of CNTs on the second layer of Ag paste. In an exemplary implementation, depositing CNTs on the two layers of Ag paste may include depositing vertically aligned multi-walled carbon nanotubes (VAMWCNTs) on the two layers of Ag paste. In an exemplary embodiment, the VAMWCNTs may include VAMWCNTs functionalized by carboxyl groups.

In an exemplary implementation, depositing CNTs on the two layers of Ag paste by electrostatically depositing CNTs powder on the two layers of Ag paste (step 1834) may include connecting carboxyl CNTs powder to a positive pole of an electrostatic potential generator, connecting the first needle with Ag paste coated on the first tip 1916 and the second needle with Ag paste coated on the second tip 1918 to a negative pole of the electrostatic potential generator, and electrostatically trapping/grasping CNTs on the two layers of Ag paste by moving the first needle with Ag paste coated on the first tip 1916 and the second needle with Ag paste coated on the second tip 1918 alongside the positive pole of the electrostatic potential generator. In an exemplary embodiment, the electrostatic potential generator may include a Van de Graaff electrostatic generator.

Figure 21:
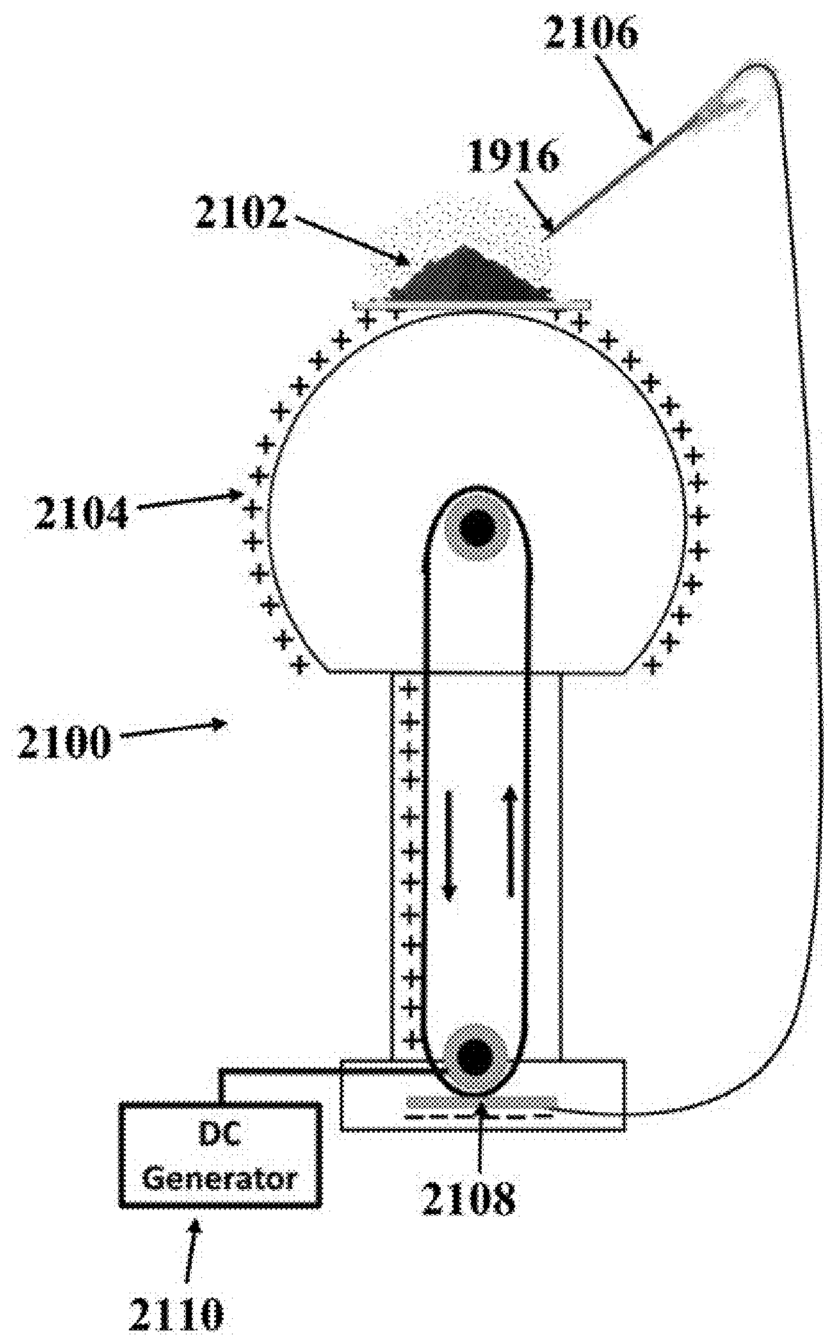
FIG. 21 shows a schematic view of an exemplary implementation of depositing CNTs on an exemplary layer of Ag paste utilizing an exemplary Van de Graaff electrostatic generator, consistent with one or more exemplary embodiments of the present disclosure.

FIG. 21 shows a schematic view of an exemplary implementation of depositing CNTs on an exemplary layer of Ag paste utilizing Van de Graaff electrostatic generator 2100 (step 1834), consistent with one or more exemplary embodiments of the present disclosure. Depositing CNTs on the Ag paste may include placing carboxyl CNTs powder 2102 above positive pole 2104 of Van de Graaff electrostatic generator 2100, connecting exemplary first needle 2106 with Ag paste coated on the first tip 1916 to negative pole 2108 of Van de Graaff electrostatic generator 2100, and moving needle 2106 near carboxyl CNTs powder 2102; thereby, resulting in adhering CNTs onto the first tip 1916 in Ag paste region. Where, Van de Graaff electrostatic generator 2100 may be connected to DC generator 2110.

Referring back to FIG. 18A, step 1804 may include identifying a target location by acquiring a sonography image from a patient's body. In an exemplary embodiment, the target location may include a portion of a tissue, a suspicious region, or a suspicious mass in a patient's body that may be suspicious to be cancerous. In another exemplary embodiment, the target location may include a tumor site in a patient's body that may be treated by a cancer therapy treatment and monitored for tumor size changes or tumor suppression. In an exemplary embodiment, the target location may be identified and targeted using a sonography technique.

Moreover, step 1806 may include putting exemplary probe 1900 on a part of skin adjacent to the target location inside the patient's body. In an exemplary implementation, step 1806 may include putting exemplary probe 1900 on the patient's skin adjacent to the target location, which may be identified in step 1804, while conducting sonography imaging from the patient's body.

Furthermore, step 1808 may include inserting exemplary two reference electrodes 1906 and 1908 inside the target location through the part of skin. In an exemplary implementation, step 1808 may include inserting exemplary two reference electrodes 1906 and 1908 inside the target location through the patient's skin while conducting sonography imaging from the patient's body; thereby, exemplary two reference electrodes 1906 and 1908 may be pushed or squeezed precisely into the target location. In an exemplary implementation, inserting exemplary two reference electrodes 1906 and 1908 inside the target location through the part of skin may include inserting exemplary two reference electrodes 1906 and 1908 inside the target location within a depth from less than about 1 mm up to about 10 cm from an outside skin near the target location. In an exemplary implementation, deep located tumors within the patient's body may be easily accessible for detection of and tracing of a cancerous tumor using exemplary probe 1900 without any need to do a surgery or biopsy. In an exemplary embodiment, "deep located tumors" may refer to tumors located in the patient's body far from the skin, for example, at a depth in the patient's body between 1 cm and 10 cm measured from the skin.

Figure 20:
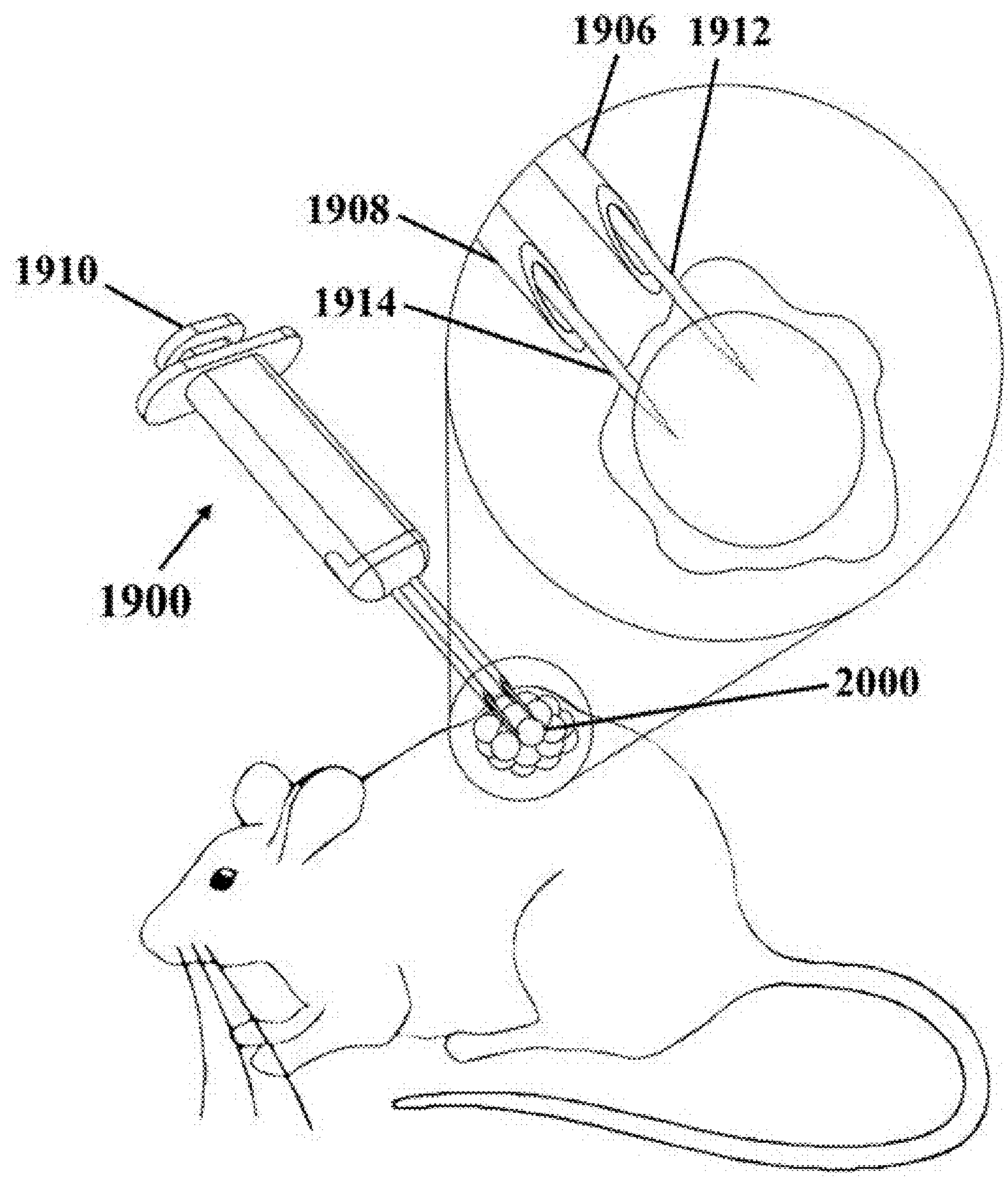
FIG. 20 shows a schematic view of an exemplary implementation of inserting an exemplary working electrode and an exemplary counter electrode of an exemplary probe into an exemplary target location, consistent with one or more exemplary embodiments of the present disclosure.

Additionally, step 1810 may include inserting or pushing exemplary working electrode 1912 and exemplary counter electrode 1914 into the target location by releasing exemplary working electrode 1912 and exemplary counter electrode 1914 through exemplary two reference electrodes 1906 and 1908 respectively. FIG. 20 shows a schematic view of an exemplary implementation of inserting exemplary working electrode 1912 and exemplary counter electrode 1914 of exemplary probe 1900 into exemplary target location 2000, consistent with one or more exemplary embodiments of the present disclosure. In an exemplary implementation, inserting exemplary working electrode 1912 and exemplary counter electrode 1914 of exemplary probe 1900 into exemplary target location 2000 may include pushing exemplary working electrode 1912 and exemplary counter electrode 1914 into exemplary target location 2000 by pressing exemplary button 1910. Pressing exemplary button 1910 may result in releasing exemplary working electrode 1912 and exemplary counter electrode 1914 from exemplary two reference electrodes 1906 and 1908, and squeezing exemplary working electrode 1912 and exemplary counter electrode 1914 inside exemplary target location 2000. In an exemplary implementation, inserting exemplary working electrode 1912 and exemplary counter electrode 1914 of exemplary probe 1900 into exemplary target location 2000 may be carried out while at the same time conducting sonography imaging from the patient's body (i.e., imaging from exemplary target location 2000); thereby, exemplary working electrode 1912 and exemplary counter electrode 1914 may be pushed or squeezed precisely into exemplary target location 2000. In an exemplary implementation, inserting exemplary working electrode 1912 and exemplary counter electrode 1914 of exemplary probe 1900 into exemplary target location 2000 may include putting the first tip 1916 and the second tip 1918 in contact with exemplary target location 2000.

In an exemplary implementation, step 1812 may include recording a cyclic voltammetry (CV) response of hypoxia-related hydrogen peroxide ($H_2O_2$) release in target location 2000 by applying a set of electrical potentials to exemplary probe 1900. In an exemplary implementation, applying the set of electrical potentials to exemplary probe 1900 may include applying the set of electrical potentials to exemplary working electrode 1912. In an exemplary implementation, applying the set of electrical potentials to exemplary working electrode 1912 may include applying a sweeping range of electrical potentials between about −1 V and about 1 V to exemplary working electrode 1912. In an exemplary implementation, applying the set of electrical potentials to exemplary working electrode 1912 may include applying a sweeping range of electrical potentials between about −0.8 V and about 0.8 V to exemplary working electrode 1912.

In an exemplary implementation, applying the set of electrical potentials to exemplary working electrode 1912 may include applying the set of electrical potentials to exemplary working electrode 1912 using an electrochemical stimulator-analyzer device. In an exemplary embodiment, the electrochemical stimulator-analyzer device may comprise a potentiostat device. In an exemplary implementation, applying the set of electrical potentials to exemplary working electrode 1912 may include connecting exemplary probe 1900 to the potentiostat device, and applying the set of electrical potentials to exemplary working electrode 1912 by the potentiostat device.

In an exemplary implementation, recording the CV response may include recording the CV response responsive to applying the set of electrical potentials to exemplary working electrode 1912 inserted into target location 2000. In an exemplary implementation, recording the CV response may include connecting exemplary probe 1900 to the potentiostat device, applying the set of electrical potentials to exemplary working electrode 1912 by the potentiostat device, and recording the CV response by a processor which may be connected to the potentiostat device.

Figure 22:
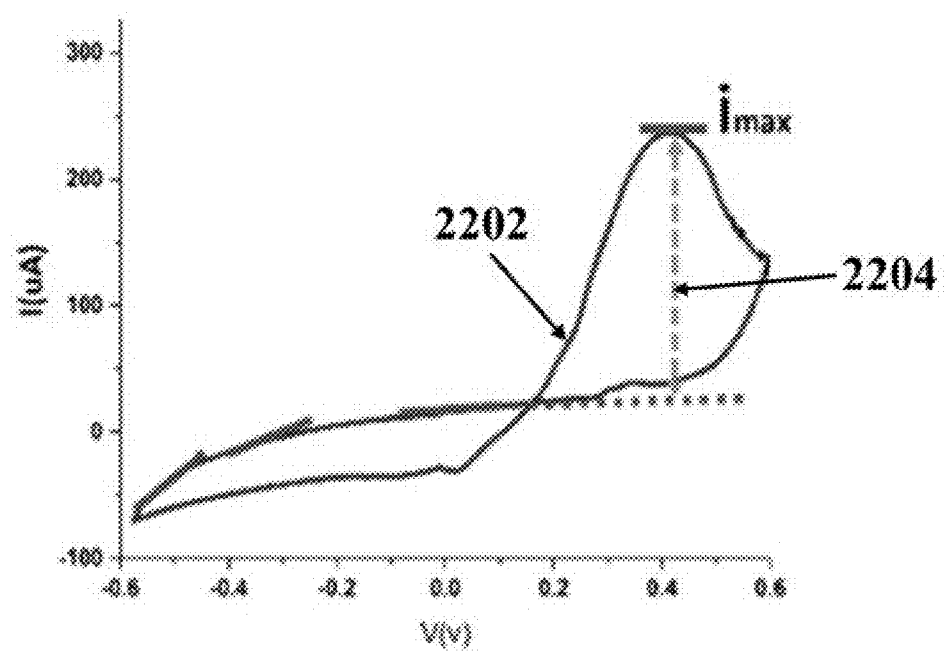
FIG. 22 shows an exemplary CV response recorded from an exemplary target location utilizing an exemplary probe, consistent with one or more exemplary embodiments of the present disclosure.

FIG. 22 shows an exemplary CV response 2202 recorded from target location 2000 utilizing exemplary probe 1900, consistent with one or more exemplary embodiments of the present disclosure. In an exemplary implementation, recorded CV response 2202 may include a curve including a set of electrical current values versus the set of the applied electrical potentials. The set of electrical current values may be generated between exemplary working electrode 1912 and exemplary counter electrode 1914 responsive to applying the set of electrical potentials to exemplary probe 1900. The set of electrical current values may be in correlation with Hydrogen Peroxide ($H_2O_2$) that may be released during hypoxia glycolysis and reverse Warburg phenomena in cancer cells. Therefore, recorded CV response 2202 may be a determinative criterion for detecting cancer cells within exemplary target location 2000. Exemplary recorded CV response 2202 may include an oxidation current peak 2204 related to oxidation of $H_2O_2$. In an exemplary implementation, if exemplary target location 2000 includes cancer cells, recorded CV response 2202 may include oxidation current peak 2204 with an amount larger than a threshold value.

In an exemplary implementation, step 1814 may include measuring exemplary oxidation current peak 2204 of exemplary recorded CV response 2202 that may include measuring $H_2O_2$ oxidation within target location 2000. Exemplary oxidation current peak 2204 of recorded CV response 2202 may have a larger value for cancer cells in comparison with healthy (normal) cells due to hypoxia glycolysis and reverse Warburg phenomena in cancer cells.

Figure 18D:
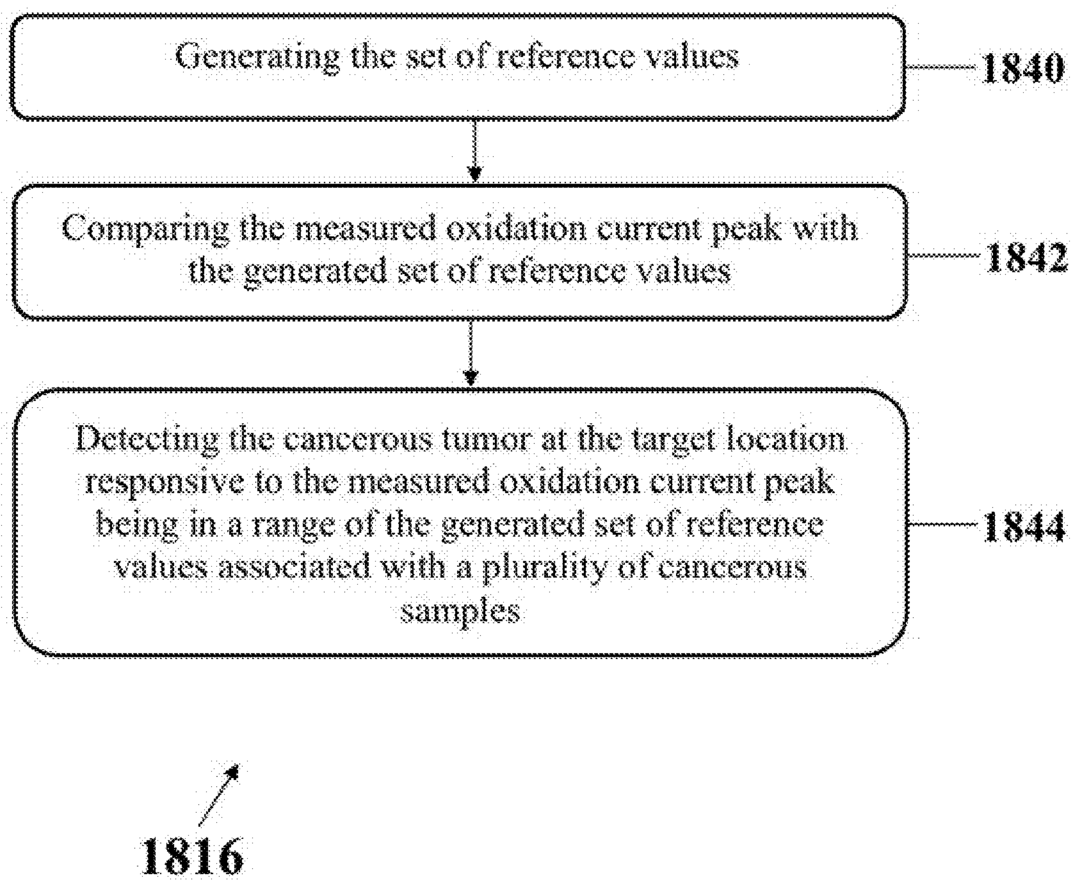
FIG. 18D shows an exemplary implementation of detecting the cancerous tumor at an exemplary target location, consistent with one or more exemplary embodiments of the present disclosure.

In an exemplary implementation, step 1816 may include detecting a cancerous tumor at target location 2000 by comparing the measured oxidation current peak 2204 with a set of reference values. FIG. 18D shows an exemplary implementation of detecting the cancerous tumor at exemplary target location 2000 (step 1816), consistent with one or more exemplary embodiments of the present disclosure. Detecting the cancerous tumor at exemplary target location 2000 (step 1816) may include generating the set of reference values (step 1840), comparing the measured oxidation current peak 2204 with the generated set of reference values (step 1842), and detecting the cancerous tumor at exemplary target location 2000 responsive to the measured oxidation current peak 2204 being in a range of the generated set of reference values associated with a plurality of cancerous samples (step 1844).

In an exemplary implementation, generating the set of reference values (step 1840) may include recording a set of CV responses similar to CV response 2202 from a plurality of samples using exemplary fabricated probe 1900, and measuring a respective set of oxidation current peaks similar to oxidation current peak 2204 of the recorded set of CV responses. The plurality of samples may include a plurality of healthy samples and the plurality of cancerous samples. The plurality of samples may include a plurality of known or pre-determined healthy samples and a plurality of known or pre-determined cancerous samples. A situation of being healthy or being cancerous may be pre-determined by pathological assays for a plurality of cell lines and/or a plurality of biopsied samples.

In an exemplary implementation, comparing the measured oxidation current peak 2204 with the generated set of reference values (step 1842) may include looking up a value of the measured oxidation current peak 2204 in step 1814 to determine whether the measured oxidation current peak 2204 may be placed within a range of the generated set of reference values associated with the plurality of healthy samples or the range of the generated set of reference values associated with the plurality of cancerous samples. As a result, a cancerous tumor may be detected at exemplary target location 2000 in step 1844 if the measured oxidation current peak 2204 is within a range of the generated set of reference values associated with the plurality of cancerous samples.

In an exemplary implementation, steps 1804-1816 may be carried out several times for detecting and tracing cancer in a patient's body in order to diagnose a cancerous tumor margins or monitoring changes in a cancerous tumor during a cancer therapy treatment. In an exemplary implementation, exemplary sensing part 1902 may be replaced by a fresh exemplary sensing part 1902 for iteratively conducting steps 1804-1816.

In an exemplary implementation, exemplary method 1800 may further include returning exemplary working electrode 1912 and exemplary counter electrode 1914 back into exemplary two reference electrodes 1906 and 1908 by pressing exemplary button 1910, and exiting or retracting exemplary two reference electrodes 1906 and 1908 from exemplary target location 2000.

Example 1: Fabrication of CNT Based Electrochemical Chip for In Vitro Assays

In this example, exemplary CNT based electrochemical chips was fabricated for in vitro assays. First, silicon wafer (p-type <100>) substrates were cleaned through standard RCA #1 method ($NH_4OH$:$H_2O_2$:$H_2O$ solution and volume ratio of 1:1:5 respectively). Then, the cleaned substrates were rinsed in deionized (DI) water and dried by air. A thin layer of $SiO_2$ with a thickness of about 200 nm was grown by wet oxidation furnace on the surface of the silicon wafer, as a passivation layer. Nickel (Ni) catalyst layer for CNT growth with a thickness of about 9 nm was coated on $SiO_2$ by E-beam evaporation system at a temperature of about 120° C. with depositing rate of about 0.1 Angstroms/s. Afterwards, Ni-covered samples were located in a direct current plasma enhanced chemical vapor deposition (DC-PECVD) system to grow vertically aligned multi-walled carbon nanotubes (VAMWCNT). The growth process has three steps, including annealing, graining and growth. At first, the sample was annealed at a temperature of about 680° C. in an $H_2$ environment with a flow rate of about 35 standard cubic centimeters per minute (sccm) for about 30 minutes. During the graining, the surface was plasma hydrogenated for about 5 minutes with the intensity of about 5.5 $W \cdot cm^{-2}$ which results in the catalyst graining and formation of Ni nano-sized islands. In the growth step a plasma of $C_2H_2$ and $H_2$ mixture with flow rates of about 5 sccm and about 35 sccm were introduced to the chamber for about 15 minutes. Finally, CNT's were characterized with field emission scanning electron microscopy (FESEM). The length of CNTs ranged from about 2.5 to about 5 μm and the diameter of CNTs ranged from about 50 nm to about 70 nm.

Figure 4:
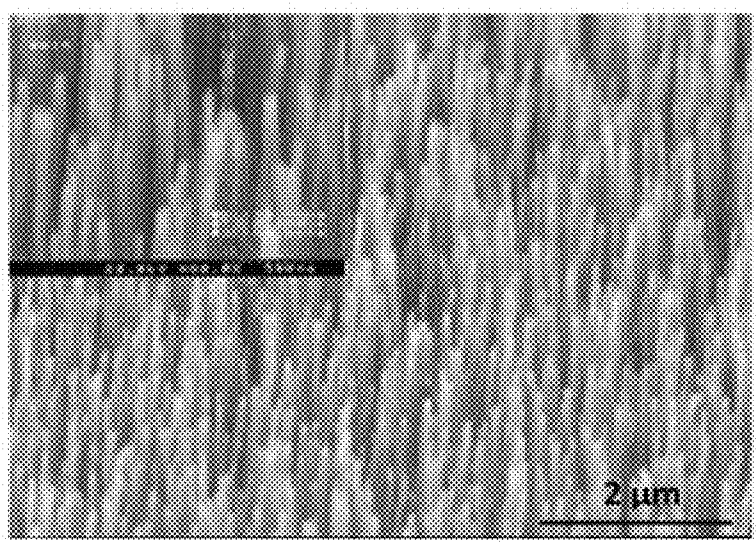
FIG. 4 illustrates a field emission scanning electron microscopy (FESEM) image of the VAMWCNTs array on a portion of an exemplary fabricated CNT based electrochemical chip, consistent with one or more exemplary embodiments of the present disclosure.

FIG. 4 shows the FESEM image of the VAMWCNTs array on a portion of an exemplary fabricated CNT based electrochemical chip, consistent with one or more exemplary embodiments of the present disclosure. The CNTs were multi-walled carbon nanotubes with high purity and a presence of nickel on the top side of the CNTs could be related to the tip-growth mechanism. The CNT has been used as the work, counter and reference electrodes in exemplary fabricated CNT based electrochemical chips. The active area of the work, counter and reference electrodes were about 100 $mm^2$, 100 $mm^2$, 50 $mm^2$, respectively. The CNT based electrochemical chips were connected to a potentiostat by conductive wires bonded to the pads of the potentiostat.

Example 2: Fabrication of Cancer Diagnostic Probe (CDP) for In Vivo Assays

In this example, the tips of sterile steel needles were coated by Ni catalyst layers similar to that was described in EXAMPLE 1 for CNT based electrochemical chips with the assistance of E-Beam coating system. A fixture was designed and fabricated to hold the needles both in E-Beam and DC-PECVD systems to limit the growth of CNTs just in the tips of the needles. Then, the CNT grown needles were attached to electrical connectors with three pins by a conductive paste. Just tips of the needle were extended from the connectors up to about 1 cm. The probe was reinforced with a homemade holder and connected to a readout system by a noiseless cable which handled all three electrodes.

Figure 5A:
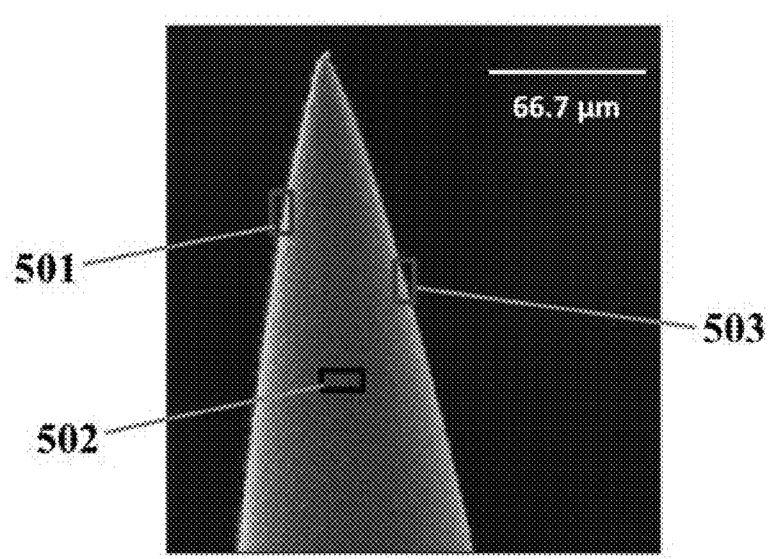
FIG. 5A illustrates a FESEM image of a tip of a needle electrode of an exemplary fabricated cancer diagnostic probe (CDP) coated with an array of VAMWCNTs on the tip, consistent with one or more exemplary embodiments of the present disclosure.
Figure 5B:
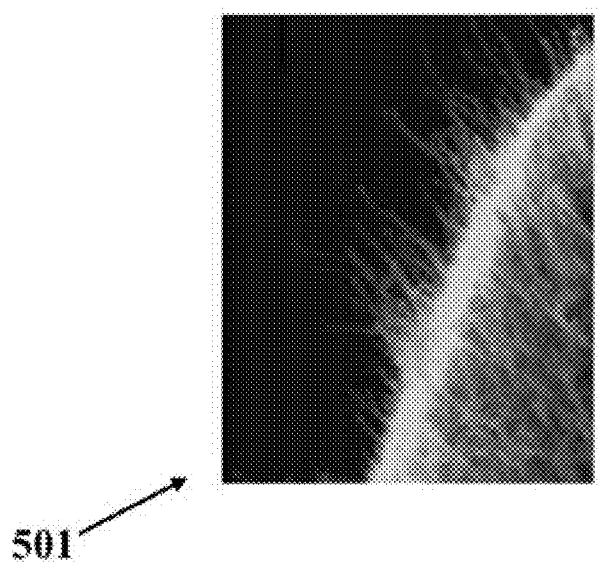
FIG. 5B illustrates a FESEM image of a first portion of an exemplary VAMWCNTs array grown on the tip of the needle electrode of exemplary fabricated CDP, consistent with one or more exemplary embodiments of the present disclosure.
Figure 5C:
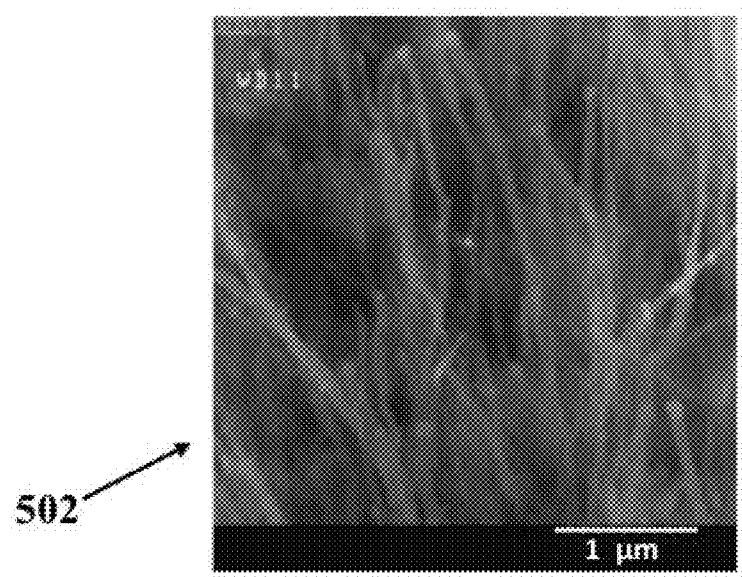
FIG. 5C illustrates a FESEM image of a second portion of an exemplary VAMWCNTs array grown on the tip of the needle electrode of exemplary fabricated CDP, consistent with one or more exemplary embodiments of the present disclosure.
Figure 5D:
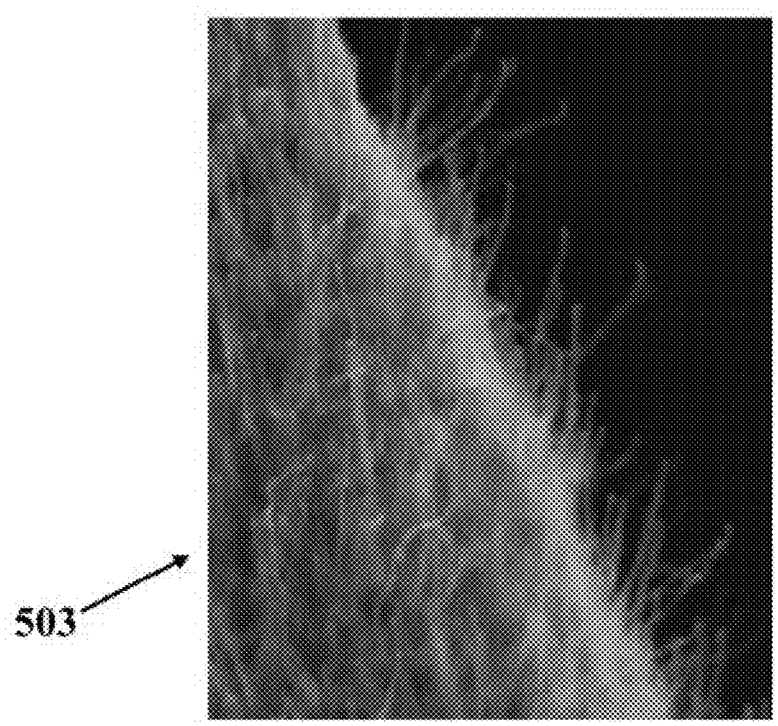
FIG. 5D illustrates a FESEM image of a third portion of an exemplary VAMWCNTs array grown on the tip of the needle electrode of exemplary fabricated CDP, consistent with one or more exemplary embodiments of the present disclosure.

FIGS. 5A-5D show FESEM images of a tip of a needle electrode of an exemplary fabricated cancer diagnostic probe (CDP) coated with an array of VAMWCNTs on the tip and exemplary portions 501, 502 and 503 of the tip, consistent with one or more exemplary embodiments of the present disclosure. FIG. 5A illustrates a FESEM image of the tip of a needle electrode of an exemplary fabricated cancer diagnostic probe (CDP) coated with the array of VAMWCNTs on the tip, consistent with one or more exemplary embodiments of the present disclosure. FIG. 5B illustrates a FESEM image of portion 501 of the tip, consistent with one or more exemplary embodiments of the present disclosure. FIG. 5C illustrates a FESEM image of portion 502 of the tip, consistent with one or more exemplary embodiments of the present disclosure. FIG. 5D illustrates a FESEM image of portion 503 of the tip, consistent with one or more exemplary embodiments of the present disclosure.

Example 3: CV of $H_2O_2$ Contained Lactate Solution

In this example, the cyclic voltammetry (CV) diagram of L-lactic acid solution individually were recorded by exemplary electrochemical sensors including working electrodes (WEs) fabricated from platinum (Pt), Gold (Au), amorphous glassy carbon (GC) and carbon nanotube (CNT).

Figure 6A:
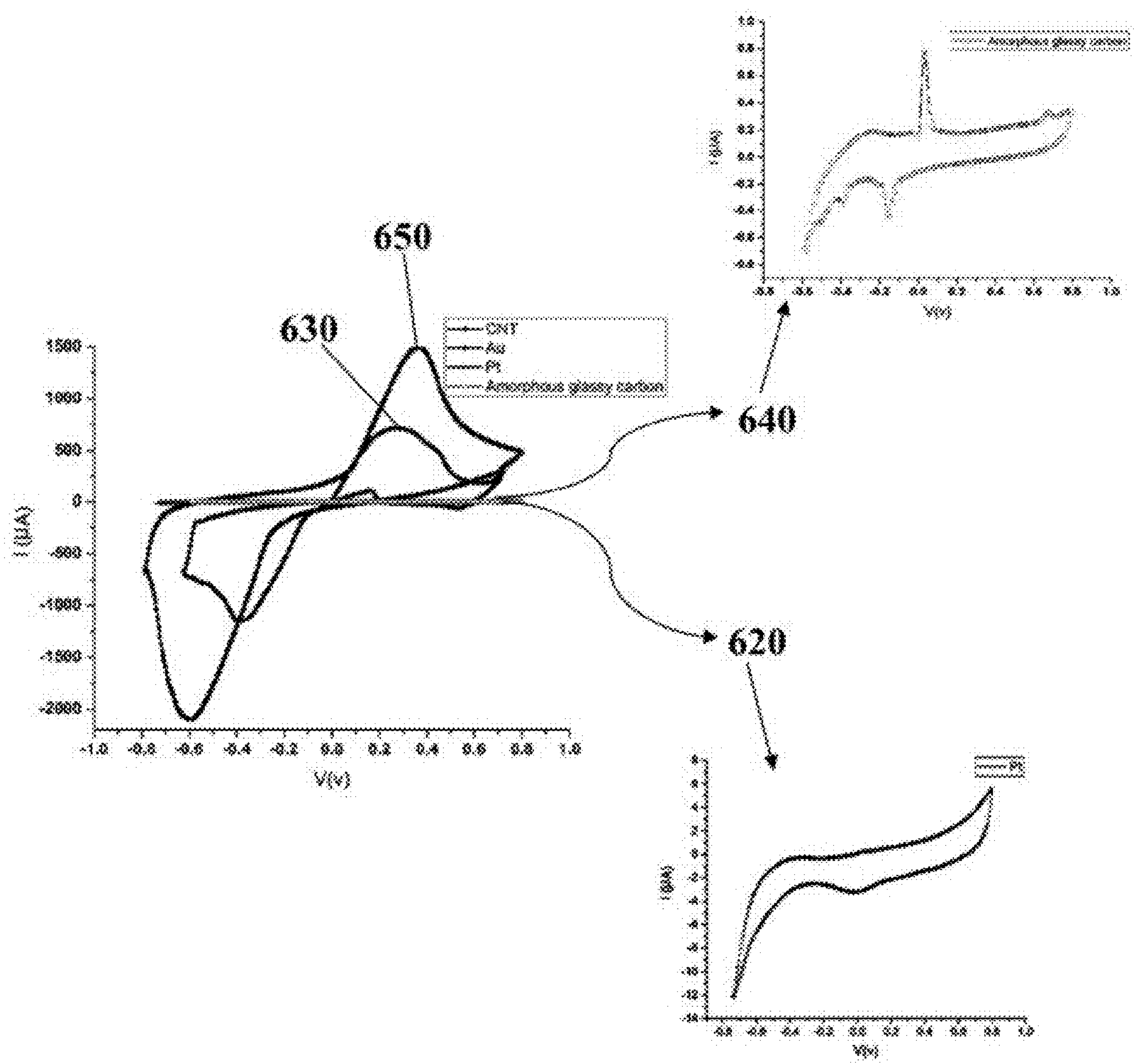
FIG. 6A illustrates the CV diagrams of L-lactic acid solution individually recorded by electrochemical sensors fabricated from platinum (Pt), Gold (Au), amorphous glassy carbon (GC) and carbon nanotube (CNT) working electrodes (WEs), consistent with one or more exemplary embodiments of the present disclosure.

FIG. 6A shows the CV diagrams of L-lactic acid solution individually recorded by electrochemical sensors fabricated from platinum (Pt) (curve 620), Gold (Au) (curve 630), amorphous glassy carbon (GC) (curve 640), and carbon nanotube (CNT) working electrodes (WEs) (curve 650), consistent with one or more exemplary embodiments of the present disclosure. It may be observed that the detected cathodic peak by CNT WE was so sharper (about 1500 μA) in similar concentration of $H_2O_2$ with respect to other electrodes (about 717, 5.7 and 0.8 μA in Au, Pt and GC electrodes, respectively). CNT greatly transfer the released charges from oxidized $H_2O_2$ beneath the nanotubes in media solution. Hence, CNT arrays were used as electrodes of exemplary sensors in the present disclosure.

Figure 6B:
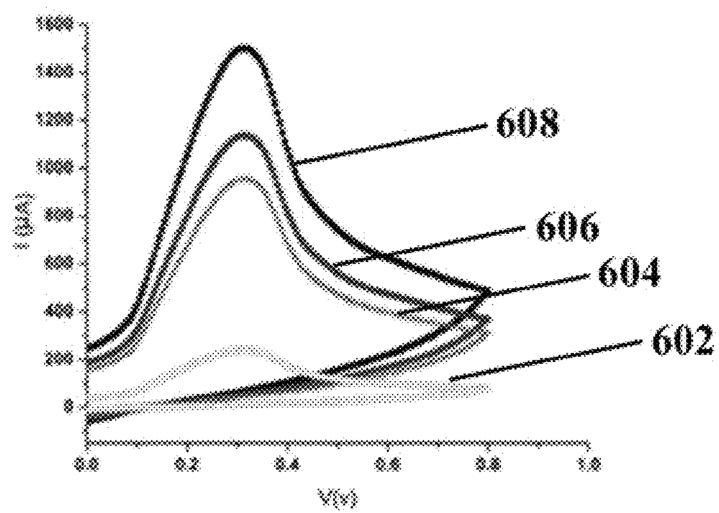
FIG. 6B illustrates the CV diagrams of solutions with various concentrations of Hydrogen Peroxide ($H_2O_2$) resulted from the lactate turn to $H_2O_2$ and pyruvate recorded by electrochemical sensors with CNT arrays working electrode, consistent with one or more exemplary embodiments of the present disclosure.

FIG. 6B shows the CV diagrams of solutions with various concentrations of lactate (and subsequently $H_2O_2$) recorded by electrochemical sensors with CNT arrays working electrode, consistent with one or more exemplary embodiments of the present disclosure. CV diagrams were recorded for solutions with a lactate concentration of about 0.025 mM (CV diagram 602), 0.05 mM (CV diagram 604), 0.1 mM (CV diagram 606), and 0.3 mM (CV diagram 608). CNT working electrode presented a well concentration depended increased response to the presence of lactate molecules in the solutions ranged from about 0.025 mM (CV diagram 602) to about 0.3 mM (diagram 608).

Figure 6C:
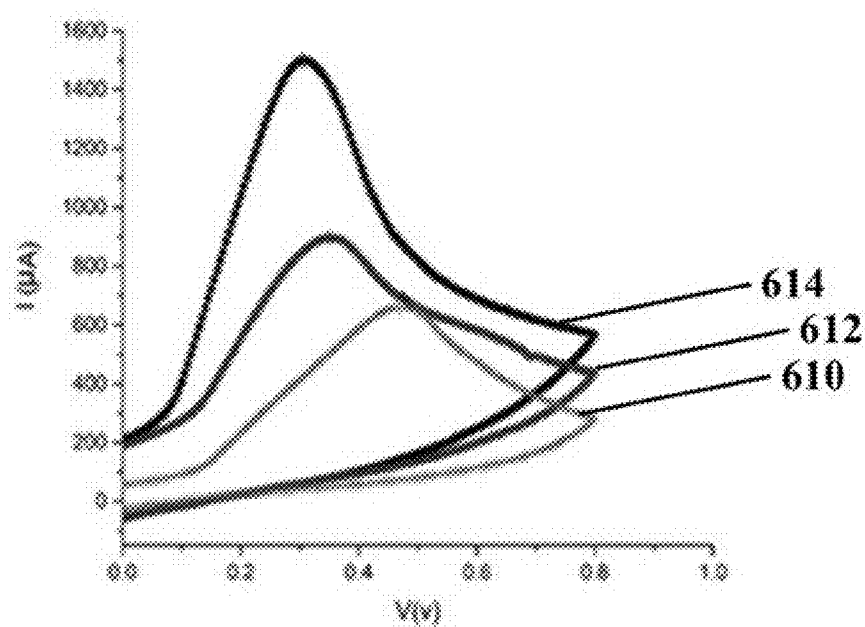
FIG. 6C illustrates the CV diagrams of $H_2O_2$ contained lactate solution in comparison with two cell culture solutions recorded by electrochemical sensors with CNT arrays working electrode, consistent with one or more exemplary embodiments of the present disclosure.

FIG. 6C shows the CV diagrams of $H_2O_2$ contained lactate solution with a lactate concentration of about 0.3 mM (CV diagram 614) in comparison with two cell culture solutions RPMI (CV diagram 610) and DMEN (CV diagram 612) recorded by electrochemical sensors with CNT arrays working electrode, consistent with one or more exemplary embodiments of the present disclosure. It may be observed that RPMI and DMEN cell culture solutions show less electrochemical responses in comparison with $H_2O_2$ contained lactate solution. The RPMI presented no electrochemical responses in the voltage attributed to the lactate detection. As a result, RPMI could be applied as cellular and tissue culture media with a negligible false positive response.

Example 4: Electrochemical Responses of Different Cell Lines

In this example, electrochemical sensing of $H_2O_2$ produced during Lactate/Pyruvate hypoxic glycolysis was verified in four different phenotypes of breast cell lines ranged from normal to malignant stages, including: MCF10 A, MCF-7, MDA-MB-231, and MDA-MB-468. Breast cancer cell lines (MCF10A, MCF-7, MDA-MB-231, MDA-MB-468) were obtained and were maintained at 37° C. (5% $CO_2$, 95% air) in RPMI medium supplemented with 5% fetal bovine serum, and 1% penicillin/streptomycin. The fresh medium was replaced every other day. All cell lines were tested and found negative for *Mycoplasma* contamination. The cells were detached from the plates by trypsin and counted by neobar laam.

Figure 7:
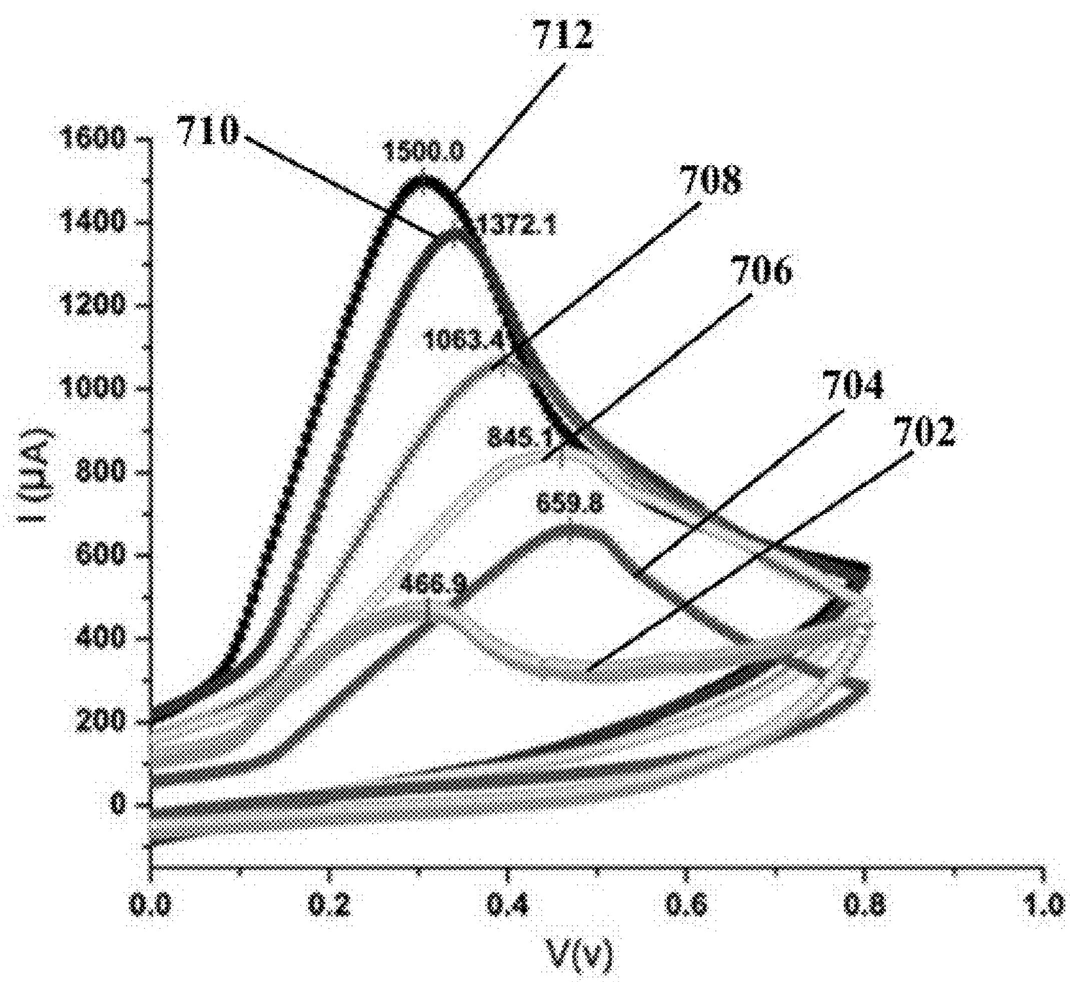
FIG. 7 illustrates the CV diagrams of hypoxic glycolysis in MCF 10A, MCF-7, MDA-MB-231, and MDA-MB-468 cell lines in comparison with $H_2O_2$ contained lactate solution and RPMI measured and recorded by exemplary CNT based electrochemical chip, consistent with one or more exemplary embodiments of the present disclosure.

FIG. 7 shows the CV responses of normal (MCF10A: CV diagram 702) and different grades of cancerous (MCF7: CV diagram 706, MDA-MB231: CV diagram 708, and MDA-B468: CV diagram 710) breast cells' solution media cultured for about 48 hours in comparison with standard $H_2O_2$ contained lactate solution with a lactate concentration of about 0.3 mM (CV diagram 712) and RPMI (CV diagram 704) in individual sensing wells of exemplary fabricated sensor in EXAMPLE 1 herein above, consistent with one or more exemplary embodiments of the present disclosure. Lactate production due to hypoxic glycolysis would be well detectable after about 48 hours of incubation in cancer cell lines. The CV diagrams of FIG. 7 show that the intensity of oxidation peak, located at the position of $H_2O_2$ electrochemical response, significantly increased with the progression in invasive grades of cancer cells in which hypoxia glycolysis would be enhanced.

Referring to FIG. 6B and FIG. 7, sharp difference in electrochemical peaks of $H_2O_2$ contained lactate solution was observed from about 0.025 mM to about 0.05 mM which could be applied to calibrate cancer cells' media from normal ones. Because the electrochemical responses of cancer cells' media solution was equal to the response range of $H_2O_2$ contained lactate solution with the concentration of more than about 0.05 mM meanwhile such response in normal cells was equal to the response range of the $H_2O_2$ contained lactate solution with the concentration of less than about 0.025 mM.

Moreover, similar responses were recorded from the culture media of colon, prostate, liver, lung, mouth, neural and hematopoietic cell lines in normal and cancer phenotypes with invasive and moderate grades by electrochemical sensing of $H_2O_2$ produced during Lactate/Pyruvate hypoxic glycolysis for some other types of colon, neural, prostate, liver, mouth, hematopoietic and lung cell lines. Colon (COR-L 105, SW-480, HT-29), Hematopoietic (1301, LCL-PI 1), Liver (HEP G2), Lung (QU-DB, MRC-5), Mouth (KB), Neuron (BE(2)-C, LAN-5), Prostate (PC-3, Du-145) cell lines were obtained and were maintained at 37° C. (5% $CO_2$, 95% air) in RPMI medium supplemented with 5% fetal bovine serum, and 1% penicillin/streptomycin. The fresh medium was replaced every other day. All cell lines were tested and found negative for *Mycoplasma* contamination. The cells were detached from the plates by trypsin and counted by neobar laam.

Figure 8A:
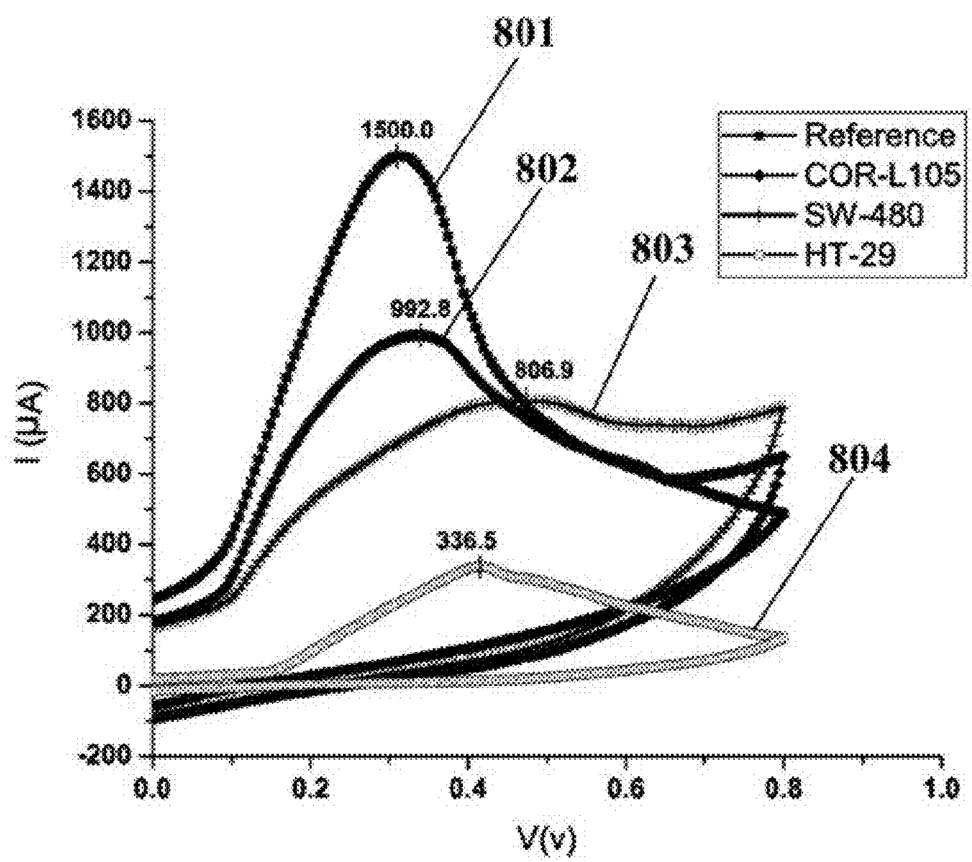
FIG. 8A illustrates the CV responses of the solution media of different normal and cancerous cell lines in various phenotypes for Colon (COR-L 105, SW-480, HT-29) cell lines in comparison with Reference diagram for solution $H_2O_2$ contained solution with a lactate concentration of about 0.3 mM, consistent with one or more exemplary embodiments of the present disclosure.
Figure 8B:
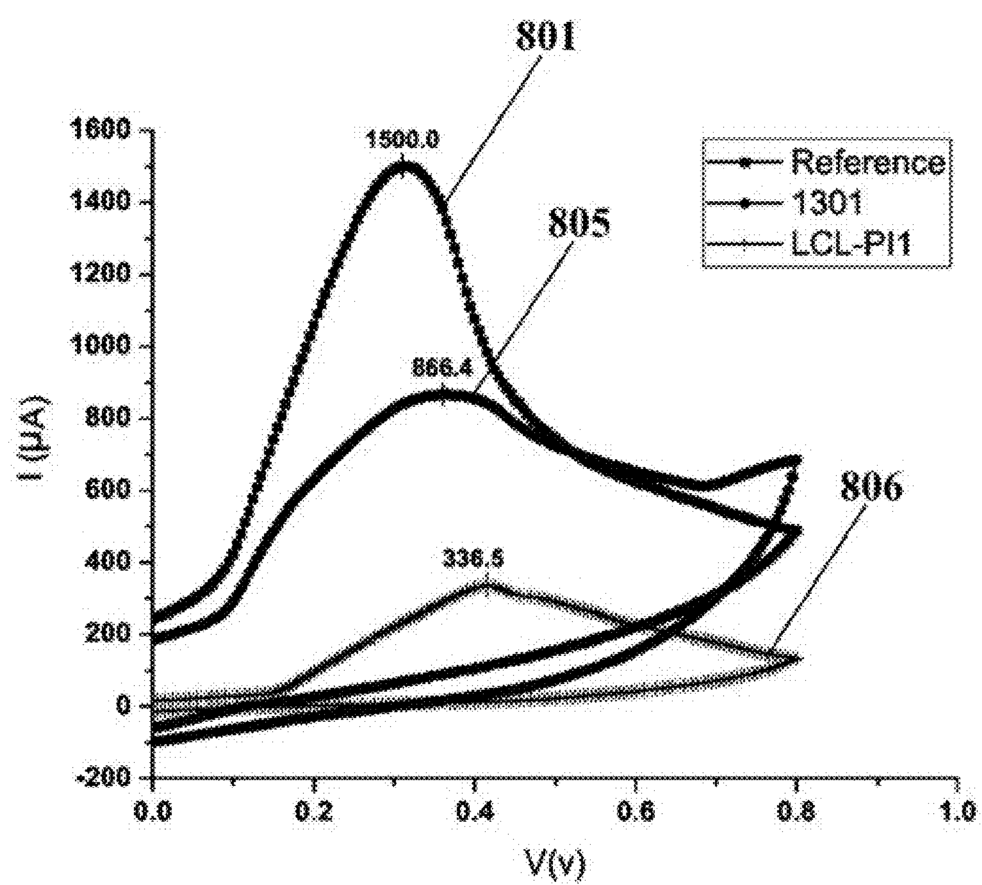
FIG. 8B illustrates the CV responses of the solution media of different normal and cancerous cell lines in various phenotypes for Hematopoietic (1301, LCL-PI 1) cell lines in comparison with Reference diagram for $H_2O_2$ contained solution with a lactate concentration of about 0.3 mM, consistent with one or more exemplary embodiments of the present disclosure.
Figure 8C:
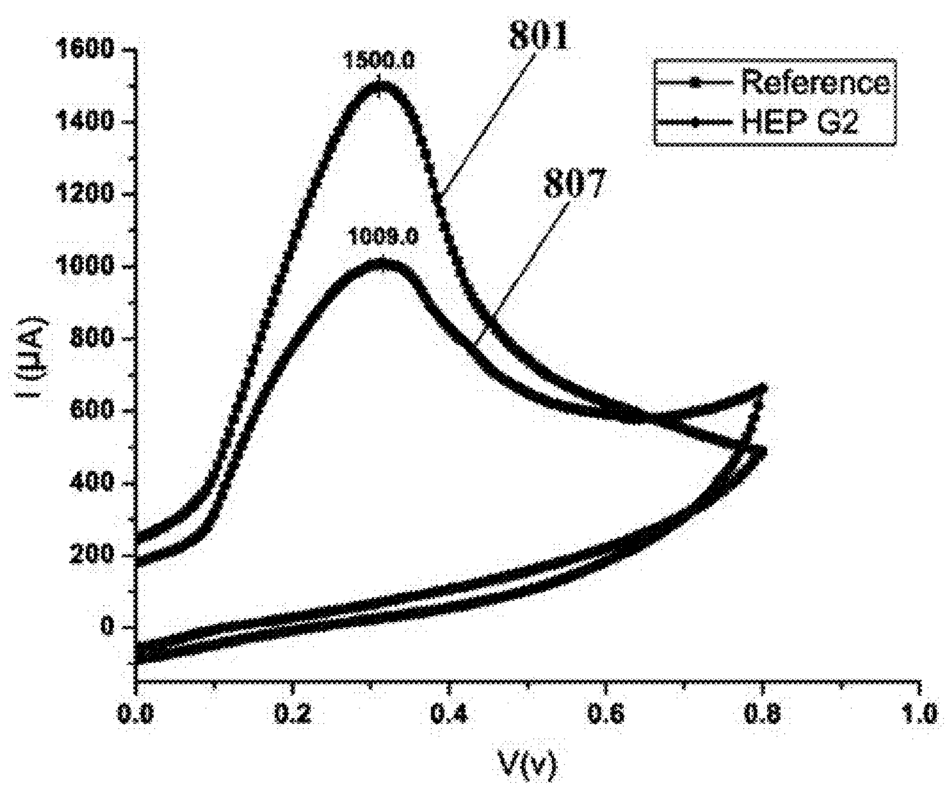
FIG. 8C illustrates the CV responses of the solution media of different normal and cancerous cell lines in various phenotypes for Liver (HEP G2) cell lines in comparison with Reference diagram for $H_2O_2$ contained lactate solution with a lactate concentration of about 0.3 mM, consistent with one or more exemplary embodiments of the present disclosure.
Figure 8D:
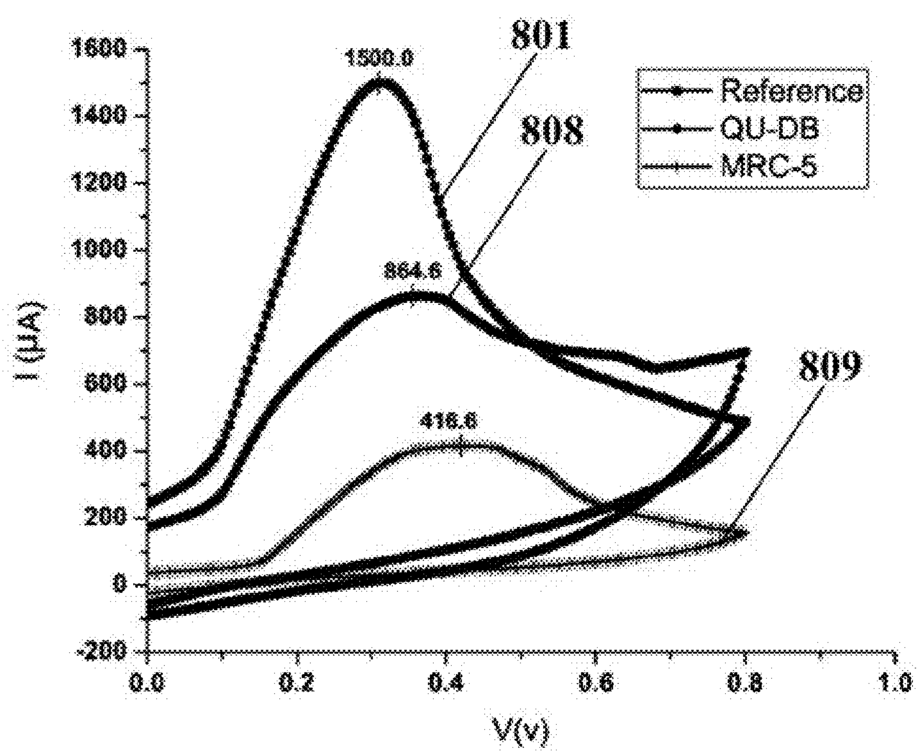
FIG. 8D illustrates the CV responses of the solution media of different normal and cancerous cell lines in various phenotypes for Lung (QU-DB, MRC-5) cell lines in comparison with Reference diagram for $H_2O_2$ contained lactate solution with a lactate concentration of about 0.3 mM, consistent with one or more exemplary embodiments of the present disclosure.
Figure 8E:
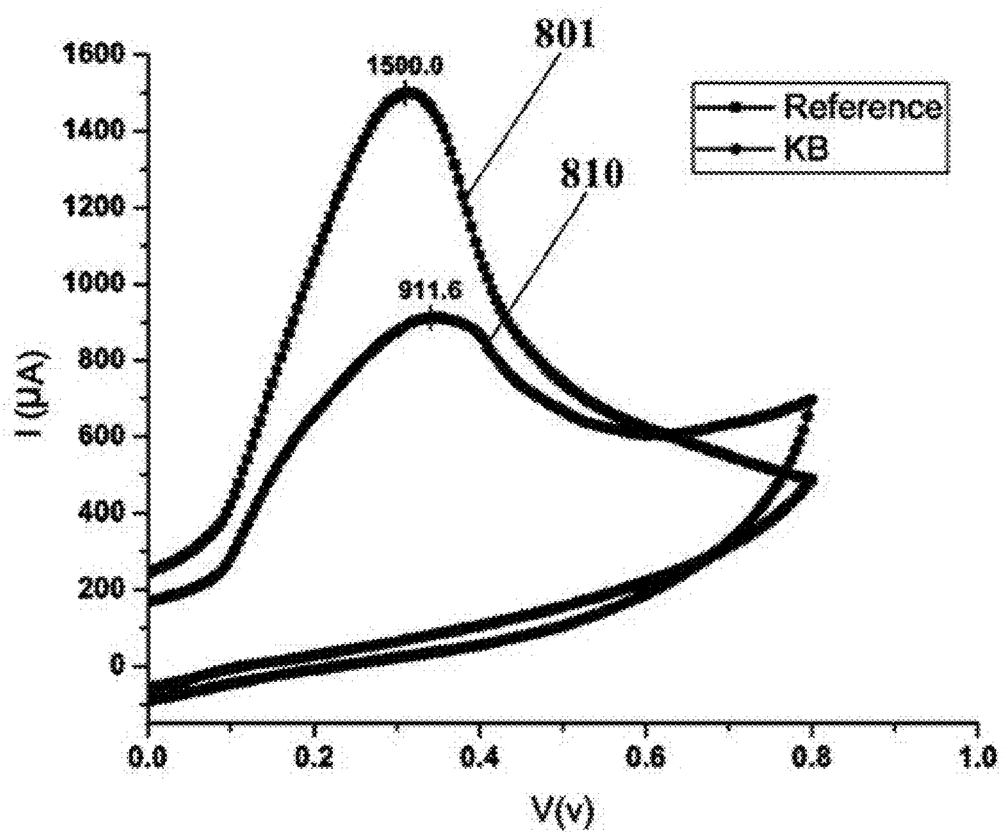
FIG. 8E illustrates the CV responses of the solution media of different normal and cancerous cell lines in various phenotypes for Mouth (KB) cell lines in comparison with Reference diagram for $H_2O_2$ contained lactate solution with a lactate concentration of about 0.3 mM, consistent with one or more exemplary embodiments of the present disclosure.
Figure 8F:
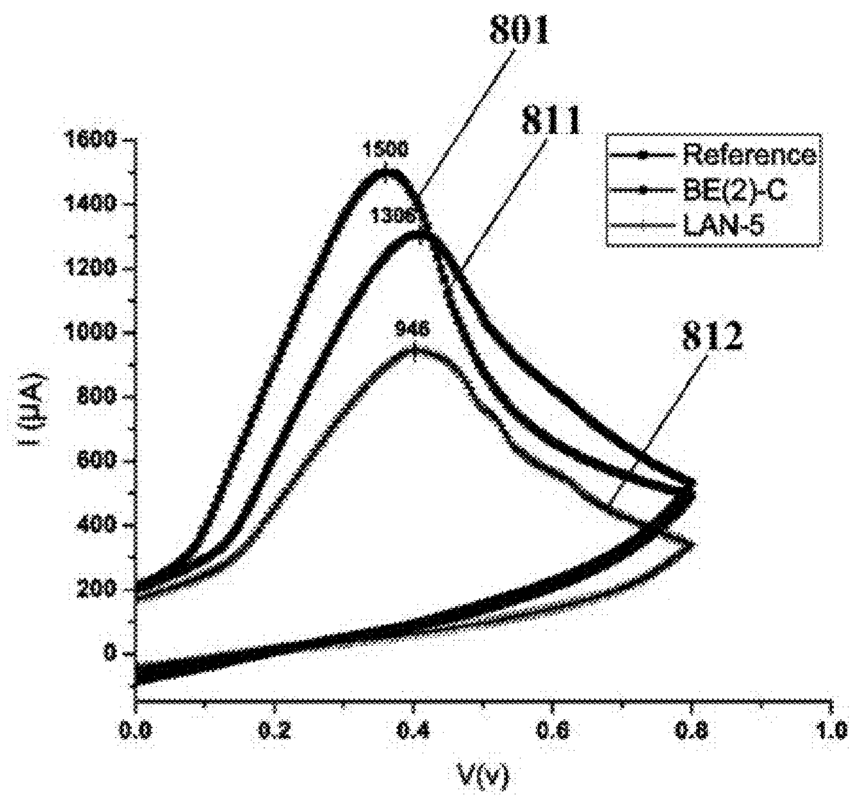
FIG. 8F illustrates the CV responses of the solution media of different normal and cancerous cell lines in various phenotypes for Neuron (BE(2)-C, LAN-5) cell lines in comparison with Reference diagram for $H_2O_2$ contained lactate solution with a lactate concentration of about 0.3 mM, consistent with one or more exemplary embodiments of the present disclosure.
Figure 8G:
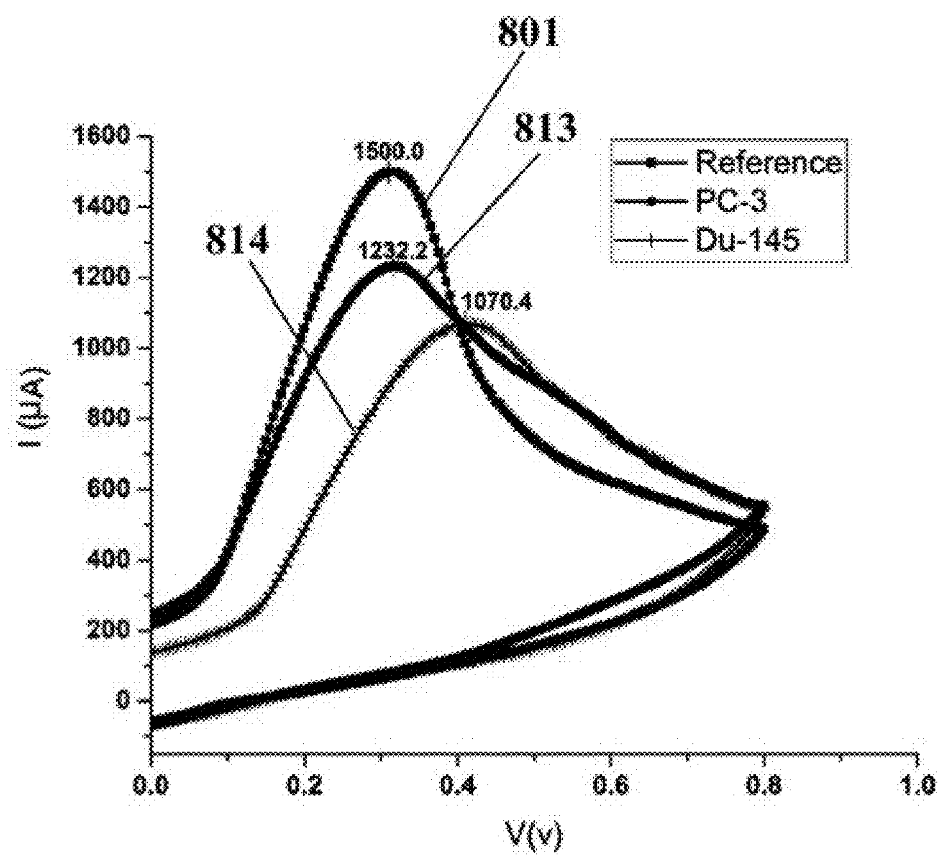
FIG. 8G illustrates the CV responses of the solution media of different normal and cancerous cell lines in various phenotypes for Prostate (PC-3, Du-145) cell lines in comparison with Reference diagram for $H_2O_2$ contained lactate solution with a lactate concentration of about 0.3 mM, consistent with one or more exemplary embodiments of the present disclosure.

FIGS. 8A-8G shows the CV responses of the solution media of different normal and cancerous cell lines in various phenotypes including Colon (COR-L 105 802, SW-480 803, HT-29 804) in FIG. 8A, Hematopoietic (1301 805, LCL-PI 1 806) in FIG. 8B, Liver (HEP G2 807) in FIG. 8C, Lung (QU-DB 808, MRC-5 809) in FIG. 8D, Mouth (KB 810) in FIG. 8E, Neuron (BE(2)-C, LAN-5) in FIG. 8F, and Prostate (PC-3 813, Du-145 814) in FIG. 8G cell lines in comparison with Reference diagram 801 for $H_2O_2$ contained lactate solution with a lactate concentration of about 0.3 mM, consistent with one or more exemplary embodiments of the present disclosure. The current peaks in cancerous samples were observably increased. The $H_2O_2$ based oxidative peaks of cancer media solutions were sharper than that in normal cells. Grade dependent increase was observed in $H_2O_2$ peaks of cancer cells with sharp difference between normal and cancer phenotypes in all of the cell lines. This reveal the increased hypoxia glycolysis in cancer cells with respect to that in normal cells. A great correlation was observed between the cells' phenotypes and their lactate based $H_2O_2$ electrochemical responses.

Example 5: In Vitro Diagnosis of Cancer in Samples by Electrochemical Tracking of Hypoxia Glycolysis in Secretion of the Samples In this example, the electrochemical responses of 6 breast tissues removed by biopsy (core needle biopsy (CNB)) or surgery from 6 of suspicious patients to cancer were analyzed using exemplary CNT based electrochemical chip. The size of the removed samples was similar (with the non-dehydrated weight of about 25 mg). The electrochemical responses were compared with cytopathological analysis done by Hematoxylin and Eosin (H & E) staining of the 6 breast tissues. Each resected sample was maintained in RPMI for about 24 hours before analyzing by exemplary CNT based electrochemical chip to be ensured from the lactate release in hypoxic tumors. Before pathological assaying, each resected sample was fixed in Formaline. For electrochemical analysis of hypoxia glycolysis in secretion of the samples, live spices from CNB or surgically removed samples were cut in similar specimens and directly transferred through sensing wells of exemplary CNT based electrochemical chip containing RPMI-1640 without any preprocessing. About 24 hours after maintaining the samples in incubator, about 200 μl of the culture media was dropped to individual sensing wells and the cathodic current of electrochemical responses of $H_2O_2$ were recorded in CV profile.

Figure 9A:
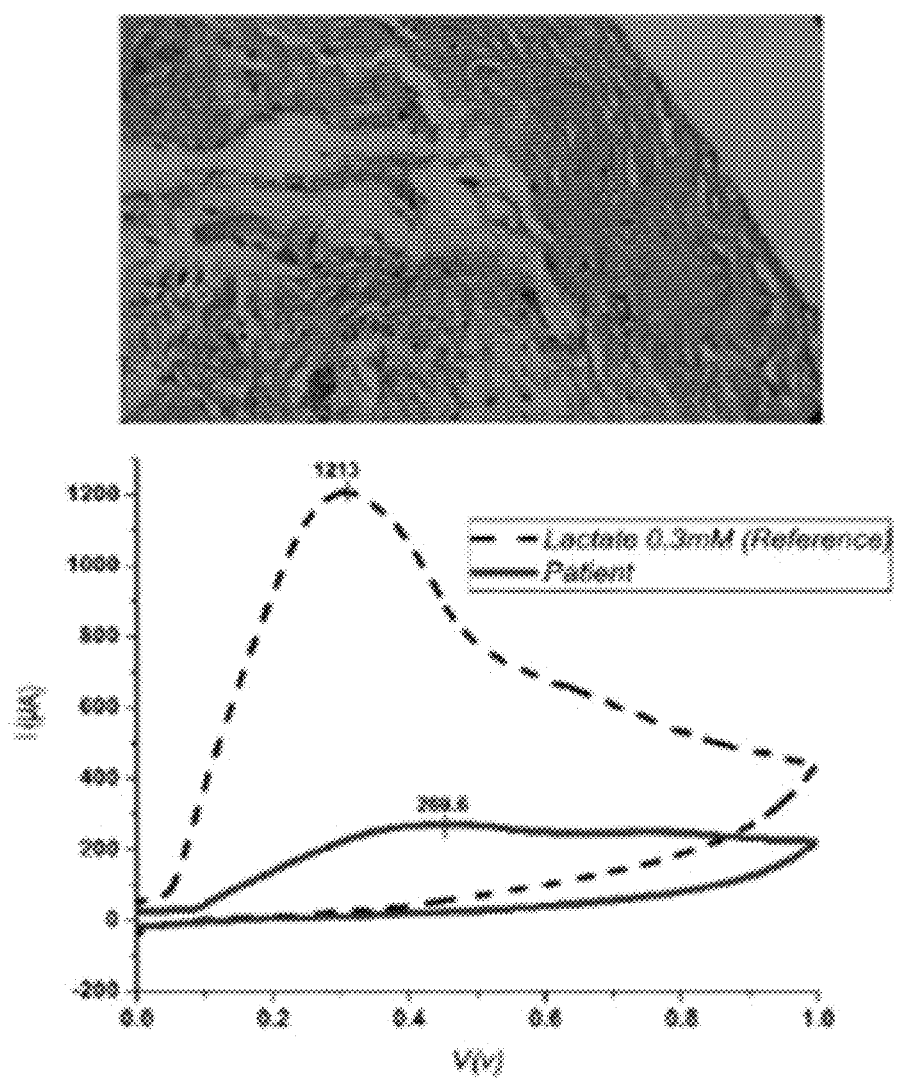
FIGS. 9A-9F illustrate the cytopathological results (top side) and electrochemical responses (bottom side) of the breast tissues removed by biopsy or surgery from 6 suspicious patients to cancer, consistent with one or more exemplary embodiments of the present disclosure.
Figure 9B:
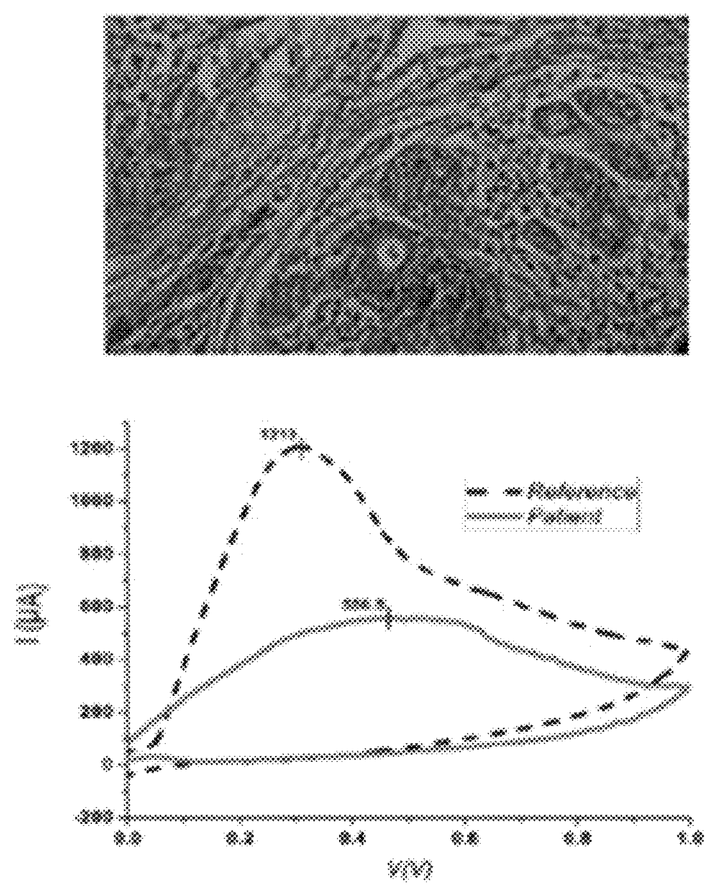
Figure 9C:
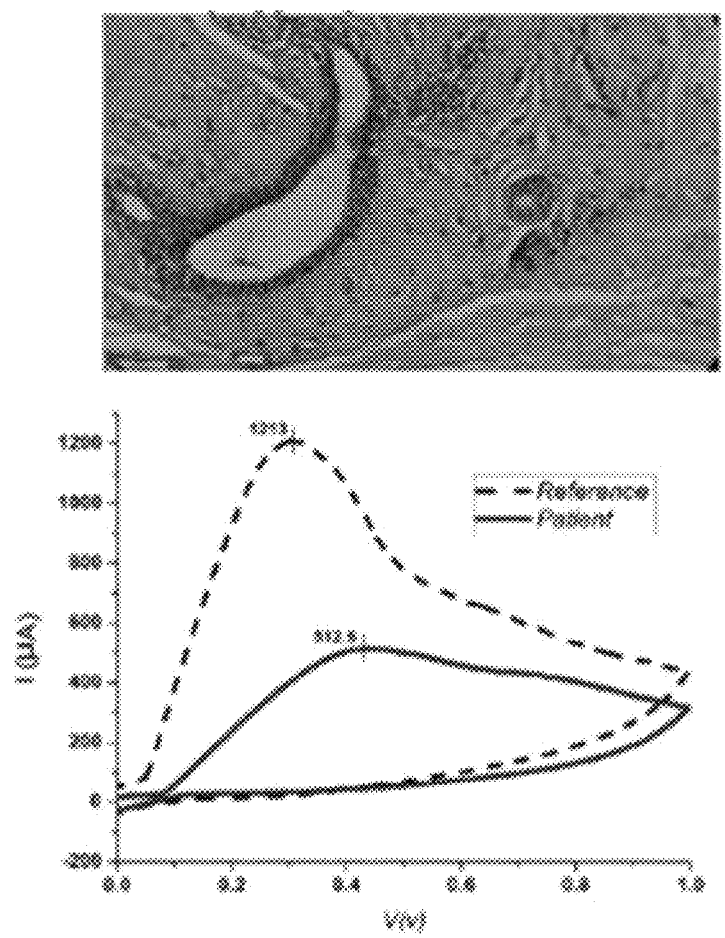
Figure 9D:
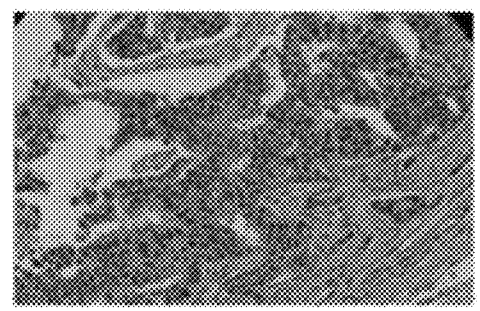
Figure 9D:
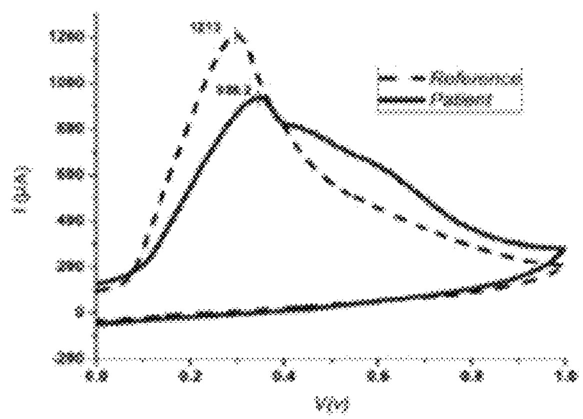
Figure 9E:
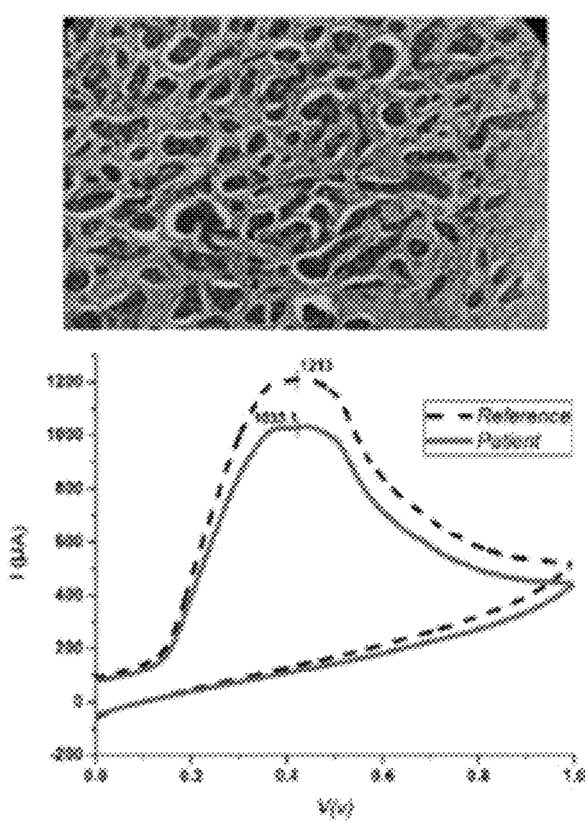
Figure 9F:
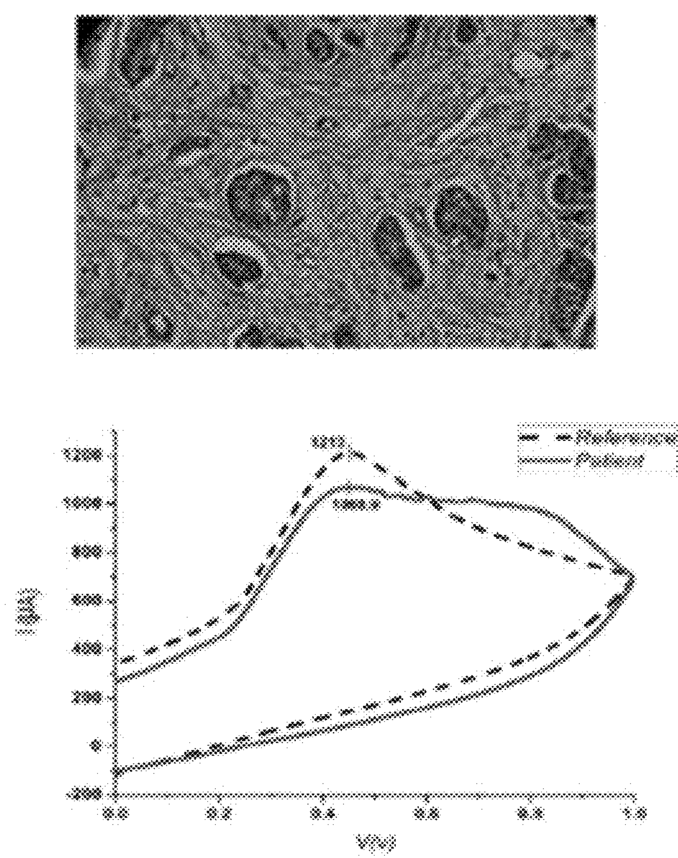

FIGS. 9A-9F show the cytopathological results (H&E images) (top side) and electrochemical responses (bottom side) of the breast tissues removed by biopsy or surgery from 6 suspicious patients to cancer, consistent with one or more exemplary embodiments of the present disclosure. The electrochemical responses were calibrated based on the reference $H_2O_2$ contained lactate solution with a lactate concentration of about 0.3 mM as used for cell lines in EXAMPLE 4 above. The intensity of oxidation peak and released electrons strongly correlated to the lactate produced by hypoxia glycolysis in cancer cells. A well correlation could be observed between increased $H_2O_2$ dependent current peak and cancer transformed morphology of the tissues. A great match observed between the quantified electrochemical response and pathological result of the samples in which the normal and hyperplasic tissues expressed low levels of $H_2O_2$ related current peak meanwhile the cancerous tissues exhibited high levels of $H_2O_2$ related electrochemical peaks. Accordingly, FIGS. 9A-9C show results obtained from non-cancerous samples and FIGS. 9D-9F show results obtained from cancerous samples.

Figure 10:
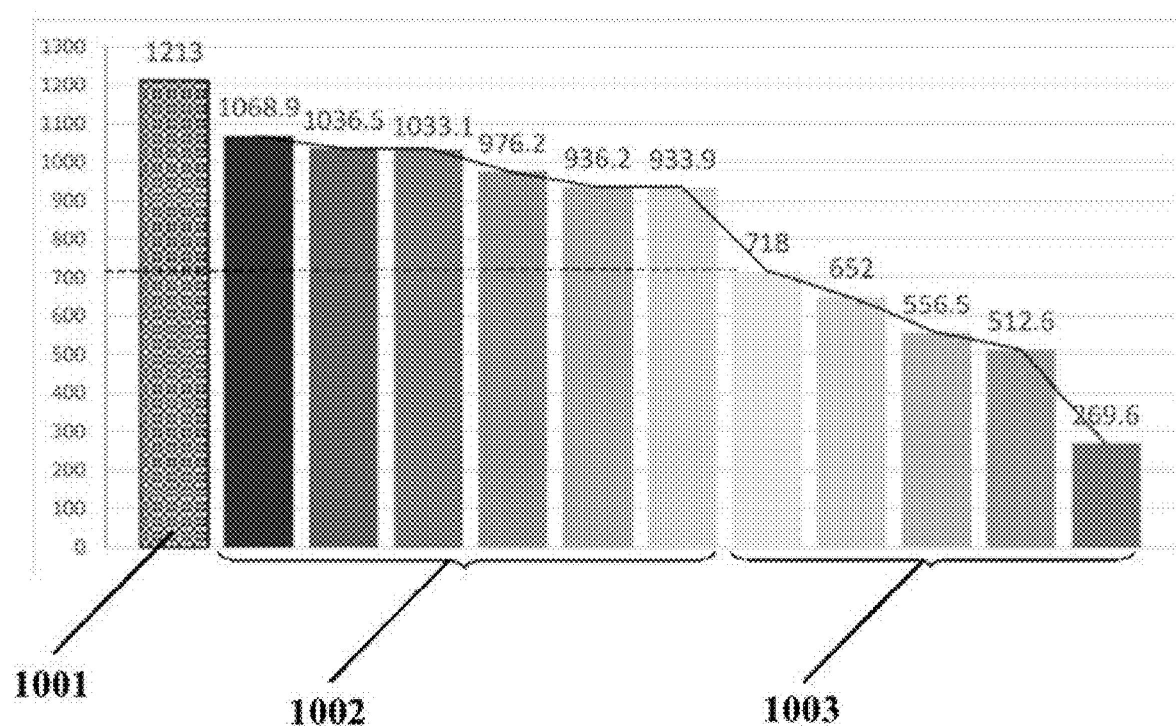
FIG. 10 illustrates a columnar diagram of electrochemical responses of the breast tissues removed by biopsy or surgery from 11 suspicious patients to cancer, consistent with one or more exemplary embodiments of the present disclosure.

Similar electrochemical responses of 5 more samples, including live spices from CNB or surgically removed samples, were obtained using exemplary CNT based electrochemical chip. FIG. 10 shows a columnar diagram of electrochemical responses of the breast tissues removed by biopsy or surgery from 11 suspicious patients to cancer, consistent with one or more exemplary embodiments of the present disclosure. Referring to this figure, two regimes 1002 and 1003 of responses were achieved due to the trace of hypoxia glycolysis based on LADH in comparison with a reference state 1001 of a $H_2O_2$ contained lactate solution with a lactate concentration of about 0.3 mM. In regime 1 indicated by 1002, the oxidation peaks were ranged from about 933.9 μA to about 1068.9 μA, and in regime 2 indicated by 1003, the oxidation peaks were ranged from about 269.6 μA to about 718 μA. The pathological results showed a well correlation with this determination. The samples presented high levels of hypoxia related oxidative peaks (categorized in regime 1) were verified as cancer in their H&E assays. Nests of distinguished tumoral cells in H&E images of those patients could be observed in FIGS. 9D-9F. Such responses were observed in the $H_2O_2$ contained lactate solution with the concentration of more than about 0.05 mM (FIG. 6B). Samples with low levels of lactate (regime2) were diagnosed as non-cancer with different types of benign cancer patients such as hyperplasia (peak: 556.5 μA) in FIG. 9B, lactational changes (peak: 718 μA), and so on. These electrochemical responses were equal to the peak determined in $H_2O_2$ contained lactate solution with the concentration of less than about 0.025 mM (FIG. 6B). Comparative columnar diagram presented in FIG. 10 would elaborate the difference in lactate based electrochemical response between normal and cancer tissues.

Example 6: Standard Colorimetric Lactate Assay Kit

As the released $H_2O_2$ concentration have a direct correlation with lactae concentration, to further investigate the accuracy of exemplary electrochemical method described above, the results of both cell lines (described in EXAMPLE 4) and patients' samples (described in EXAMPLE 5) were compared by standard colorimetric lactate assay kit. Although this method is so time consuming and expensive with complicated multi sequential steps, it was conducted to check the reliability of lactate concentration based cancer diagnosis measured by exemplary CNT based electrochemical chip. Comparative responses versus reference $H_2O_2$ contained lactate solution for both electrochemical and Lactate Kit assays are presented in Table 1 and Table 2.

TABLE 1

Comparative responses of CNT based electrochemical chip and standard Lactate Kit Assay on 4 different phenotypes of Breast cell lines.

| Cell line | Electrochemical sensor: Relative Current (%) | Lactate kit: Relative Lactate Concentration (%) |
|---|---|---|
| Reference lactate solution | 100 | 100 |
| MCF 10A | 31.1 | 31.1 |
| MCF-7 | 52.9 | 56.3 |
| MDA-MB-231 | 69.5 | 70.9 |
| MDA-MB-468 | 91.5 | 91.5 |

TABLE 2

Diagnostic results of 11 patients suspicious to breast cancer determined by H&E, Lactate kit, and the cathodic peaks of released $H_2O_2$ from the cells measured by CNT based electrochemical chip assays, respectively.

| Patient ID | Type of Tissue | H & E Result | Lactate Kit Result (%) | CNT Electrochemical Sensor (%) |
|---|---|---|---|---|
| Reference lactate | — | — | 100 | 100 |
| 1 | Normal | Non Cancer | 22.2 | 22.2 |
| 2 | Normal | Left Hyper Plasy | 42.3 | 42.3 |
| 3 | Normal | Lactational Change | 59.1 | 59.2 |
| 4 | Normal | Adenosis benign glandular prolifration | 53.8 | 53.7 |
| 5 | Normal | Hyperplasy and inflammation | 45.9 | 45.9 |
| 6 | Suspicious to Cancer | Lympho vascular invasion | 88.1 | 88.2 |
| 7 | Suspicious to Cancer | Cancer | 77.2 | 77.2 |
| 8 | Suspicious to Cancer | Cancer | 85.5 | 85.4 |
| 9 | Suspicious to Cancer | Cancer | 80.5 | 80.5 |
| 10 | Suspicious to Cancer | Cancer | 85.1 | 85.2 |
| 11 | Suspicious to Cancer | Cancer | 62 | 62.2 |

A correlation was observed between the responses of the CNT based electrochemical chip and kit which revealed the accuracy of CNT based electrochemical chip in lactate based cancer detection as shown in Table 1 and Table 2. The raw values recorded by Lactate kit and electrochemical sensing wells were presented in these tables. In summary, tracing the hypoxia glycolysis (correlated with lactate concentration) in the interstitial fluid of biopsy sample by electrochemical assay with suitable electrode (such as CNT) exhibited a high correlation with their pathological states and may be used as a new method in cancer diagnosis.

Example 7: Integrated Assay on the Tip of the Needles of Cancer Diagnostic Probe (CDP) for Real-Time Cancer Detection Both In Vitro and In Vivo To extend the application of exemplary label free electrochemical method of the present disclosure in real-time and precise detection of the tumor tissues during interventional sonography or surgery, exemplary CDP fabricated by growth of carbon nanostructures on the tip of the sterile steel needles as described in EXAMPLE 2 was used herein. Such integrated system contains three carbonated needles as working electrode (WE), counter electrode (CE), and reference electrode (RE). The needles were rinsed by PBS, Ethanol 70% and DI water followed by drying in $N_2$ ambient and UV sterile to prevent from any detachment and remaining the residues of the nanotubes in the tissue. CV responses were taken immediately after squeeze of exemplary CDP into the breast cancerous and normal tissues that indicated sharp increase in the current peak of the CDP with CNT covered electrodes interacted by cancer tissue. The important point is that the diagnosis was completed in live time based on monitoring the lactate concentration of the tissues inner domain.

Figure 11A:
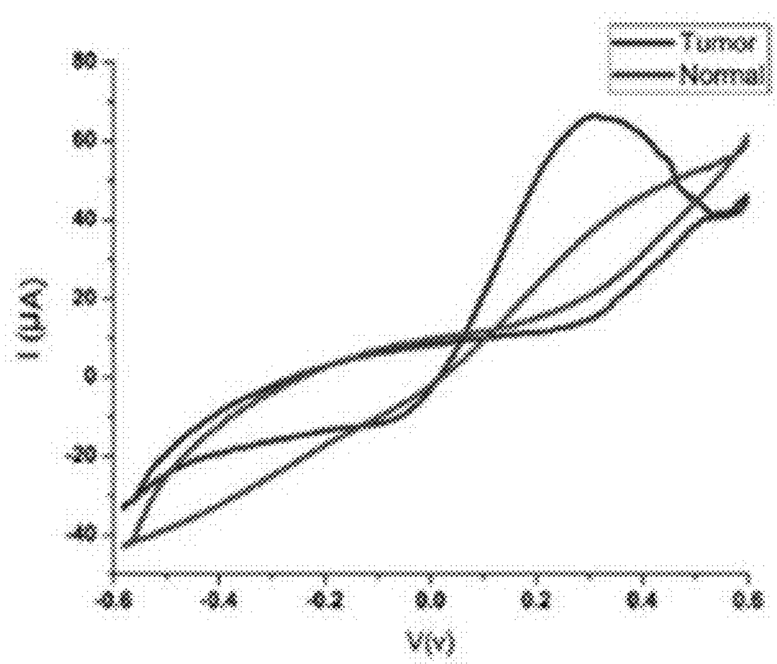
FIG. 11A illustrates CV response of exemplary CDP with all three needles covered by VAMWCNTs immediately after connection to the tissues, consistent with one or more exemplary embodiments of the present disclosure.

FIG. 11A shows CV response of exemplary CDP with all three needles covered by VAMWCNTs immediately after connection to the tissues, consistent with one or more exemplary embodiments of the present disclosure. It may be observed that reversible shapes with symmetric anodic and catholic peaks were obtained in CV responses. Distinguishable response between normal and cancer tissues may be observed.

Figure 11B:
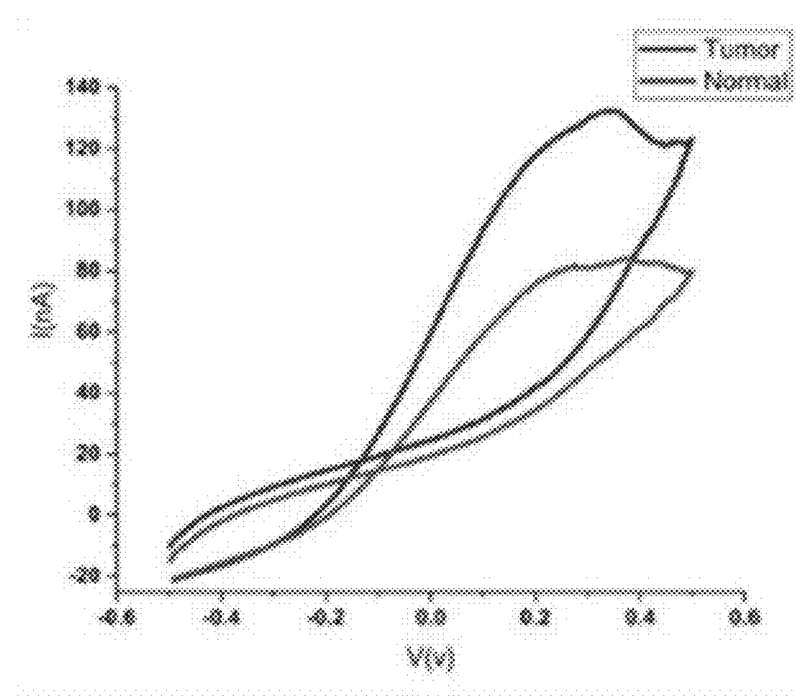
FIG. 11B illustrates CV response of exemplary CDP with only working electrode covered by VAMWCNTs immediately after connection to the tissues, consistent with one or more exemplary embodiments of the present disclosure.

FIG. 11B shows CV response of exemplary CDP with only working electrode covered by VAMWCNTs immediately after connection to the tissues, consistent with one or more exemplary embodiments of the present disclosure. Quality of the peaks were degraded when replacing the RE and CE by steel needle. The intensity and symmetry of the responses were degraded in the sensor with just CNT covered WE (CE and RE were steel needles).

Figure 11C:
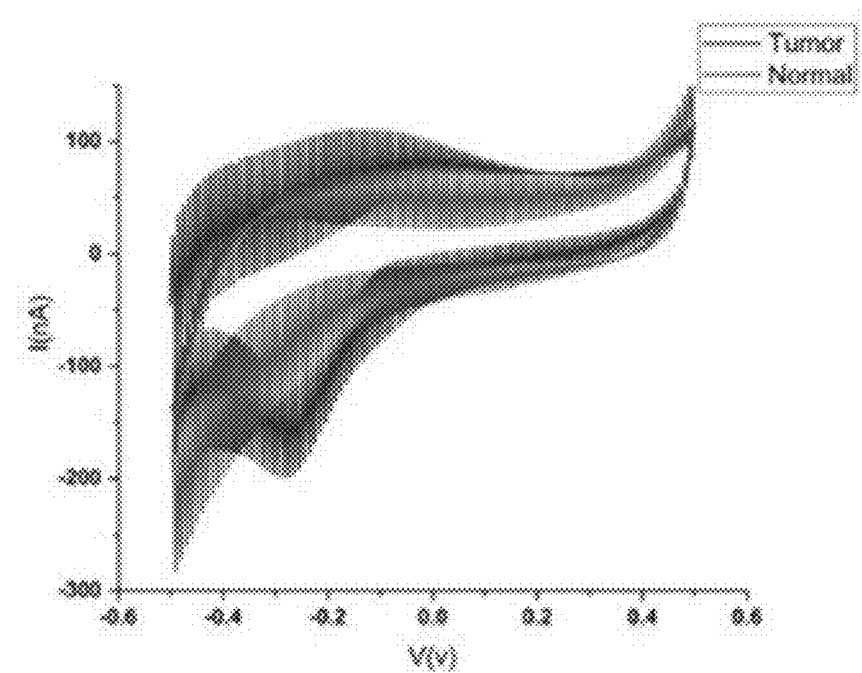
FIG. 11C illustrates CV response of exemplary CDP with non-CNT covered by needles immediately after connection to the tissues, consistent with one or more exemplary embodiments of the present disclosure.

FIG. 11C shows CV response of exemplary CDP with non-CNT covered by needles immediately after connection to the tissues, consistent with one or more exemplary embodiments of the present disclosure. There may be observed a noisy response without any distinguishable electrochemical peak. When all of the electrodes were non CNT covered needles, the responses were completely degraded and not distinguishable between normal and cancer tissues. This revealed the important role of CNT in selective interaction and charge transfer from the $H_2O_2$ released during transformation of lactate to pyruvate.

Figure 12A:
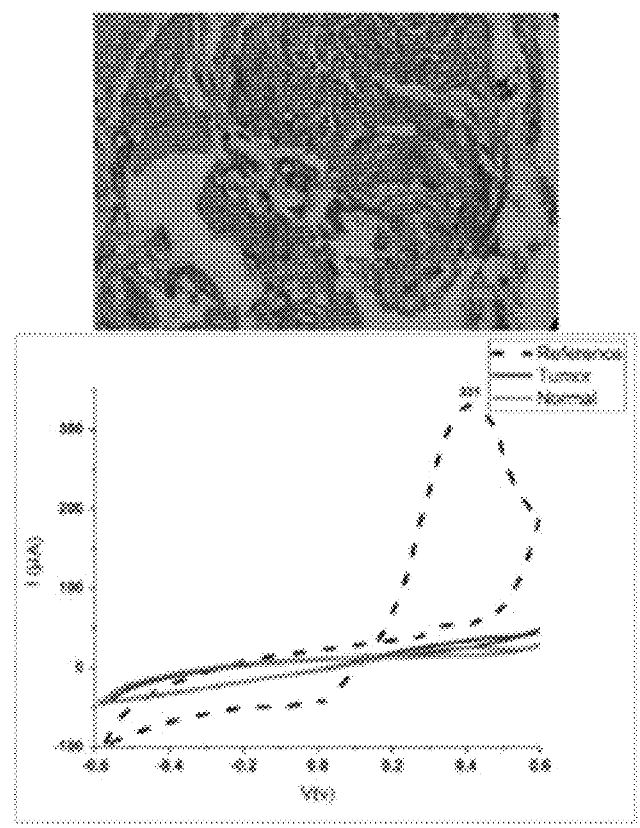
FIGS. 12A-12E illustrate CV responses recorded by exemplary CDP (needle based electrochemical sensor) from the resected tissues from five patients among 50 individual patients suspicious to breast cancer (bottom side) in comparison with images obtained by conventional pathological methods (H&E) (top side), consistent with one or more exemplary embodiments of the present disclosure.
Figure 12B:
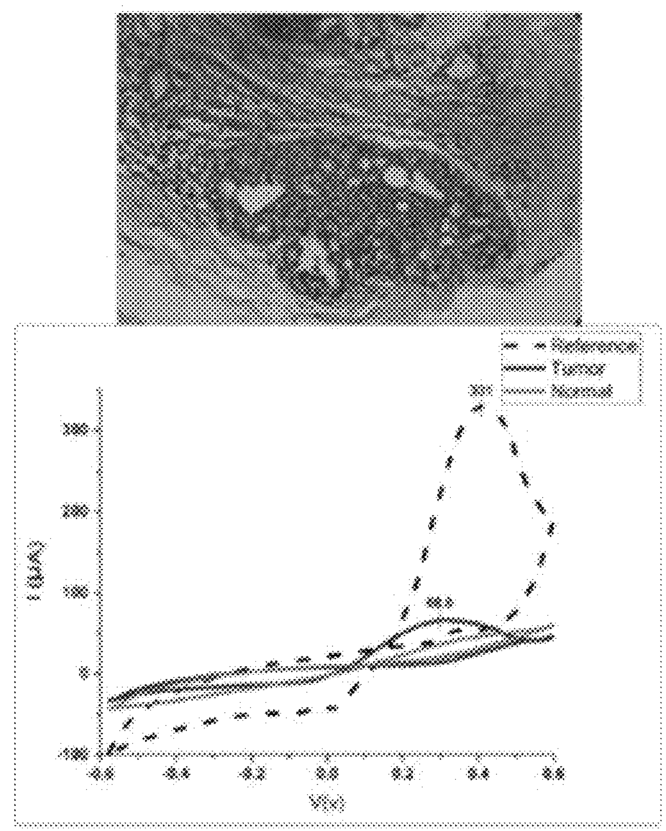
Figure 12C:
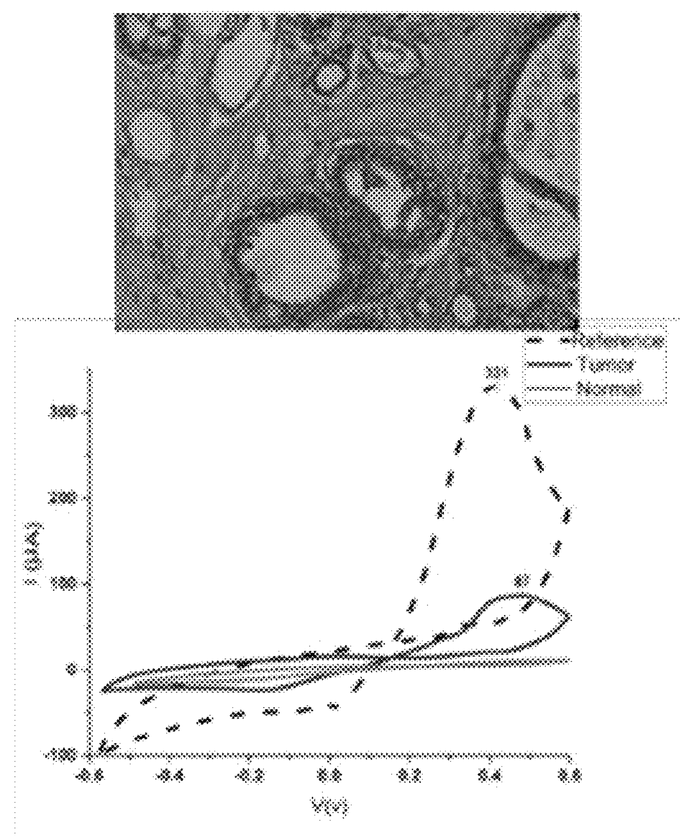
Figure 12D:
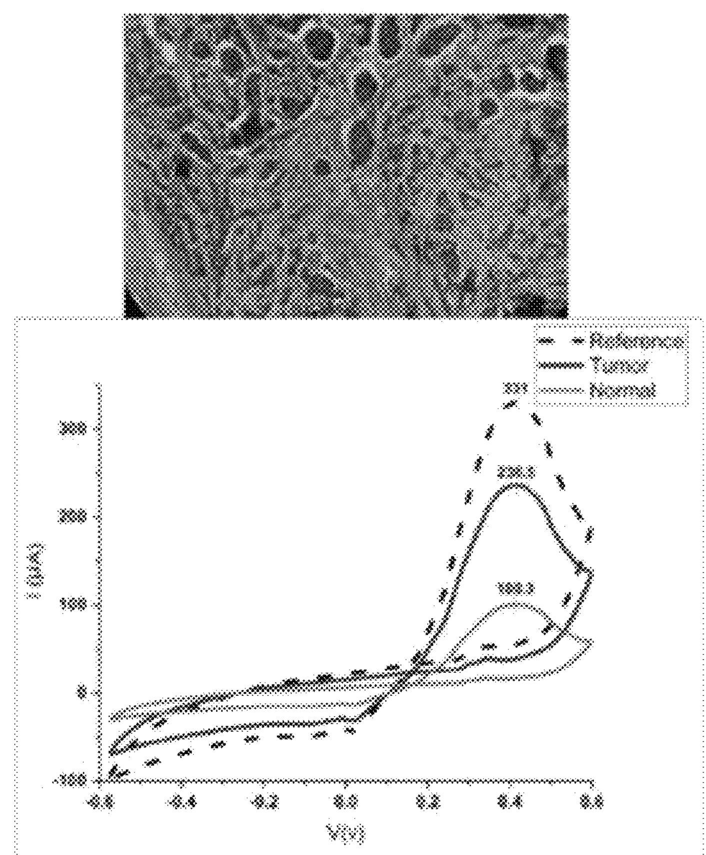
Figure 12E:
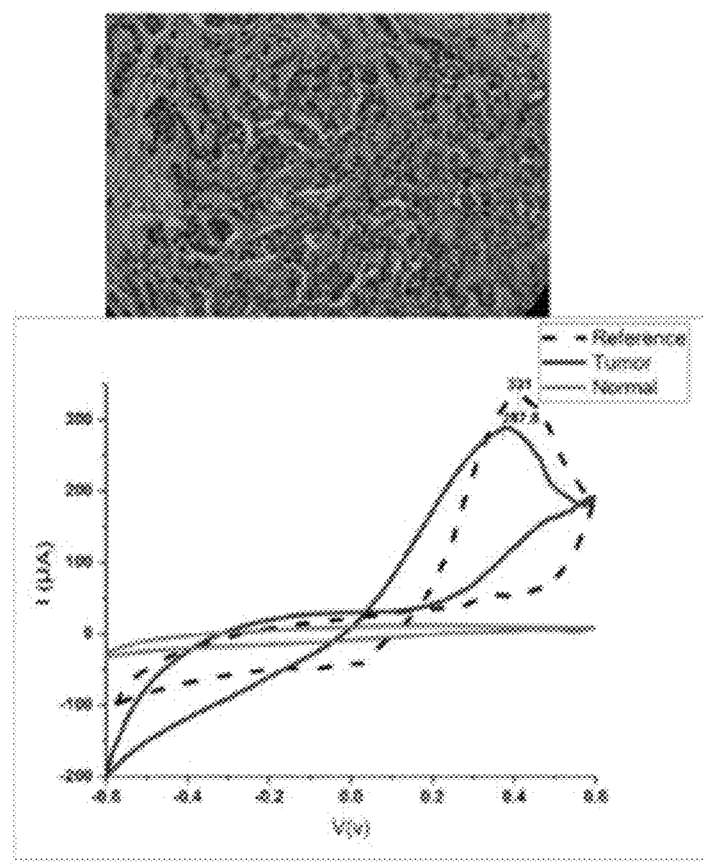

FIGS. 12A-12E show CV responses recorded by exemplary CDP (needle based electrochemical sensor) from the resected tissues from five patients among 50 individual patients suspicious to breast cancer at the bottom side of FIGS. 12A-12E in comparison with images obtained by conventional pathological methods (H&E) at the top side of FIGS. 12A-12E, consistent with one or more exemplary embodiments of the present disclosure. Patients respective to FIGS. 12A-12C have normal/non-cancerous (FIG. 12A), hyperplasic (FIG. 12B), and adenosis glandular proliferative tissues (FIG. 12C). Patients respective to FIGS. 12D and 12E have cancer tissues. Electrochemical current peaks of cancer tissues are sharply (more than about 150 μm) higher than benign ones with a strong correlation by the abundance of distributed cancer cells. The CV responses recorded from the normal and cancer tissues of these 50 individual patients by CNT covered needle sensors (CDP) greatly detected the hypoxic glycolysis just in cancerous samples due to cathodic peaks of $H_2O_2$ (FIGS. 12A-12E). Meanwhile, while the response time of CDP was less than about 1 minute after the tissue resection, diagnosis by conventional pathological methods (H&E) requires at least several hours for sample fixation and staining procedures. The ratio of cathodic peaks of reference $H_2O_2$ contained lactate solution vs. non-cancerous tissues were more than three times (FIGS. 12A-12C) while such ratio was less than one time in cancerous tissues (FIGS. 12D and 12E).

Table 3 shows the results recorded by exemplary CDP in comparison with the results obtained by H&E analysis from live resected tissues of 50 patients suspicious to breast cancer. They exhibited great correlations with the pathological results of the samples assayed by H&E method.

TABLE 3

Results recorded by exemplary CDP in comparison with the results obtained by H&E analysis from live resected tissues of 50 patients suspicious to breast cancer.

| Patient ID | Oxidation Current Peaks (μA) | CDP (Cancer) | H&E (Cancer) |
|---|---|---|---|
| 1 | 0 | Negative | NO |
| 2 | 46.6 | Negative | NO |
| 3 | 87 | Negative | NO |
| 4 | 316.5 | Positive | YES (Cancer 90%, Normal 10%) |
| 5 | 287.8 | Positive | YES (Cancer 90%, Normal 10%) |
| 6 | 22 | Negative | NO |
| 7 | 142.3 | Positive | YES (Cancer 30%, Normal 70%) |
| 8 | 150 | Positive | YES (Cancer 30%, Normal 70%) |
| 9 | 300 | Positive | YES (Cancer 90%, Normal 10%) |
| 10 | 13 | Negative | NO |
| 11 | 0 | Negative | NO |
| 12 | 101.5 | Positive | YES (Cancer 30%, Normal 70%) |
| 13 | 180.2 | Positive | YES (Cancer 60%, Normal 40%) |
| 14 | 289.4 | Positive | YES (Cancer 90%, Normal 10%) |
| 15 | 302 | Positive | YES (Cancer 90%, Normal 10%) |
| 16 | 274.2 | Positive | YES (Cancer 90%, Normal 10%) |
| 17 | 0 | Negative | NO |
| 18 | 142.8 | Positive | YES (Cancer 30%, Normal 70%) |
| 19 | 80 | Negative | NO |
| 20 | 32.5 | Negative | NO |
| 21 | 200 | Positive | YES (Cancer 60%, Normal 40%) |
| 22 | 188.2 | Positive | YES (Cancer 60%, Normal 40%) |
| 23 | 264.5 | Positive | YES (Cancer 90%, Normal 10%) |
| 24 | 23 | Negative | NO |
| 25 | 179.5 | Positive | YES (Cancer 60%, Normal 40%) |
| 26 | 55.2 | Negative | NO |
| 27 | 52 | Negative | NO |
| 28 | 77 | Negative | NO |
| 29 | 0 | Negative | NO |
| 30 | 201 | Positive | YES (Cancer 60%, Normal 40%) |
| 31 | 75.6 | Negative | NO |
| 32 | 155.8 | Positive | YES (Cancer 30%, Normal 70%) |
| 33 | 99.5 | Positive | YES (Cancer 30%, Normal 70%) |
| 34 | 305.5 | Positive | YES (Cancer 90%, Normal 10%) |
| 35 | 297.7 | Positive | YES (Cancer 90%, Normal 10%) |
| 36 | 112 | Positive | YES (Cancer 30%, Normal 70%) |
| 37 | 17.8 | Negative | NO |
| 38 | 40 | Negative | NO |
| 39 | 73 | Negative | NO |
| 40 | 290 | Positive | YES (Cancer 90%, Normal 10%) |
| 41 | 90 | Positive | YES (Cancer 30%, Normal 70%) |
| 42 | 330 | Positive | YES (Cancer 90%, Normal 10%) |
| 43 | 197.5 | Positive | YES (Cancer 30%, Normal 70%) |
| 44 | 77.5 | Negative | NO |
| 45 | 25 | Negative | NO |
| 46 | 266.2 | Positive | YES (Cancer 90%, Normal 10%) |
| 47 | 0 | Negative | NO |
| 48 | 102.5 | Positive | YES (Cancer 30%, Normal 70%) |
| 49 | 310 | Positive | YES (Cancer 90%, Normal 10%) |
| 50 | 259.3 | Positive | YES (Cancer 90%, Normal 10%) |

Figure 13:
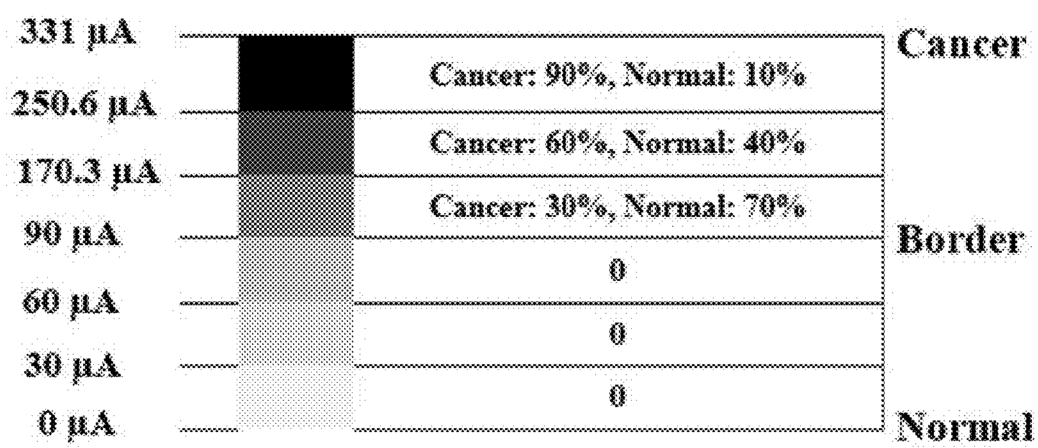
FIG. 13 illustrates a summary of categorized regimes of CV responses recorded by exemplary CDP from the resected tissues from five patients among 50 individual patients suspicious to breast cancer representing CV regimes along a spectrum from a completely non-cancerous state to cancerous state, consistent with one or more exemplary embodiments of the present disclosure.

FIG. 13 shows a summary of categorized regimes of CV responses recorded by exemplary CDP from the resected tissues from five patients among 50 individual patients suspicious to breast cancer that were presented in Table 3. It represents CV regimes along a spectrum from a completely non-cancerous state to cancerous state, consistent with one or more exemplary embodiments of the present disclosure. It may be seen that if the $H_2O_2$ cathodic peak (equal to oxidation current peak) of exemplary CV response recorded by exemplary CDP from a patient is less than 90 μA, the tissue is in non-cancerous state. On the other hand, if the CV response recorded by exemplary CDP from the tissue is in a range more than about 95 μA, there exists a cancerous state which may be more intensified by increasing the oxidation current peak. A range of oxidation current peak between 90 μA and 95 μA is the border range.

Example 8: In Vivo Analysis of Observable Tumor with Histologically Distinct Cancer Margin Before any Mastectomy To determine if CDP would in real time identify an observable tumor in vivo, about $2.3\times10^6$ 4T1-derived cancer cells were implanted into the back of 10 female BALB/C mice, and the mice were maintained in individual groups with similar size of formed tumors with sharp histologically distinct patterns. After about 10 days, individual CDPs were externally squeezed into their cancerous and normal regions had been specified by sonography. The space between each assayed regions was about 3 mm. Also the mice under body were connected to ground potential such as done for any patient in surgery room.

Figure 14A:
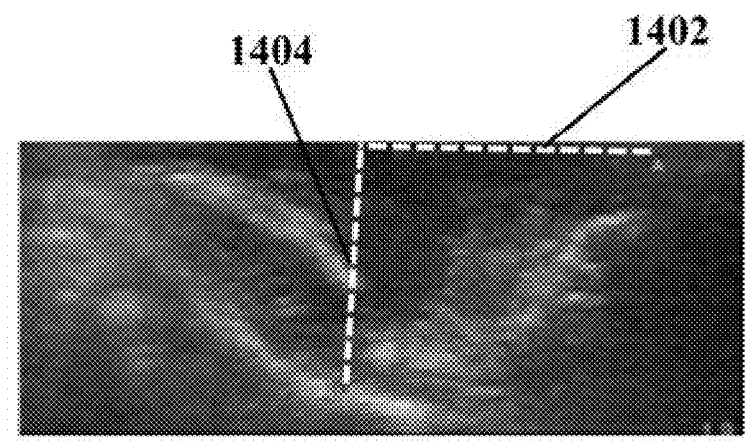
FIG. 14A illustrates a sonography image from a tumor side taken from an exemplary mouse tumorized by 4T1 breast cancer cell lines, consistent with one or more exemplary embodiments of the present disclosure.

FIG. 14A shows a sonography image from a tumor side taken from an exemplary mouse tumorized by 4T1 breast cancer cell lines, consistent with one or more exemplary embodiments of the present disclosure. A tumor with average sizes with a length 1402 of about 2.24 cm and another length 1404 of about 1.60 cm could be observed in sonography image.

Figure 14B:
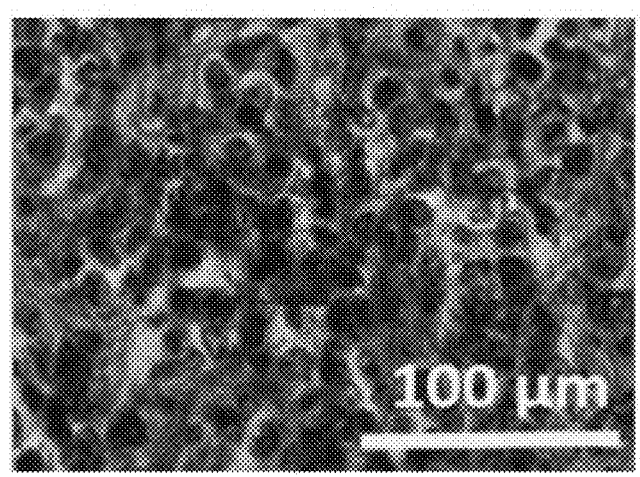
FIG. 14B illustrates H&E image from the tumor side taken from exemplary tumorized mouse by 4T1 breast cancer cell lines, consistent with one or more exemplary embodiments of the present disclosure.
Figure 14C:
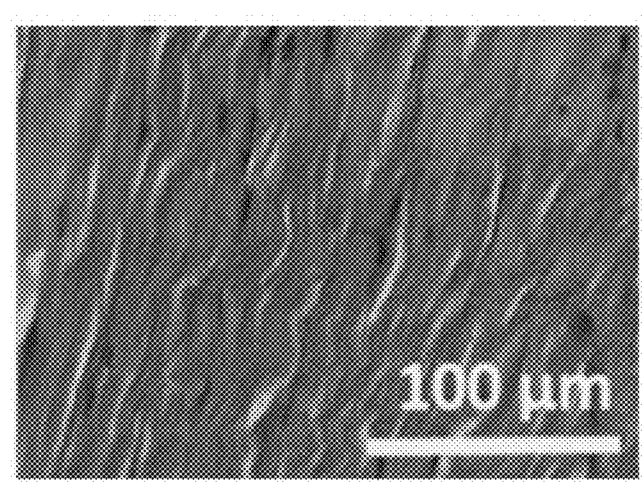
FIG. 14C illustrates H&E image from a normal/healthy side taken from exemplary tumorized mouse by 4T1 breast cancer cell lines, consistent with one or more exemplary embodiments of the present disclosure.

FIG. 14B shows H&E image from the tumor side taken from exemplary tumorized mouse by 4T1 breast cancer cell lines, consistent with one or more exemplary embodiments of the present disclosure. FIG. 14C shows H&E image from a normal/healthy side taken from exemplary tumorized mouse by 4T1 breast cancer cell lines, consistent with one or more exemplary embodiments of the present disclosure.

Figure 14D:
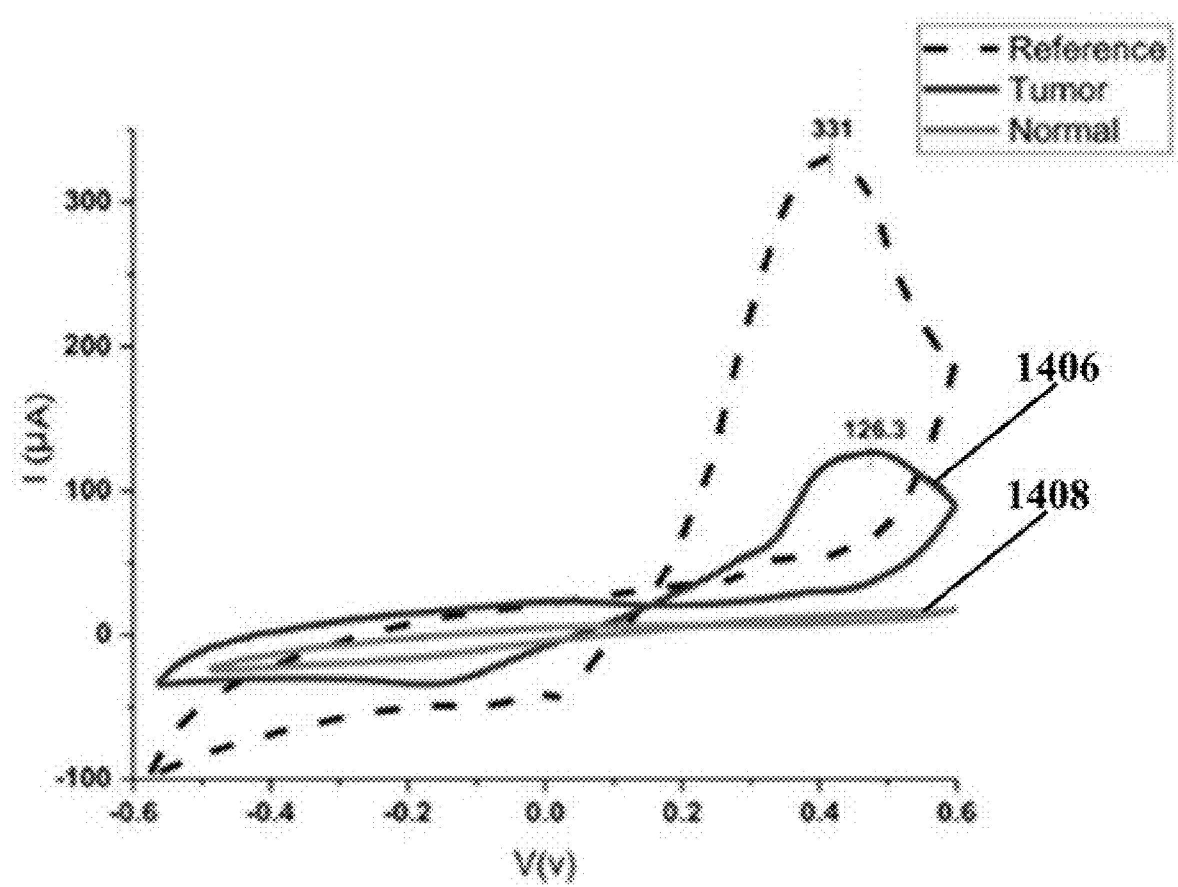
FIG. 14D illustrates CV diagrams of normal and tumor regions/sides of exemplary tumorized mouse by 4T1 breast cancer cell lines calibrated by a Reference CV diagram from $H_2O_2$ contained lactate solution with a lactate concentration of about 0.3 mM obtained using exemplary CDP, consistent with one or more exemplary embodiments of the present disclosure.

FIG. 14D shows CV diagrams of normal and tumor regions/sides of exemplary tumorized mouse by 4T1 breast cancer cell lines calibrated by a Reference CV diagram from $H_2O_2$ contained lactate solution with a lactate concentration of about 0.3 mM obtained using exemplary CDP, consistent with one or more exemplary embodiments of the present disclosure. It may be observed that the lactate related peaks were about 3 times higher in cancer region (CV diagram 1406 and FIGS. 14A and 14B) versus normal ones (CV diagram 1408 and FIG. 14C). Sharp lactate electrochemical peaks were observed in tumor locations by about three times higher current than that recorded from their normal regions To more clearly clarify the impact of $H_2O_2$ monitoring in tumor growth and progression, tumor size effects on $H_2O_2$ related electrochemical peaks recorded by CDP were compared. A distinguishable increasing regime was observed in the intensity of current peak through increment in the tumor size. Moreover, Histopathological images taken from the normal and cancer regions detected by CDP confirmed this result. Hyper chromatic and irregular nucleus with increased nucleus/cytoplasm ratio may be observable in H&E images of cancer region.

Example 9: In Vivo Analyses of Suspicious Regions Before and During the Surgery

In this example, the ability of the CDP to distinguish suspicious regions to cancer in mice model was analyzed by the resolution of about 3 mm which could be translated to human model. Tissue samples that contained regions of invasive breast cancer adjacent to normal stroma were experimented.

Figure 15A:
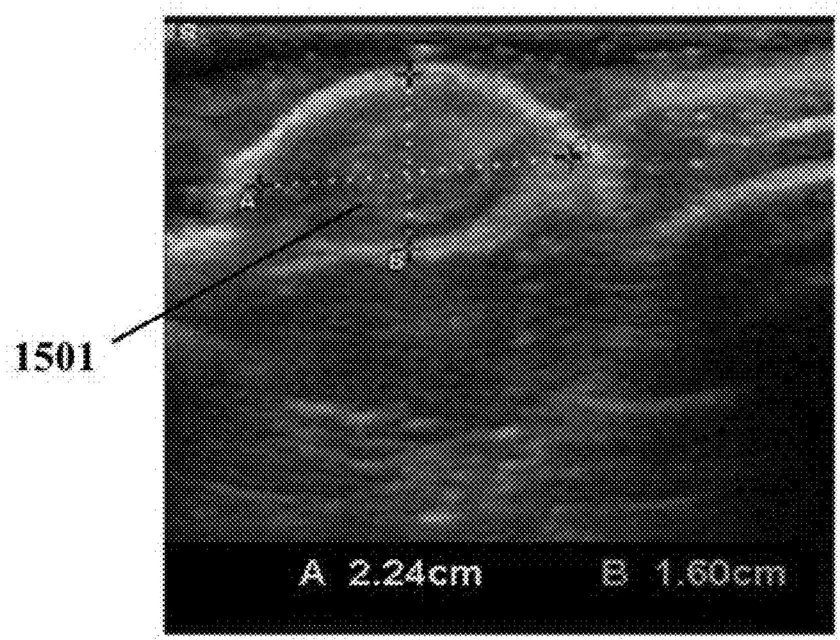
FIG. 15A illustrates a sonography image from a tumor taken from an exemplary mouse tumorized by 4T1 breast cancer cell lines, consistent with one or more exemplary embodiments of the present disclosure.

Five tumorized mice by 4T1 breast cancer cell lines were checked by sonography. FIG. 15A shows a sonography image from a tumor 1501 taken from an exemplary mouse tumorized by 4T1 breast cancer cell lines, consistent with one or more exemplary embodiments of the present disclosure. Approximate dimensions of the tumor could be observed in sonography image of FIG. 15A.

Figure 15B:
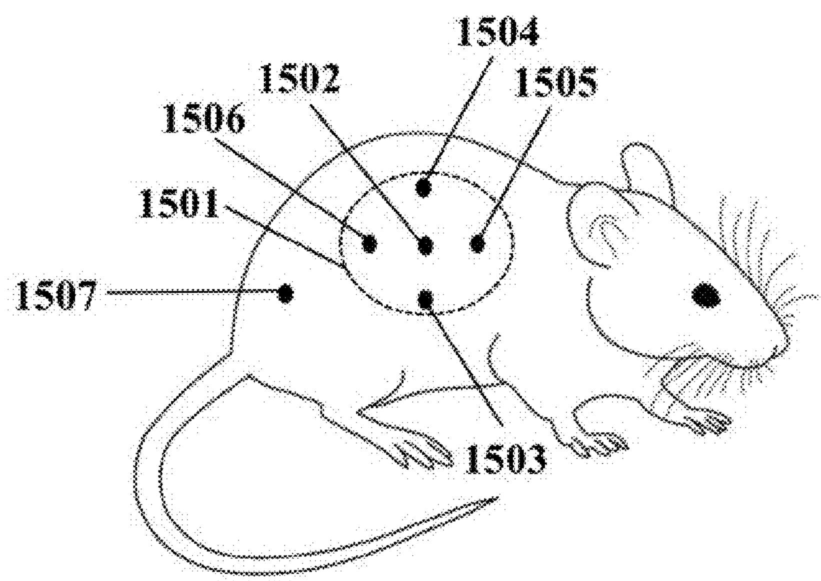
FIG. 15B illustrates exemplary six analyzed regions of an exemplary tumorized mouse among the exemplary five tumorized mice before surgery, consistent with one or more exemplary embodiments of the present disclosure.
Figure 15C:
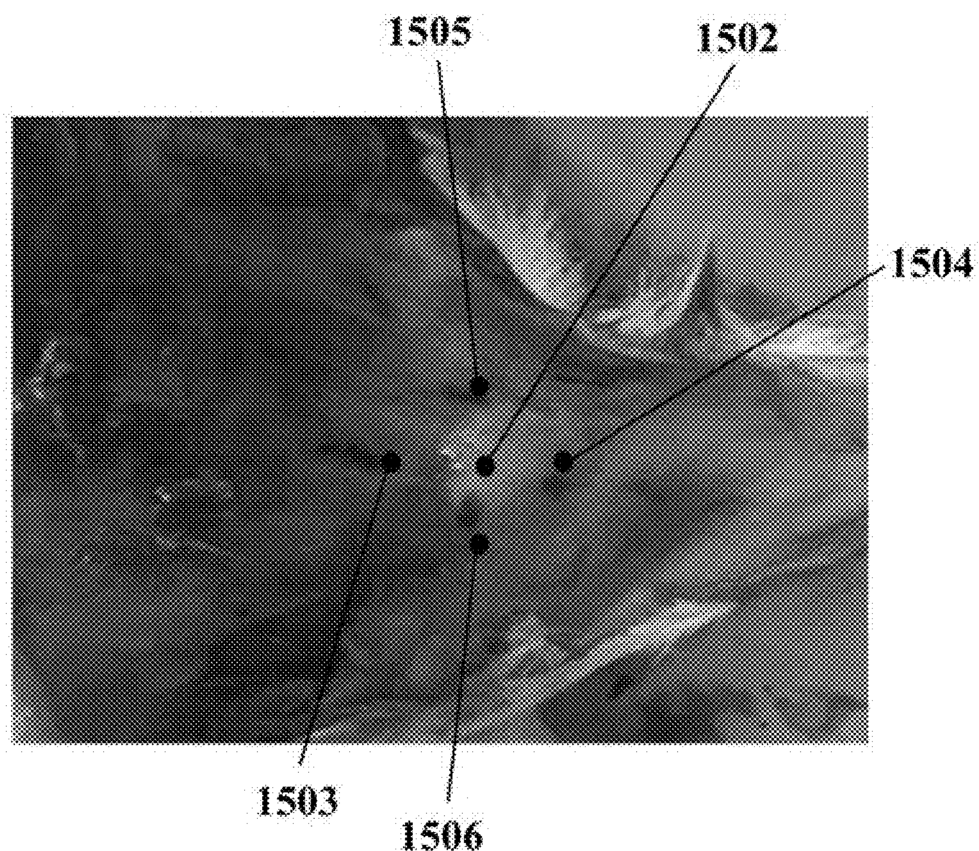
FIG. 15C illustrates exemplary six analyzed regions of an exemplary tumorized mouse among the exemplary five tumorized mice during surgery, consistent with one or more exemplary embodiments of the present disclosure.

Exemplary CDP was tested on tumor and suspicious regions of the five tumorized mice before (by squeezing through skin) and during the surgery on exemplary six regions. FIGS. 15B and 15C show exemplary six analyzed regions 1502-1507 of an exemplary tumorized mouse among the exemplary five tumorized mice before (FIG. 15B) and during surgery (FIG. 15C), consistent with one or more exemplary embodiments of the present disclosure. Six analyzed regions may include center 1502 of tumor 1501, left side 1503 of tumor 1501, right side 1504 of tumor 1501, upside 1505 of tumor 1501, bottom side 1506 of tumor 1501, and also an exemplary normal side 1507 far from tumor 1501 all depicted in FIGS. 15B and 15C were analyzed consecutively before and during surgery using a CDP with an about 3 mm distance between needle electrodes.

Moreover, frozen H&E assay was used and rechecked by IHC method to be ensure from the precision of CDP results with respect to standard protocols. A tissue section of the sample including exemplary six regions analyzed by exemplary CDP was subjected to frozen H&E staining processes and evaluated by the pathologist. Exemplary tumor 1501 containing suspicious regions was removed and sent for frozen pathology and the H&E images taken from the center 1502 of tumor 1501 as well as its posterior 1505, anterior 1506, right 1504 and left 1503 laterals with the distance of about 3 mm from the histologically distinct region, were demanded by the CDP results as presented in Table 4. The results of CDP before and during surgery exhibited a perfect correlation. Ki67 based IHC assay confirmed the normal state of R5 and cancer involvement in R3 as classifier reference.

TABLE 4

Results recorded by exemplary CDP before and during surgery in comparison with the results obtained by H&E analysis from six suspicious regions of an exemplary tumorized mouse.

| Region | CDP Before Surgery (Ox Current Peaks (μA)) | CDP During Surgery (Ox Current Peaks (μA)) | H&E frozen (Cancer) |
|---|---|---|---|
| 1502 (Center) | Positive (169.104) | Positive (178.621) | Yes (Cancer 90%, Normal 10%) |
| 1503 (Right) | Positive (94.773) | Positive (96.89) | Yes (Cancer 30%, Normal 70%) |
| 1504 (Left) | Positive (122.643) | Positive (122.8) | Yes (Cancer 60%, Normal 40%) |
| 1505 (Up) | Negative (30.397) | Negative (31.85) | No |
| 1506 (Bottom) | Negative (0) | Negative (0) | No |
| 1507 (Normal) | Negative (0) | Negative (0) | No |

As represented in Table 4, it was distinguished from H&E analyzes that center 1502 was diagnosed by frozen histopathology as cancer tissue, whereas regions 1505 and 1506 were diagnosed as normal stroma. Region 1504 was in the margin between the cancer and normal stroma tissue regions, presenting about 40% tumor tissue and about 60% normal stroma tissue. Region 1503 was a suspicious region without any tumor margins but the trace of distributed cancer cells would be observed between stroma. Tumoral cells would be distinguished due to their hyper chromic nuclei (triangular arrows in H&E images of regions 1503 and 1504). Tabled result shows the CDP obtained for regions 1502 and 1504 presented significant hypoxic lactate peaks meanwhile lower but detectable meaningful levels of the $H_2O_2$ was recorded for region 1503. No detectable trace of any peak was measured for region 1506. The CDP response obtained for 1507, diagnosed as reference normal stroma tissue, presented no $H_2O_2$ peak similar to that observed for 1506.

The CDP response obtained for regions 1504 and 1506 were then evaluated by Ki67 IHC as an independent validation set. The expression of Ki67 has been reported to be correlated with tumor cell proliferation and growth in routine pathological investigation and used as a diagnostic marker. Ki67 based IHC classifier identified no trace of cancer proliferation in region 1506 (as the normal stroma) and showed different intensities of filtrated cancer cells in region 1504. Similar results were obtained for 5 other animal models with suspicious regions in anterior, posterior, right and left laterals of their tumors.

In addition, exemplary CDP exhibited a fine distinguishable response in interaction with another type of cancer tumors (MC4L2) as cancer cells with lower invasive grades than 4T1 as experimented on mice models. Tumors formed by the injection of about $5\times10^5$ MC4L2 cells (mice primary breast cancer cell lines) were analyzed by exemplary CDP on 5 mice.

Figure 16:
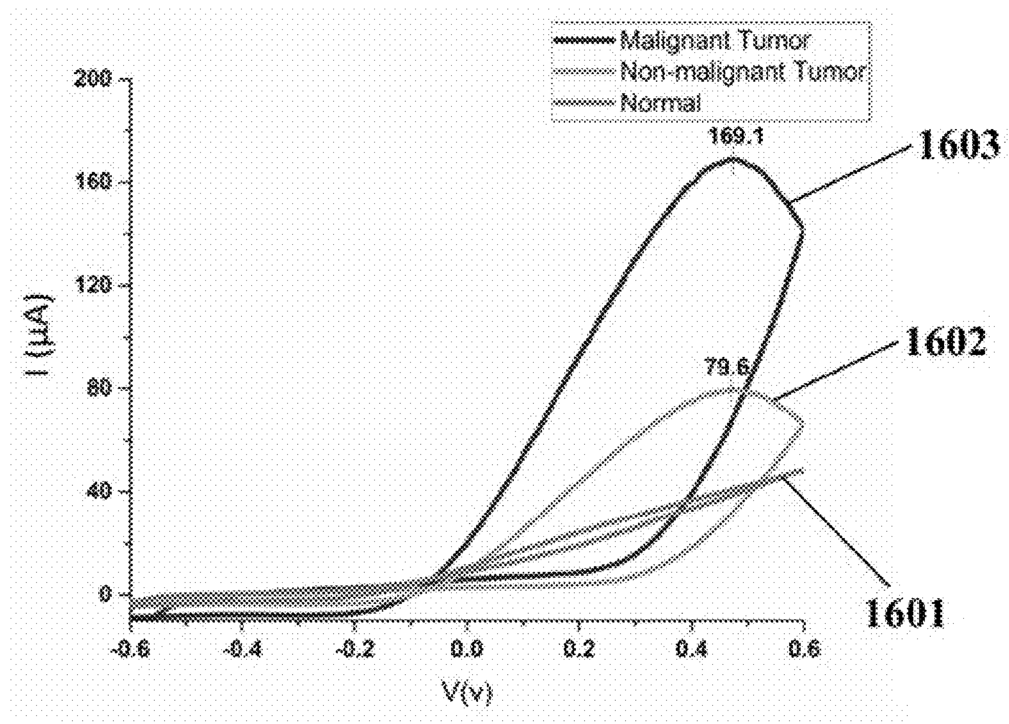
FIG. 16 illustrates comparative diagram of CDP responses in interaction with normal, nonmalignant tumor, and malignant tumor recorded from individual mice, consistent with one or more exemplary embodiments of the present disclosure.

FIG. 16 shows comparative diagram of CDP responses in interaction with normal (curve 1601), non-metastasized tumor (curve 1602) and metastatic tumor (curve 1603) recorded from individual mice, consistent with one or more exemplary embodiments of the present disclosure. Tracing the hypoxia glycolysis exhibited a strong correlation with the invasive state of the tumor. Results revealed sharply distinguishable responses between cancerous and normal regions. However the intensity of the response of MC4L2 tumors is lower than that was recorded for malignant tumor, it is observably higher than the response peak of normal tissue.

Furthermore, in this example, exemplary CDP was applied in finding the suspicious margins during tumor resection surgery in breast cancer patients. Not only the known normal domains were detected and set as reference point, but also suspicious margins of cancer and normal domains were precisely diagnosed in real-time and confirmed by histopathological assays. So, without requirement to frozen pathological process the surgeon can finish the surgery with insurance from precise resection of tumor without any additional mastectomy from the peripheral tissues.

Figure 17A:
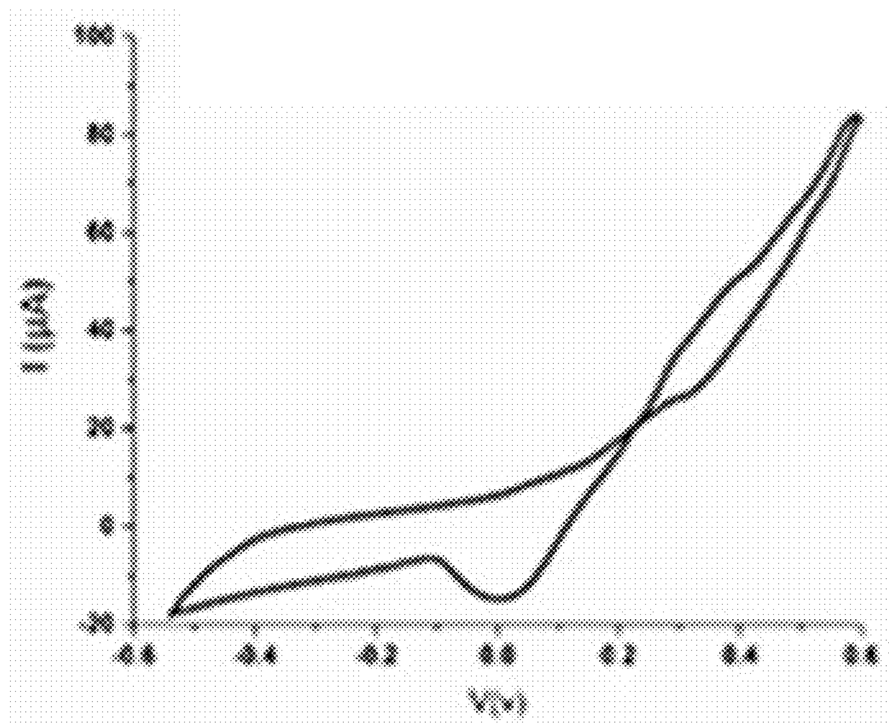
FIG. 17A illustrates CV response diagram obtained by applying exemplary CDP in detection of suspicious margins during breast cancer surgery for a known normal region, consistent with one or more exemplary embodiments of the present disclosure.
Figure 17B:
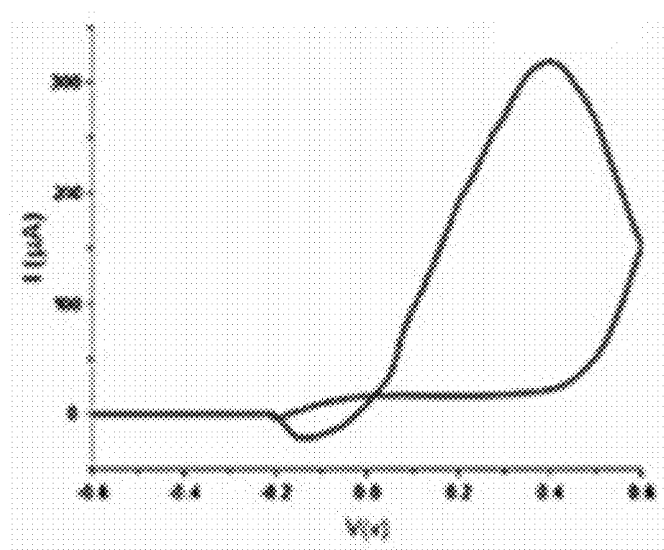
FIG. 17B illustrates CV response diagram obtained by applying exemplary CDP in detection of suspicious margins during breast cancer surgery for a suspicious region, consistent with one or more exemplary embodiments of the present disclosure.
Figure 17C:
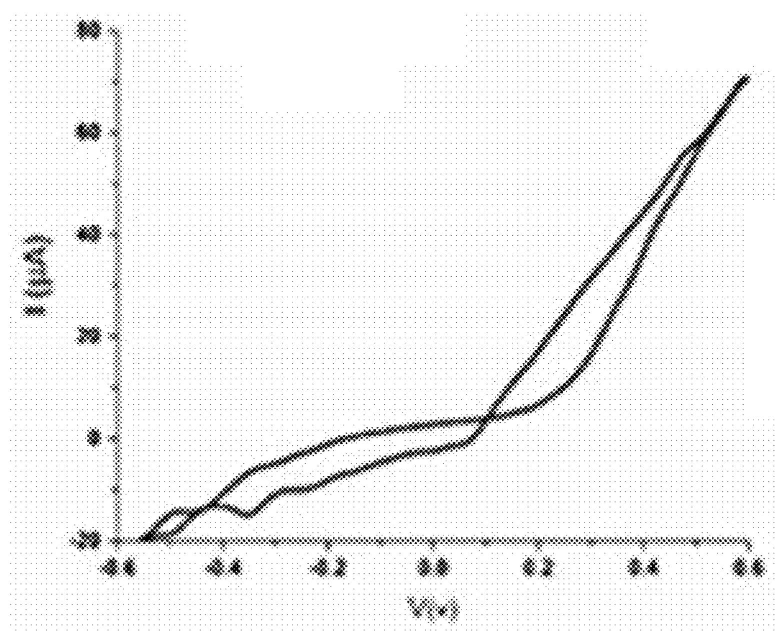
FIG. 17C illustrates CV response diagram obtained by applying exemplary CDP in detection of suspicious margins during breast cancer surgery for another suspicious region, consistent with one or more exemplary embodiments of the present disclosure.
Figure 17D:
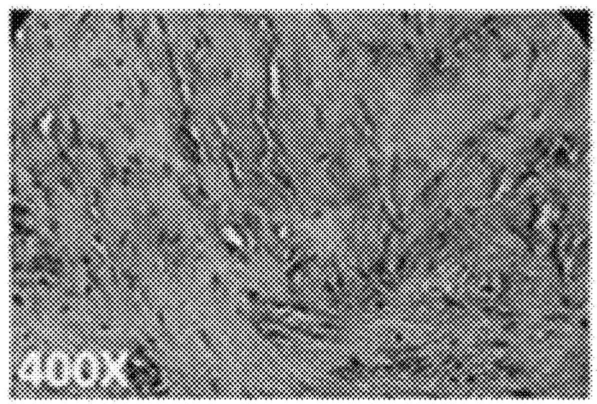
FIG. 17D illustrates an H&E resulted image after the surgery for a known normal region, consistent with one or more exemplary embodiments of the present disclosure.
Figure 17E:
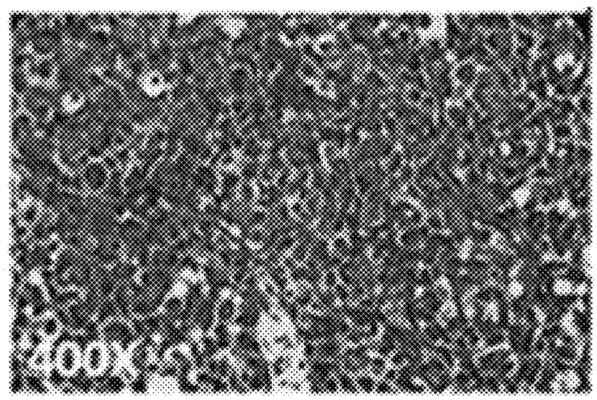
FIG. 17E illustrates an H&E resulted image after the surgery for a suspicious region, consistent with one or more exemplary embodiments of the present disclosure.
Figure 17F:
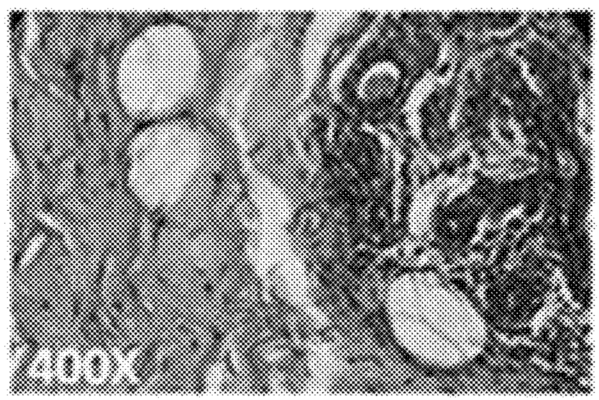
FIG. 17F illustrates an H&E resulted image after the surgery for another suspicious region, consistent with one or more exemplary embodiments of the present disclosure.

FIGS. 17A-17C shows CV responses obtained by applying exemplary CDP in detection of suspicious margins during breast cancer surgery for a known normal region (FIG. 17A) that was checked as calibrating data, and two suspicious margins (FIGS. 17B and 17C) that were precisely diagnosed as cancerous (FIG. 17B) and normal (FIG. 17C) domains by CDP in real-time, consistent with one or more exemplary embodiments of the present disclosure. The results obtained by exemplary CDP were confirmed by H&E analysis. FIGS. 17D-17F shows H&E results after the surgery for the known normal region, and two suspicious margins, consistent with one or more exemplary embodiments of the present disclosure.

These results show that the diagnostic information obtained by exemplary CDP can be used to detect cancer in marginal suspicious regions with rare distribution of cancer cells filtrated between normal stroma in less than about 20 seconds during the surgery or biopsy of live animal as well as human models without any requirement to tissue resection and preparation for frozen pathology. Even it may detect the accurate location of cancer involved regions before surgery in superficial tumors. The precision of this method is as well as reported for H&E from the assayed regions.

Example 10: Fabrication a Biopsy Guided Probe for In-Vivo Assays

In this example, an exemplary probe similar to probe 1900 was fabricated. To fabricate exemplary electrodes 1912 and 1914, two sterile needles were rinsed in deionized (DI) water and dried by air. Afterward, Ag paste was covered on a 2 mm length of the needles from top of the needles, and the rest of the needles were electrically isolated. Then, Van de Graaff electrostatic generator was used to positively charging carboxyl CNTs powder and negatively charging the needles. By moving the needles near the CNT powder, CNTs were rubbed by the needles and adhered to the top of needles in Ag paste regions. After about 10 minutes, the Ag paste dried, and CNT-decorated needles with high integration, as well as great physical and electrical connections were achieved.

Figure 23:
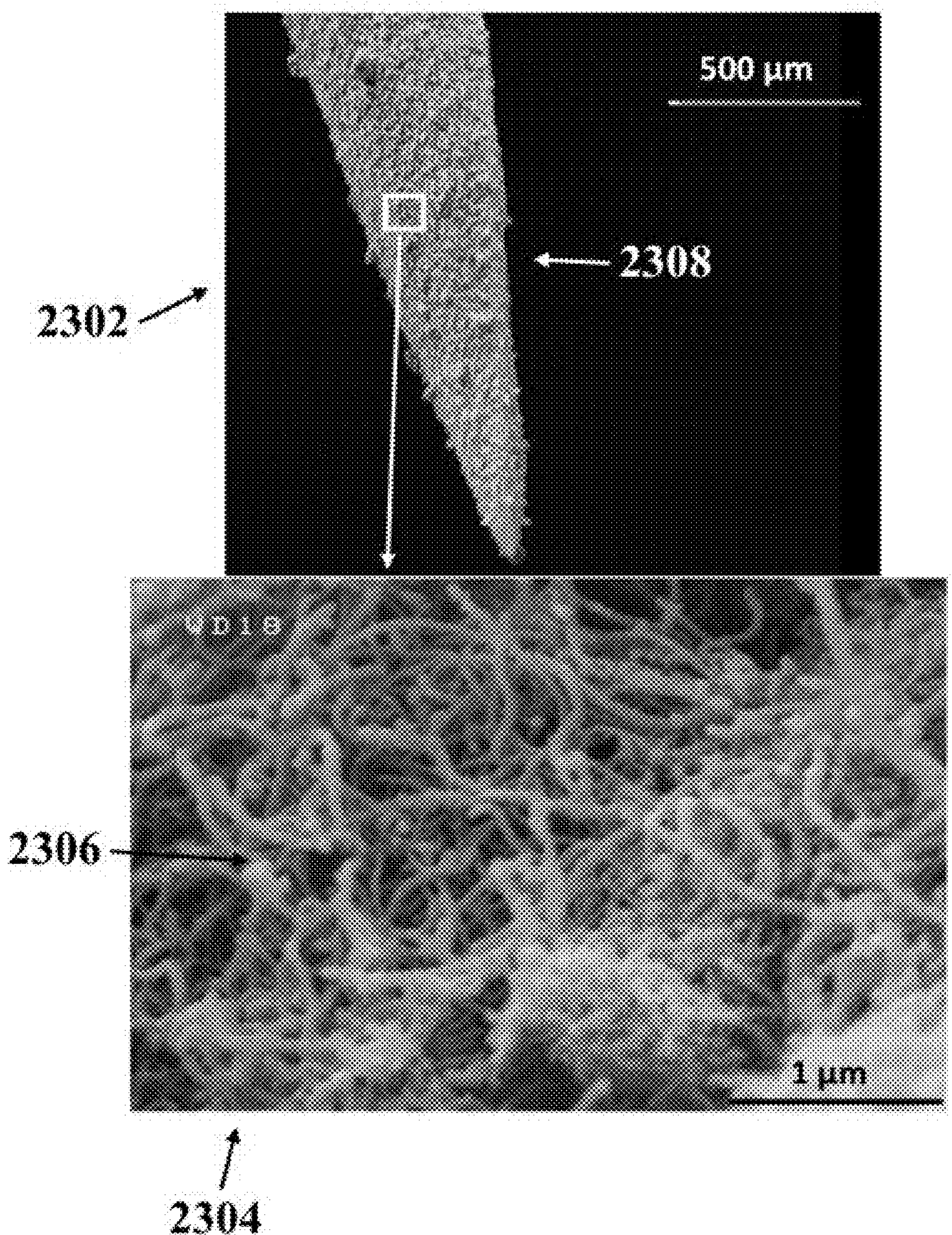
FIG. 23 shows two exemplary field emission scanning electron microscopy (FESEM) images of exemplary CNTs adhered on an exemplary tip of an exemplary needle, consistent with one or more exemplary embodiments of the present disclosure.

Deposited CNT's were characterized by field emission scanning electron microscopy (FESEM) imaging. FIG. 23 shows two FESEM images 2302 and 2304 of CNTs 2306 adhered on exemplary tip 2308 of an exemplary needle, consistent with one or more exemplary embodiments of the present disclosure. Uniform distribution and abundance of CNTs may allow for a conformal surface for signal extraction.

The fabricated working electrode and counter electrode were placed inside two reference electrodes, respectively. The reference electrodes were two steel syringes with a distance of 3 mm from each other, which dynamically capped the working electrode and the counter electrode. Reference electrodes had a thickness of 0.5 mm, and working electrode and counter electrode had a diameter of 250 μm steel needles, which can easily move inside the reference electrodes. Then, needles were attached to an electrical connector with two pins by a conductive paste. Computer-aided design (CAD) software was used to design body of the probe (i.e., exemplary parts 1902, 1904, and 1910) and a 3D printer was applied to build a three-dimensional probe body with a biocompatible material. The connector was fixed inside the body to form the final probe. Then, the probe was connected to an electrochemical stimulator-analyzer system by a noiseless cable that handled all electrodes.

Example 11: Real-Time In-Vivo Detection of Breast Tumors

In this example, exemplary fabricated probe in Example 1, which may be similar to probe 1900, was utilized according to exemplary method 1800 for tumor detection in animal models.

Firstly, cancer tumors were formed in mice. Female inbred BALB/c mice at 6-8 weeks of age were used in this example. They were kept at a temperature of about 22-24° C. with a 12 hours light/dark cycle in an utterly designed pathogen-free isolation facility and allowed to adapt for one week prior to conducting assays. 20 BALB/C female mice were divided into two groups. A total of about $2\times10^6$ 4T1 cells/200 μl in logarithmic growth phase were subcutaneously (s.c.) injected into the back neck or right side of a first group of 10 BALB/c mice. In another case for non-malignant tumor injection, a total of about $2\times10^6$ MC4L2 cells/200 μl in logarithmic growth phase were subcutaneously (s.c.) injected into the right side of a second group of 10 BALB/c mice.

After tumor formation, sonography monitoring was conducted to investigate size and probability of the presence of any necrosis in the formed tumors.

For electrochemical measurements from each mouse, the exemplary fabricated probe was sterilized under plasma sterilizer protocol. Exemplary reference electrodes (fabricated with the distance of about 3 mm from each other) of the exemplary fabricated probe were inserted into the formed tumor under a guidance of ultrasonography. After entrance of reference electrodes into the tumor location, exemplary working electrode and counter electrode were pushed from inside of the reference electrodes into the tumor location to record hypoxia related cyclic voltammetry (CV) signals released from cancer cells. Electrical potential was applied to the exemplary probe for obtaining and recording CVs. Electrical potential was swept in a range from about −0.8 V to about +0.8 V, using a scan rate of about 100 $mVs^{-1}$. After recording CVs, the working and counter electrodes were returned into the reference electrodes, and the reference electrodes were exited from body of mice. Similar tests were conducted on normal regions of the mice.

Figure 24:
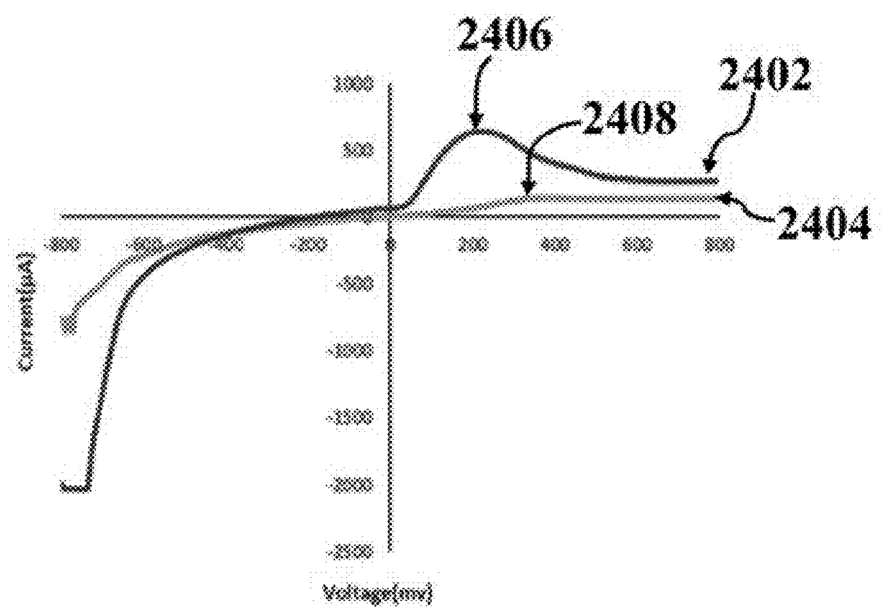
FIG. 24 shows exemplary CV diagrams recorded for exemplary normal and tumor regions, consistent with one or more exemplary embodiments of the present disclosure.

FIG. 24 shows exemplary CV diagrams recorded for normal (2404) and tumor (2402) regions, consistent with one or more exemplary embodiments of the present disclosure. It may be seen that CV current peak 2406 for cancer region is higher than CV current peak 2408 in normal region.

Figure 25:
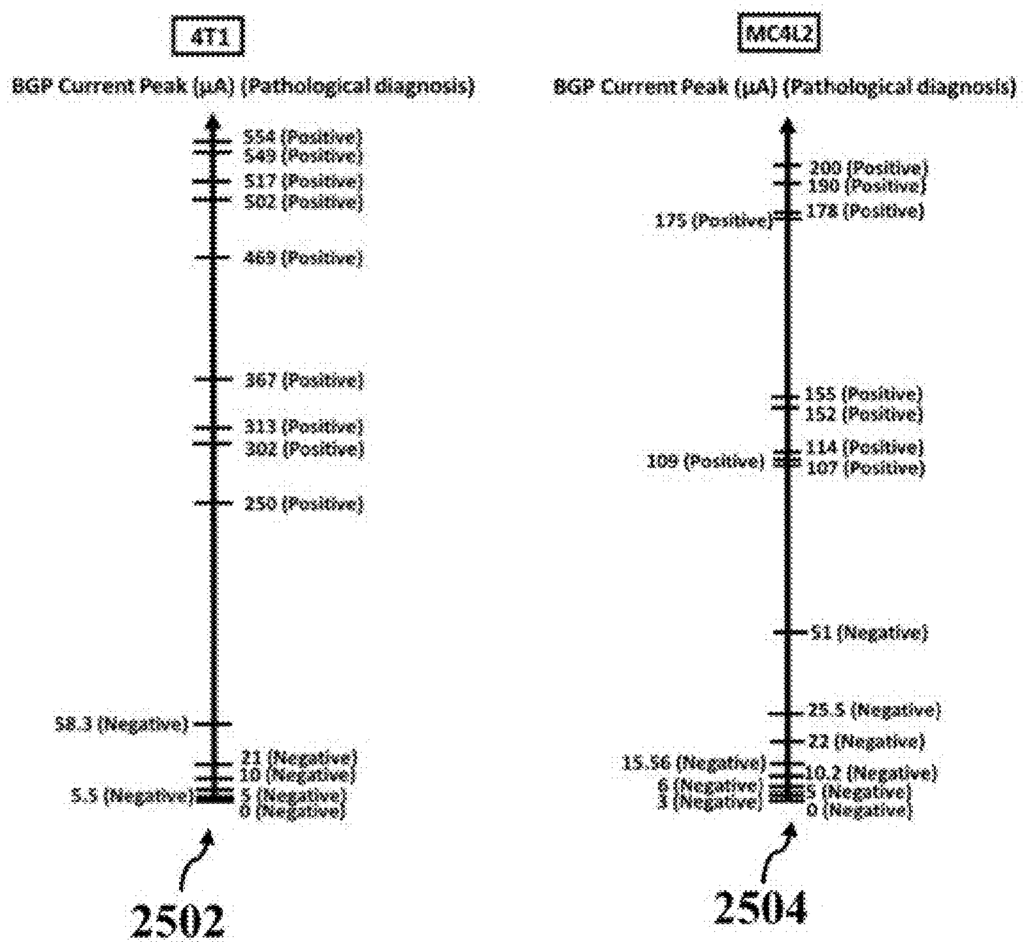
FIG. 25 shows current peak values of exemplary recorded CV diagrams and histopathological results for two groups of tumorized mice with 4T1 cancer cells and MC4L2 cancer cells, consistent with one or more exemplary embodiments of the present disclosure.
Figure 26:
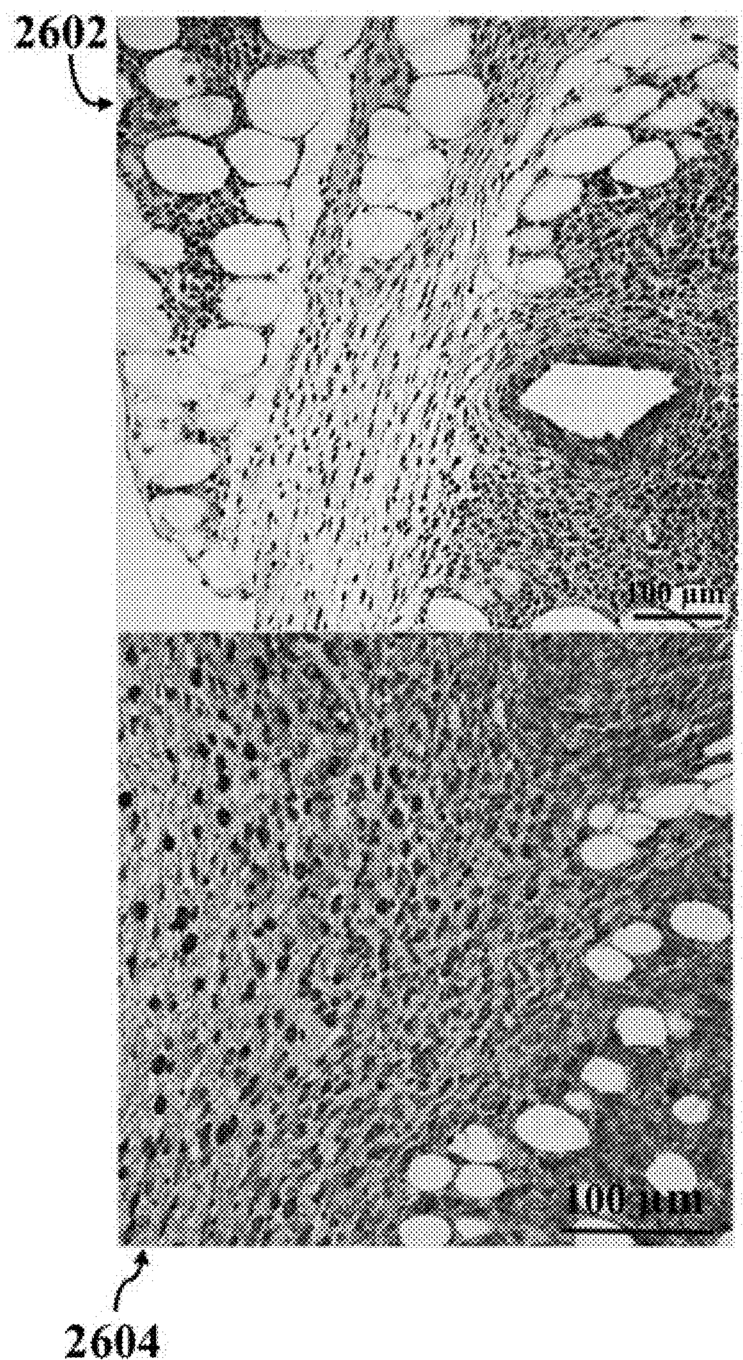
FIG. 26 shows Hematoxylin and Eosin (H&E) pattern and HIF1 alpha Immunohistochemical (IHC) pattern for an exemplary 4T1 tumor with current peak of 517 $\mu$A, consistent with one or more exemplary embodiments of the present disclosure.

Recorded CV results were compared with histopathological patterns of the tested lesions, and scaled ranges of the peak responses and respective pathological scores of diagnostics were derived. FIG. 25 shows current peak values of the recorded CV diagrams and histopathological results for two groups of tumorized mice with 4T1 cancer cells (diagram 2502) and MC4L2 cancer cells (diagram 2504), consistent with one or more exemplary embodiments of the present disclosure. Exemplary diagrams 2502 and 2504 may be utilized as calibration (reference) datasets for detection of breast cancer. In these diagrams, a gap of about 190 μA was observed between the current peaks of normal and cancer lesions. For example, lesions involved with 4T1 tumors showed CV responses with current peak values of more than about 250 μA while normal tissues of such mice showed peak currents less than about 60 μA. Similar gap was about 50 μA in mice tumorized with MC4L2 cells which means that the cancer lesions showed CV responses with current peak values of more than about 105 μA and normal tissues less than about 55 μA. FIG. 26 shows Hematoxylin and Eosin (H&E) pattern 2602 and HIF1 alpha Immunohistochemical (IHC) pattern 2604 for an exemplary 4T1 tumor with current peak of 517 μA, consistent with one or more exemplary embodiments of the present disclosure. According to comparison conducted with histopathological assays, the results obtained by the exemplary probe showed about 93% accuracy and 95% sensitivity in real-time in vivo detection of the breast tumors. Moreover, the hypoxia associated peak levels in 4T1 tumors were higher than MC4L2 tumors. This result is in great correlation with higher hypoxic functions of 4T1 cell lines. Immunohistochemical (IHC) assay of 4T1 tumor showed that most of the cancer cells expressed the hypoxia-induced factor1-alpha (HIF1-α) as an indication for their positive hypoxic functions.

Example 12: Finding Necrotic Regions of Tumors

The exemplary fabricated probe may also be applied in detecting vital state of tumors. To evaluate this, the exemplary fabricated probe was utilized for recording CV responses from 4T1 tumors before and after treating tumors by an electrochemical therapy (EChT) protocol.

Figure 27:
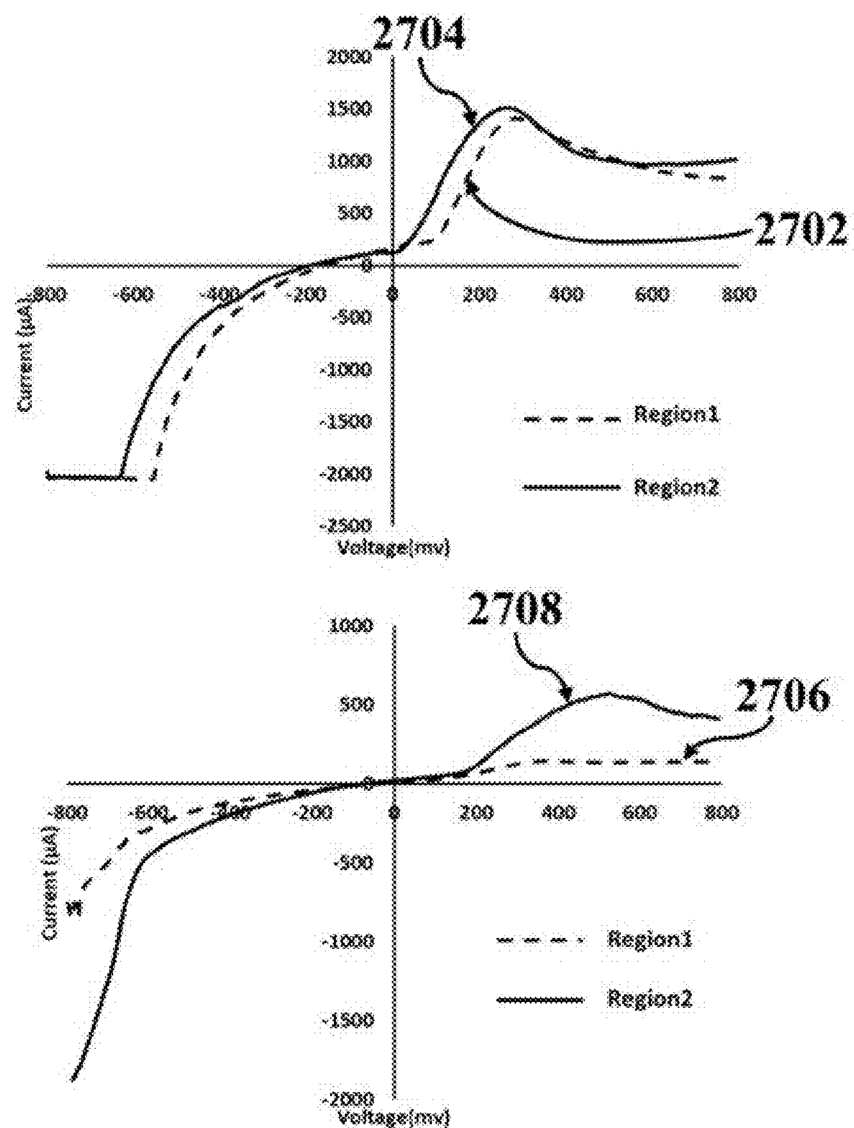
FIG. 27 shows CV responses for two exemplary regions 1 and 2 of an exemplary 4T1 tumor before any treatment, and CV responses for the two exemplary regions 1 and 2 of the exemplary 4T1 tumor after an electrochemical therapy (EChT) treatment on region 1, consistent with one or more exemplary embodiments of the present disclosure.

FIG. 27 shows CV responses 2702 and 2704 for two respective regions 1 and 2 of an exemplary 4T1 tumor before any treatment, and CV responses 2706 and 2708 for the two respective regions 1 and 2 of the exemplary 4T1 tumor after an EChT treatment on region 1, consistent with one or more exemplary embodiments of the present disclosure. Treated 4T1 region 1 showed very lower level of CV peak (CV response 2706) in comparison with non-treated region 2 (CV response 2708). It revealed that therapeutic effects on the vitality of solid tumors may be monitored by the exemplary fabricated probe without any requirements for biopsy or expensive scans.

Accordingly, the exemplary probe and method may be utilized as an alternative or a complementary tool to reduce the numbers and volumes of interventional sampling (invasive biopsy) or expensive imaging.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms “comprises,” “comprising,” or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by “a” or “an” does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A probe for non-invasively detecting and tracing cancer, comprising:

a sensing part, comprising:

two reference electrodes comprising a first needle and a second needle, each of the first needle and the second needle comprising a respective hollow needle;

a working electrode comprising a first third needle located inside the first needle, the third needle comprising a first tip coated with a first bilayer coating, the first bilayer coating comprising:

a first layer of silver (Ag) paste coated on the first tip; and a first layer of carbon nanotubes (CNTs) electrostatically grasped and adhered onto the first layer of Ag paste; and a counter electrode comprising a fourth needle located inside the second needle, the fourth needle comprising a second tip coated with a second bilayer coating, the second bilayer coating comprising:

a second layer of Ag paste coated on the second tip; and a second layer of CNTs electrostatically grasped and adhered onto the second layer of Ag paste, wherein a first respective end of each of the first needle, the second needle, the third needle, and the fourth needle is connected to an electrochemical stimulator-analyzer device via a respective electrical connector, the stimulator-analyzer device configured to measure cyclic voltammetry (CV) based diagrams; and a holding member, comprising:

an insertion part with two ends, the sensing part attached to a first end of the insertion part, the insertion part configured to facilitate insertion of the sensing part into a target location; and a button located at a second end of the insertion part, the button coupled with the working electrode and the counter electrode, the button being movable inside the insertion part, the working electrode and the counter electrode configured to be pushed outside the first and second needles through a respective second end of each of the first and second needles when the button is pressed, the working electrode and the counter electrode configured to be pulled inside the two reference electrodes through the respective second end of each of the two reference electrodes when the button is pressed again, wherein a used sensing part is configured to be replaceable with a fresh sensing part by the used sensing part being configured to be detachable from a first end of the holding member and the fresh sensing part being configured to be attachable to the first end of the holding member.

2. The probe of claim 1, wherein each of the first layer of CNTs and the second layer of CNTs comprises a layer of vertically aligned multi-walled carbon nanotubes (VAMWCNTs) functionalized by carboxyl groups.

3. The probe of claim 2, wherein:

the VAMWCNTs comprise VAMWCNTs with a length of between 0.5 μm and 10 μm, and the VAMWCNTs comprise VAMWCNTs with a diameter of between 20 nm and 100 nm.

4. The probe of claim 1, wherein each of the first needle and the second needle has a diameter twice a diameter of each of the working electrode and the counter electrode.

5. The probe of claim 1, wherein each of the two reference electrodes, the working electrode, and the counter electrode comprises a biocompatible steel needle with a diameter between 100 μm and 1 cm, and a length between 0.1 cm and 10 cm.

6. The probe of claim 1, wherein each of the first tip and the second tip has a length from a second end of each of the respective third needle and fourth needle between 0.5 mm and 5 mm.

7. The probe of claim 1, wherein the two reference electrodes are fixed apart from each other with a distance between 1 mm and 5 mm.

8. The probe of claim 1, wherein each respective hollow needle of the first needle and the second needle comprises a biocompatible electrically conductive hollow needle.

9. The probe of claim 1, wherein each respective hollow needle of the first needle and the second needle comprises a steel medical syringe.

10. The probe of claim 1, wherein each respective needle of the third needle and the fourth needle comprises a layer of an electrically isolating material covered around the needle except the respective tip of the needle.

11. The probe of claim 10, wherein the electrically isolating material comprises at least one of a biocompatible electrically isolating polymer, a biocompatible electrically isolating paste, and combinations thereof.

12. A probe for non-invasively conducting an electrochemical assay in a target location of a living tissue, comprising:

a sensing part, comprising:

two reference electrodes comprising a first needle and a second needle, each of the first needle and the second needle comprising a hollow needle, each respective hollow needle of the first needle and the second hollow needle comprising a biocompatible electrically conductive hollow needle, a first respective end of each of the first needle and the second needle being connected to an electrochemical stimulator-analyzer device via a respective electrical connector, the stimulator-analyzer device comprising a potentiostat configured to measure cyclic voltammetry (CV) based diagrams;

a working electrode located inside the first needle; and a counter electrode located inside the second needle, wherein each of the working electrode and the counter electrode comprises a biocompatible electrically conductive needle, a first end of the biocompatible electrically conductive needle being connected to the electrochemical stimulator-analyzer device via a respective electrical connector, the biocompatible electrically conductive needle comprising a needle tip coated with a bilayer coating, the bilayer comprising:

a layer of silver (Ag) paste coated on the needle tip; and a layer of carboxyl-functionalized vertically aligned multi-walled carbon nanotubes (carboxyl VAMWCNTs) electrostatically grasped and adhered onto the layer of Ag paste; and a holding member, comprising:

an insertion part with two ends, the sensing part attached to a first end of the insertion part, the insertion part configured to facilitate insertion of the sensing part into the target location; and a button at a second end of the insertion part, the button coupled with the working electrode and the counter electrode, the button being movable inside the insertion part, the working electrode and the counter electrode being releasable outside from a respective second end of the first needle and the second needle into the target location before conducting the electrochemical assay when the button being pressed, the working electrode and the counter electrode being retractable inside the two reference electrodes through the two respective second ends of the first needle and the second needle from the target location after conducting the electrochemical assay when the button is pressed again, wherein a used sensing part is replaceable with a fresh sensing part by the used sensing part being configured to detach from a first end of the holding member and the fresh sensing part being configured to attach to the first end of the holding member in lieu of the used sensing part.

13. The probe of claim 12, wherein the working electrode and the counter electrode are located apart from each other with a distance in a range of 1 mm to 5 mm.

14. The probe of claim 12, wherein the biocompatible electrically conductive needle comprises a needle with a diameter in a range of 100 μm to 1 cm and a length in a range of 0.1 cm to 10 cm.

15. The probe of claim 14, wherein each respective hollow needle of the first needle and the second needle comprises a hollow needle with a diameter twice a diameter of the biocompatible electrically conductive needle.

16. The probe of claim 12, wherein the needle tip comprises a length from a second end of the biocompatible electrically conductive needle in a range of 0.5 mm to 5 mm of each respective needle of the working electrode and the counter electrode.

17. The probe of claim 12, wherein:

the carboxyl VAMWCNTs comprise carboxyl VAMWCNTs with a length of between 0.5 μm and 10 μm, and the carboxyl VAMWCNTs comprise carboxyl VAMWCNTs with a diameter of between 20 nm and 100 nm.

18. The probe of claim 12, wherein the biocompatible electrically conductive needle further comprises a layer of an electrically isolating material covered around the biocompatible electrically conductive needle except the needle tip.

19. The probe of claim 18, wherein the electrically isolating material comprises at least one of a biocompatible electrically isolating polymer, a biocompatible electrically isolating paste, and combinations thereof.

* * * * *